United States Patent
Schaefer et al.

(10) Patent No.: US 9,502,664 B2
(45) Date of Patent: Nov. 22, 2016

(54) 4H-IMIDAZO[1,2-A]IMIDAZOLES FOR ELECTRONIC APPLICATIONS

(71) Applicant: BASF SE, Ludwigshafen (DE)

(72) Inventors: Thomas Schaefer, Liestal (CH); Ute Heinemeyer, Neustadt (DE); Nicolle Langer, Lampertheim (DE); Annemarie Wolleb, Fehren (CH); Christian Lennartz, Schifferstadt (DE); Soichi Watanabe, Mannheim (DE); Teresa Marina Figueira Duarte, Hong Kong (CN); Gerhard Wagenblast, Wachenheim (DE); Didier Bauer, Kembs (FR); Ingo Muenster, Boehl-Iggelheim (DE); Christian Schildknecht, Fremont, CA (US); Heinz Wolleb, Fehren (CH)

(73) Assignee: UDC Ireland Limited, Dublin (IE)

(*) Notice: Subject to any disclaimer, the term of this patent is extended or adjusted under 35 U.S.C. 154(b) by 391 days.

(21) Appl. No.: 14/352,861

(22) PCT Filed: Nov. 7, 2012

(86) PCT No.: PCT/EP2012/071985
§ 371 (c)(1),
(2) Date: Apr. 18, 2014

(87) PCT Pub. No.: WO2013/068376
PCT Pub. Date: May 16, 2013

(65) Prior Publication Data
US 2014/0252280 A1  Sep. 11, 2014

Related U.S. Application Data

(60) Provisional application No. 61/557,927, filed on Nov. 10, 2011.

(30) Foreign Application Priority Data

Nov. 10, 2011  (EP) .................................... 11188551

(51) Int. Cl.
| | | |
|---|---|---|
| *H01L 51/50* | (2006.01) | |
| *H01L 51/00* | (2006.01) | |
| *C07D 487/04* | (2006.01) | |
| *C09K 11/06* | (2006.01) | |
| *C09B 57/00* | (2006.01) | |
| *H05B 33/10* | (2006.01) | |
| *H05B 33/14* | (2006.01) | |

(52) U.S. Cl.
CPC ......... *H01L 51/0067* (2013.01); *C07D 487/04* (2013.01); *C09B 57/00* (2013.01); *C09K 11/06* (2013.01); *H01L 51/0072* (2013.01); *H05B 33/10* (2013.01); *H05B 33/14* (2013.01); *C09K 2211/1007* (2013.01); *C09K 2211/1011* (2013.01); *C09K 2211/1044* (2013.01); *C09K 2211/1059* (2013.01); *C09K 2211/1088* (2013.01)

(58) Field of Classification Search
None
See application file for complete search history.

(56) References Cited

U.S. PATENT DOCUMENTS

| | | |
|---|---|---|
| 6,551,723 B1 | 4/2003 | Okada et al. |
| 7,244,746 B2 | 7/2007 | Han et al. |
| 8,674,091 B2 | 3/2014 | Aihara et al. |
| 2001/0015432 A1 | 8/2001 | Igarashi |
| 2001/0019782 A1 | 9/2001 | Igarashi et al. |
| 2002/0024293 A1 | 2/2002 | Igarashi et al. |
| 2002/0048689 A1 | 4/2002 | Igarashi et al. |
| 2002/0055014 A1 | 5/2002 | Okada et al. |
| 2002/0094453 A1 | 7/2002 | Takiguchi et al. |
| 2005/0074632 A1* | 4/2005 | Lee ...................... C07D 513/04 428/690 |
| 2005/0079387 A1 | 4/2005 | Lee et al. |
| 2009/0066226 A1 | 3/2009 | Sugita et al. |
| 2009/0153035 A1 | 6/2009 | Shin et al. |
| 2010/0244006 A1* | 9/2010 | Ise ........................ C07D 487/04 257/40 |

(Continued)

FOREIGN PATENT DOCUMENTS

| | | |
|---|---|---|
| EP | 1 191 612 A2 | 3/2002 |
| EP | 1 191 613 A2 | 3/2002 |

(Continued)

OTHER PUBLICATIONS

International Search Report issued Dec. 4, 2012 in PCT/EP2012/071985.

(Continued)

*Primary Examiner* — Gregory Clark
(74) *Attorney, Agent, or Firm* — Riverside Law LLP

(57) ABSTRACT

The present invention relates to compounds of formula (I), a process for their production and their use in electronic devices, especially electroluminescent devices. When used as electron transport and/or host material for phosphorescent emitters in electroluminescent devices, the compounds of formula I may provide improved efficiency, stability, manufacturability, or spectral characteristics of electroluminescent devices.

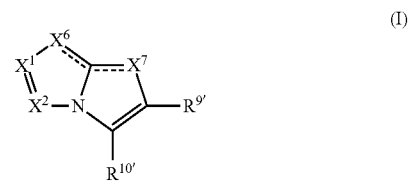

15 Claims, No Drawings

(56) References Cited

U.S. PATENT DOCUMENTS

| | | | |
|---|---|---|---|
| 2012/0241681 A1 | 9/2012 | Schaefer et al. | |
| 2013/0092922 A1 | 4/2013 | Stoessel et al. | |
| 2015/0243907 A1 | 8/2015 | Wolleb et al. | |

FOREIGN PATENT DOCUMENTS

| | | | | |
|---|---|---|---|---|
| EP | 1 211 257 A2 | 6/2002 | | |
| EP | 1 885 818 A1 | 11/2007 | | |
| EP | 1 970 976 A1 | 9/2008 | | |
| EP | 1 998 388 A1 | 12/2008 | | |
| EP | 2 034 538 A1 | 3/2009 | | |
| JP | 2000-063818 | 2/2000 | | |
| JP | 2001-160488 A | 6/2001 | | |
| JP | 2004-158327 A | 6/2004 | | |
| JP | 2004-531475 | 10/2004 | | |
| JP | 2007-180147 | * | 7/2007 | ............ H01L 51/50 |
| JP | 2007-180147 A | 7/2007 | | |
| JP | 2010-155826 | 7/2010 | | |
| KR | 10 2011 0008784 A | 1/2011 | | |
| WO | WO 99/47474 A1 | 9/1999 | | |
| WO | WO 00/70655 A2 | 11/2000 | | |
| WO | WO 01/41512 A1 | 6/2001 | | |
| WO | WO 02/02714 A2 | 1/2002 | | |
| WO | WO 02/15645 A1 | 2/2002 | | |
| WO | WO 02/060910 A1 | 8/2002 | | |
| WO | WO 2005/019373 A2 | 3/2005 | | |
| WO | WO 2005/033084 A1 | 4/2005 | | |
| WO | WO 2005/113704 A2 | 12/2005 | | |
| WO | WO 2006/056418 A2 | 6/2006 | | |
| WO | WO2006/060294 | 6/2006 | | |
| WO | WO 2006/067074 A1 | 6/2006 | | |
| WO | WO 2006/100298 A1 | 9/2006 | | |
| WO | WO 2006/115301 A1 | 11/2006 | | |
| WO | WO 2006/121811 A1 | 11/2006 | | |
| WO | WO2006/128800 A1 | 12/2006 | | |
| WO | WO 2007/095118 A2 | 8/2007 | | |
| WO | WO 2007/101820 A1 | 9/2007 | | |
| WO | WO 2007/115970 A1 | 10/2007 | | |
| WO | WO 2007/115981 A1 | 10/2007 | | |
| WO | WO 2008/000727 A1 | 1/2008 | | |
| WO | WO 2008/034758 A2 | 3/2008 | | |
| WO | WO 2009/050281 A1 | 4/2009 | | |
| WO | WO 2009/050290 A1 | 4/2009 | | |
| WO | WO 2010/056669 A1 | 5/2010 | | |
| WO | WO 2010/067894 A1 | 6/2010 | | |
| WO | WO 2010/079051 A1 | 7/2010 | | |
| WO | WO 2010/086089 A1 | 8/2010 | | |
| WO | WO 2010/129323 A1 | 11/2010 | | |
| WO | WO 2011/010842 A2 | 1/2011 | | |
| WO | WO 2011/019156 A1 | 2/2011 | | |
| WO | WO 2011/051404 A1 | 5/2011 | | |
| WO | WO 2011/073149 A1 | 6/2011 | | |
| WO | WO 2011/099718 A1 | 8/2011 | | |
| WO | WO 2011/160757 A1 | 12/2011 | | |
| WO | WO2012/023947 | 2/2012 | | |
| WO | WO 2012/080052 A1 | 6/2012 | | |
| WO | WO 2012/130709 A1 | 10/2012 | | |
| WO | WO2013/050401 | 4/2013 | | |
| WO | WO2013/068374 | 5/2013 | | |
| WO | WO2013/068376 | 5/2013 | | |

OTHER PUBLICATIONS

Pedro Molina, et al., "Synthetic Applications of C,C-Bis(Iminophosphoranes): Preparation of [5+5] Rigid Bicyclic Guanidines and 1,3,6-Benzothiadiazepino[3,2-α] benzimidazole Derivatives" Tetrahedron, vol. 50, No. 33, XP026629485, Jan. 1, 1994, pp. 10029-10036.

B.A. Priimenko, et al., "1,2-Diphenylimidazo[1,2-a] Benzimidazole in Electrophilic Substitution Reactions" Chemistry of Heterocyclic Compounds, vol. 17, 1981, pp. 937-940.

V.S. Ponomar, et al., "Investigations in the Imidazole Series LXX. Synthesis of Derivatives of 1(9)H- and 1H-Imidazo[1,2-α]Benzimidazoles" Chemistry of Heterocyclic Compounds, vol. 8, 1972, pp. 229-231.

M.V. Povstyanoi, et al., "Synthesis of 2-Methylmercapto-3-Acylmethyl(β-Hydroxyalkyl)Naphth[1,2-d]Imidazoles and their conversion to Naphth[1,2-d]Imidazo[3,2-b]Imidazole and Naphth[1,2-d]-Imidazo[3,2-b] Imidazoline Derivatives" Chemistry of Heterocyclic Compounds, vol. 8, 1972, pp. 738-741.

Misbahul Ain Khan, et al., "Tetracyclic Heteroaromatic Systems. Part-II. Benzimidazo [1,2a] Benzimidazoles" Pakistan Journal of Scientific and Industrial Research, vol. 43, No. 3, 2000, pp. 168-170.

I.V. Kolesnikova, et al., "Reaction of N-Pentafluorophenylcarbonimidoyl Dichloride with Primary Amines" Zhurnal Organicheskoi Kimii, vol. 25, 1989, pp. 1523-1529.

I.V. Kolesnikova, et al., "Reactions of N-Polyfluorophenylcarbonimidoyl Dichlorides With Primary and Secondary Amines. Kinetics and Mechanism. Synthesis of Polyfluorinated Carbodiimides, Chloroformamidines, Guanidines and Benzimidazoles" Journal of Fluorine Chemistry, vol. 40, 1988, pp. 217-246.

Reddouane Achour, et al., "Syntheses des Benzimidazolo [1,2-a] Benzimidazoles a Partir Des Benzodiazephine-1, 5ones-2" Bulletin des Societes Chimiques Beiges, vol. 96, No. 10, 1987, pp. 787-792.

Andre J. Hubert, et al., "Thermolyse and Photolyse von Benzotriazolyl-(1)-Derivaten" Chemische Berichte, vol. 103, 1970, pp. 2828-2835.

Office Action issued Dec. 14, 2015, in corresponding Japanese Patent Application No. 2014-501544, with English translation.

Kolesnikova, I.V., et al., Zhurnal Organicheskoi Khimii 25, (1989), pp. 1689-1695.

Hassaneen et al., A One Step Synthesis of Benzimidazo[2,1-c][1,2,4]Triazole Derivatives Using Hydrazonoyl Halides, Heterocycles, vol. 36, No. 8, pp. 1775-1781, (1993).

Dawood, et al., Synthesis of 3,3'-bi-1,2,4-Triazolo[4,5-a]-benzimidazole, 5,5'-bi-1,3,4-thiadiazole, and Thiazolo[3,2-a] benzimidazole Derivatives, Synthetic Communications, vol. 33, No. 23, pp. 4079-4086 (2003).

Cheminform, vol. 35, p. 2004 (referencing RevuRoumaine de Chimie, vol. 49, pp. 157-161 ( 2004).

Olaj, et al., vol. 59, pp. 49-55, Chemical Abstracts [online] [retrieved Nov. 2015 from STN] (2010).

International Search Report issued Sep. 13, 2013 in International Application No. PCT/EP2013/064395.

Xiaoqiang Wang, et al., "Copper-Catalyzed Aerobic Oxidative Intramolecular C—H Amination Leading to Imidazobenzimidazole Derivatives", Organic Letters, vol. 14, No. 2, (2012), pp. 452-455.

* cited by examiner

4H-IMIDAZO[1,2-A]IMIDAZOLES FOR ELECTRONIC APPLICATIONS

The present invention relates to compounds of formula (I), a process for their production and their use in electronic devices, especially electroluminescent devices. When used as electron transport and/or host material for phosphorescent emitters in electroluminescent devices, the compounds of formula I may provide improved efficiency, stability, manufacturability, or spectral characteristics of electroluminescent devices.

B. A. Priimenko et al, Chemistry of Heterocyclic Compounds 17 (1981) 937-40 (D1) investigate the formylation, acetylation, nitration and bromination of 1,2-diphenyl-imidazo[1,2a]benzimidazole. V. S. Ponomar et al, Chemistry of Heterocyclic Compounds 8 (1972) 229-231 (D2) disclose the synthesis of 1H-imidazo[1,2a]benzimidazole derivatives. M. V. Povstyanol et al, Chemistry of Heterocyclic Compounds 8 (1972) 738-741 (D3) disclose the synthesis of naphth[1,2-d]imidazo[3,2-b]imidazole derivatives.

Khan, Misbahul Ain; Ribeiro, Vera Lucia Teixeira, Pakistan Journal of Scientific and Industrial Research 43 (2000) 168-170 describes the synthesis of benzimidazo[1,2-a]benzimadozoles

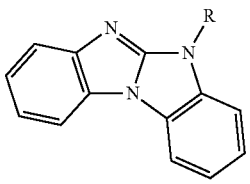

(R=H, Me, Et) by trialkyl phosphite-induced deoxygenation and thermolysis of 1-(o-nitrophenyl)- and 1-(o-azidophenyl)benzimidazoles.

Pedro Molina et al. Tetrahedron (1994) 10029-10036 reports that aza Wittig-type reaction of bis(iminophosphoranes), derived from bis(2-aminophenyl)amine with two equivalents of isocyanate directly provided benzimidazo[1,2,a]benzimidazole derivatives.

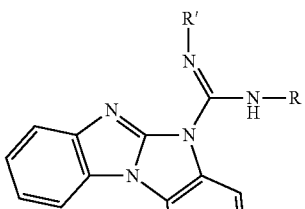

(R =R' = H₃C—⌬—, CH₃O—⌬—,
F—⌬—, —⌬—CH₂—, —cyclohexyl;
R = H₃C—⌬— and R' = CH₃O—⌬—,
R = iso-propyl and R' = ethyl)

Kolesnikova, I. V.; Zhurnal Organicheskoi Khimii 25 (1989) 1689-95 describes the synthesis of 5H-benzimidazo[1,2-a]benzimidazole 1,2,3,4,7,8,9,10-octafluoro-5-(2,3,4,5,6-pentafluorophenyl).

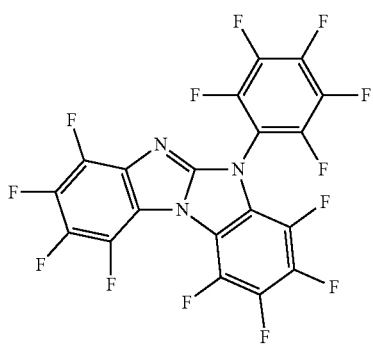 [SMILES: Fc1c(F)c(F)c(-n2c3c(F)c(F)c(F)c(F)c3n3c4c(F)c(F)c(F)c(F)c4nc23)c(F)c1F]

Achour, Reddouane; Zniber, Rachid, Bulletin des Societes Chimiques Beiges 96 (1987) 787-92 describes the synthesis of benzimidazobenzimidazoles

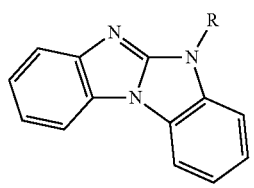

(R=H, —CH(CH₃)₂) which were prepared from benzimidazolinone derivatives.

Hubert, Andre J.; Reimlinger, Hans, Chemische Berichte 103 (1970) 2828-35 describes the synthesis of benzimidazobenzimidazoles

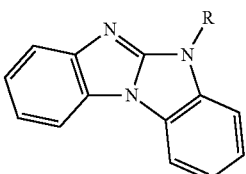

(R = H, CH₃, 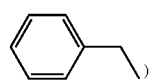)

JP2001160488 describes an electroluminescent element which has a light-emitting layer having a single-layer or multiple-layer organic compound film between opposing anode and cathode, wherein at least one layer of the organic compound film contains at least one kind of compounds indicated by formula

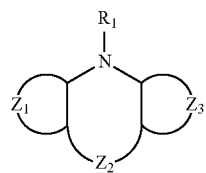

The following compounds are explicitly disclosed:

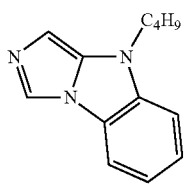 and 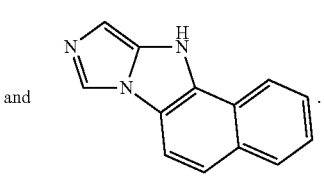

US20100244006 relates to an organic electroluminescent device which includes: a cathode; an anode; and at least one organic layer between the cathode and the anode. The at least one organic layer includes a light emitting layer containing at least one light emitting material. A compound represented by the following formula

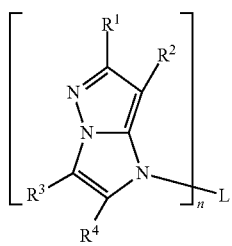

(I)

is contained in the at least one organic layer, where n stands for an integer of 2 or greater, L represents an n-valent linking group, and $R^1$, $R^2$, $R^3$, and $R^4$ each independently represents a hydrogen atom or a substituent.

The compounds described in US20100244006 are preferably used in as host in the light emitting layer.

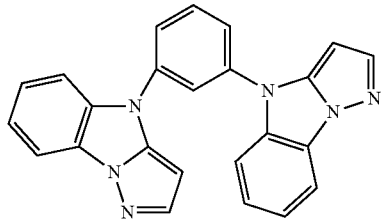 [SMILES: c1cc(-n2c3ccccc3n3nccc23)cc(-n2c3ccccc3n3nccc23)c1]

represents an example of a compound disclosed in US20100244006.

KR1020110008784 (WO2011010842) relates to novel organic luminescent compounds of formula

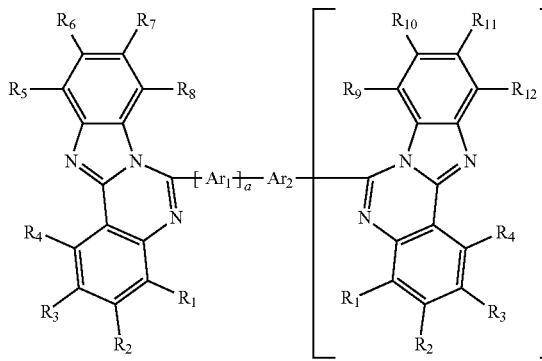

and organic electroluminescence devices including the same.

US2005079387 relates to an imidazole ring containing compound of formula $Ar_1$—$Ar_2$—$Ar_4$, (blue luminescent host compound) and an organic electroluminescence (EL) display device using the same.

$Ar_2$ is selected from the group consisting of

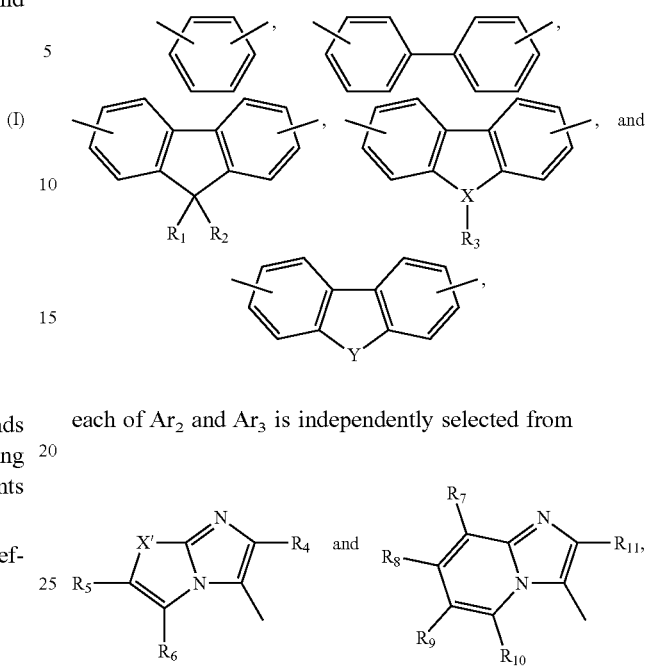

each of $Ar_2$ and $Ar_3$ is independently selected from

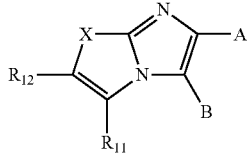

wherein X' is O, or S.

US2005074632 relates to an imidazole ring containing compound of formula

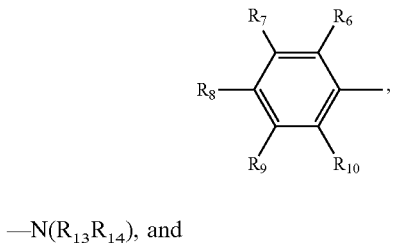

and an organic electroluminescence (EL) display device using the same. In particular, the imidazole ring-containing compound may be used alone or in combination with a dopant as a material for organic films such as an electroluminescent layer.

A is selected from the group consisting of

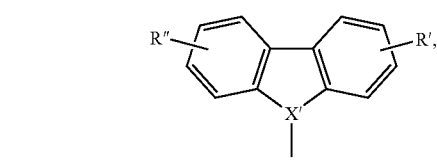

—$N(R_{13}R_{14})$, and

B is selected from the group consisting of and

X is selected from the group consisting of —O—, —S—, —Se— and —NH—.

JP2007180147 relates to an organic electroluminescence element, sandwiched by an anode and a cathode and containing at least a light-emitting layer, which contains a compound represented by general formula 1, 2, 3 or 4:

(1)

(2)

(3)

(4)

$Ar_1$-$Ar_4$=aromatic group or aromatic heterocyclic group; $R_1$-$R_5$=H or substituent; $Z_1$=residue required to form heterocyclic ring of 5 or 6 members; $L_1$, $L_2$=bond or coupling group; and $X_1$-$X_{16}$=carbon or nitrogen. A new ring can be formed in one portion of $Ar_1$ and $Ar_2$, and $Ar_3$ and $Ar_4$.

The following compounds are explicitly disclosed:

and

JP2004158327 relates to an organic electroluminescent element consists of at least one organic compound content layer provided between mutually opposing anode and cathode. The organic compound content layer contains at least one type of polymer obtained by performing ring opening polymerization of a cyclic compound of formula (I)

and at least one type of luminescent material which emits light from a triplet exciton.

The following compounds are explicitly disclosed:

, and

U.S. Pat. No. 6,551,723 relates to an organic electroluminescence element comprising a light-emitting layer or a plurality of organic compound thin layers containing a light-emitting layer between a pair of electrodes, wherein at least one layer in the organic electroluminescence element comprises at least one heterocyclic compound represented by formula (I) to (VII):

(I)

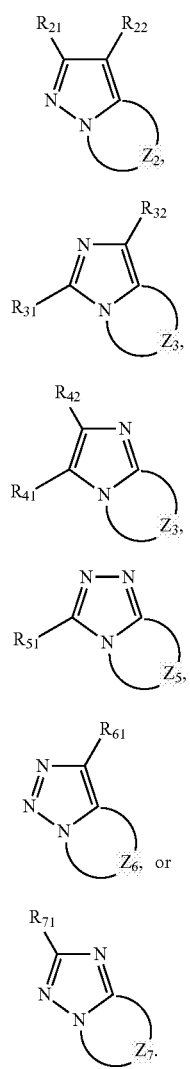

$R_{11}$, $R_{12}$, $R_{13}$, $R_{21}$, $R_{22}$, $R_{31}$, $R_{32}$, $R_{41}$, $R_{42}$, $R_{51}$, $R_{61}$, and $R_{71}$ are each independently a hydrogen atom or substituent; $Z_1$, $Z_2$, $Z_3$, $Z_4$, $Z_5$, $Z_6$, and $Z_7$ are a group of atoms that are necessary for forming a 5- or 6-member ring. The compounds represented by formula (I) to (VII) are particularly added to a light-emitting layer and/or electron injection/transporting layer. The following compounds are explicitly disclosed:

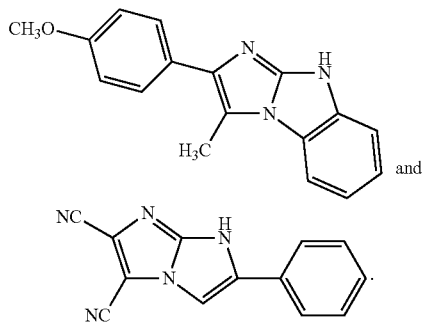

WO2011099718 relates to novel organic electroluminescent compounds of formula (I) and an organic electroluminescent device using the same:

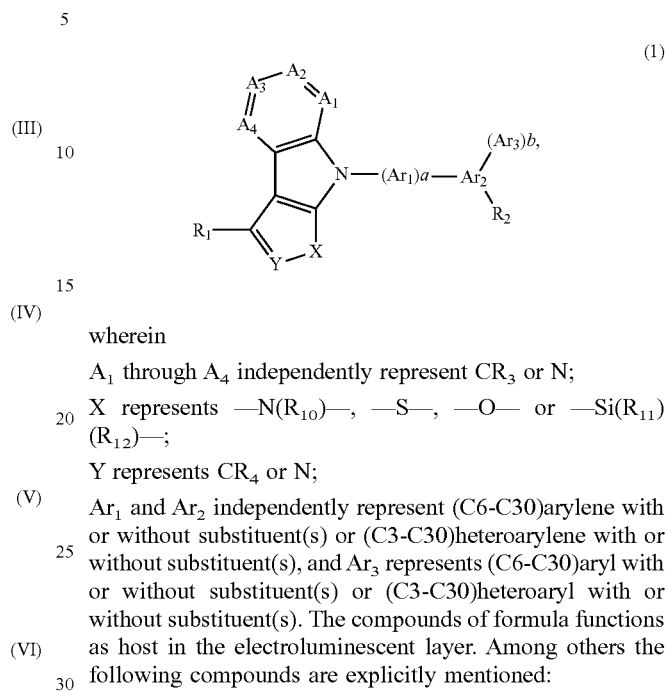

wherein
$A_1$ through $A_4$ independently represent $CR_3$ or N;
X represents —N($R_{10}$)—, —S—, —O— or —Si($R_{11}$)($R_{12}$)—;
Y represents $CR_4$ or N;
$Ar_1$ and $Ar_2$ independently represent (C6-C30)arylene with or without substituent(s) or (C3-C30)heteroarylene with or without substituent(s), and $Ar_3$ represents (C6-C30)aryl with or without substituent(s) or (C3-C30)heteroaryl with or without substituent(s). The compounds of formula functions as host in the electroluminescent layer. Among others the following compounds are explicitly mentioned:

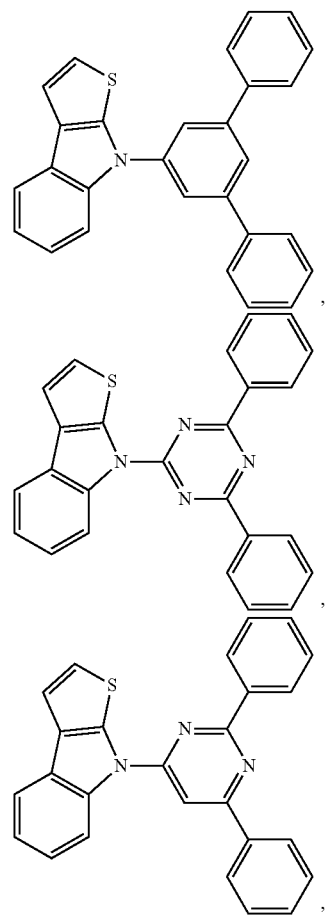

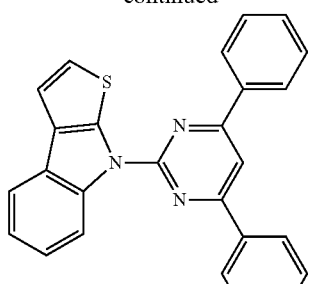
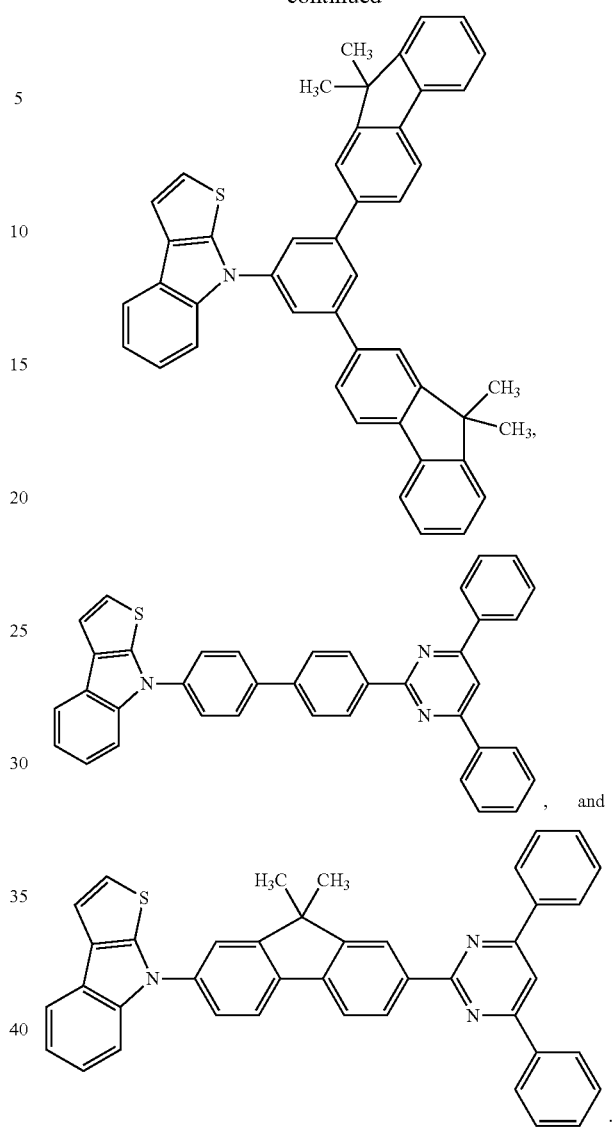
WO2011160757 relates to an electronic device comprising an anode, cathode and at least one organic layer which contains a compound of formulae
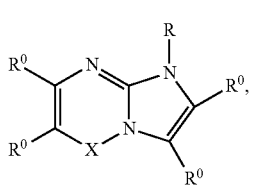
(I)
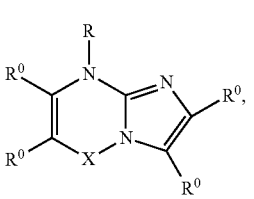
(II)

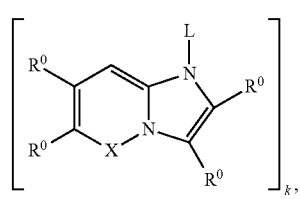
(III)
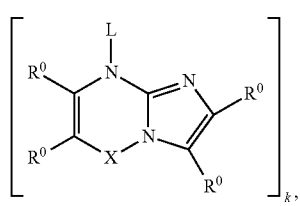
(IV)
wherein X may be a single bond and L may be a divalent group. The following 4H-Imidazo[1,2-a]imidazole compounds are explicitly disclosed:
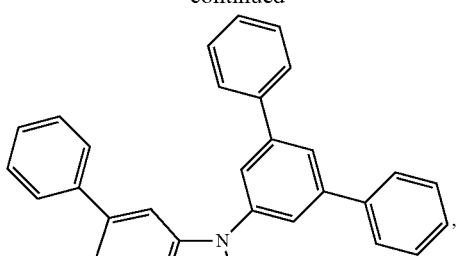
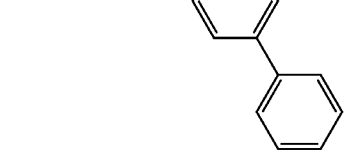
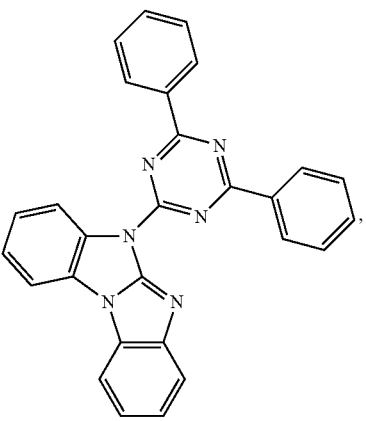
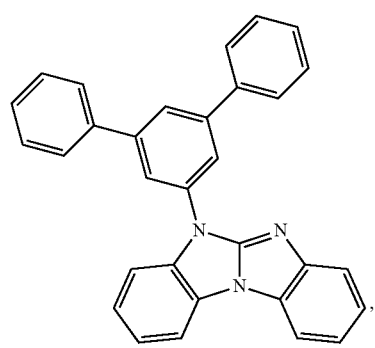
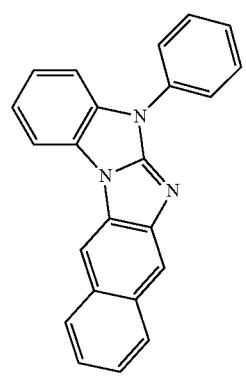
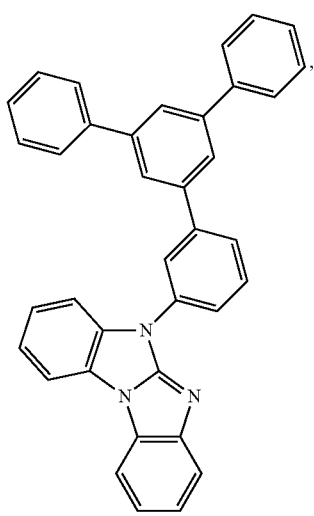
and
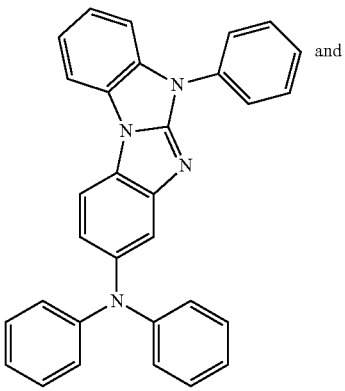

-continued

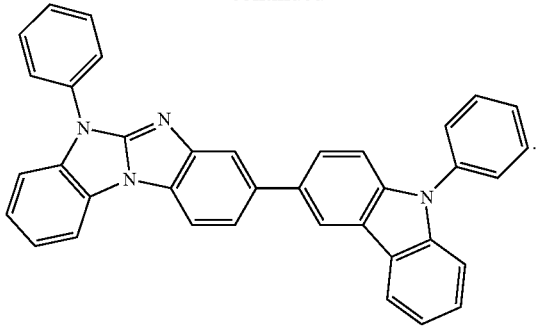

Notwithstanding these developments, there remains a need for organic light emitting devices comprising new electron transport materials to provide improved efficiency, stability, manufacturability, and/or spectral characteristics of electroluminescent devices.

Accordingly, it is an object of the present invention, with respect to the aforementioned prior art, to provide further materials suitable for use in OLEDs and further applications in organic electronics. More particularly, it should be possible to provide electron transport materials, hole/exciton blocker materials and matrix materials for use in OLEDs. The materials should be suitable especially for OLEDs which comprise at least one phosphorescence emitter, especially at least one green emitter or at least one blue emitter. Furthermore, the materials should be suitable for providing OLEDs which ensure good efficiencies, good operative lifetimes and a high stability to thermal stress, and a low use and operating voltage of the OLEDs.

Said object has been solved by compounds of the formula

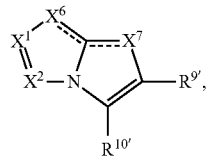

(I)

wherein $X^6$ is $-N=$ and $X^7$ is $-NR^6-$, or
$X^7$ is $=N-$ and $X^6$ is $-NR^6-$,
$R^6$ is a group of formula

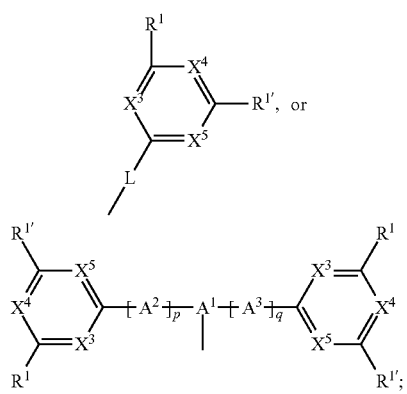

$A^1$ is a "Branching Unit" having three linkage sites,
$A^2$ and $A^3$ are independently of each other a $C_6$-$C_{24}$arylen group, which can optionally be substituted by G, or a $C_2$-$C_{30}$heteroarylen group, which can optionally be substituted by G;

wherein the groups $A^1$, $A^2$ and $A^3$ may be interrupted by one, or more groups $-(SiR^7R^8)-$;
$R^7$ and $R^8$ are independently of each other a $C_1$-$C_{25}$alkyl group, or a $C_6$-$C_{24}$aryl group, which can optionally be substituted by G;
$R^1$ and $R^{1'}$ are independently of each other H, a $C_1$-$C_{25}$alkyl group, which can optionally be substituted by E and or interrupted by D; a $C_6$-$C_{24}$aryl group, which can optionally be substituted by G, or a $C_2$-$C_{30}$heteroaryl group, which can optionally be substituted by G, including a group of formula

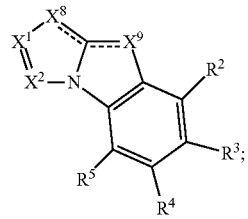

$R^2$, $R^3$, $R^4$ and $R^5$ are independently of each other H, a $C_1$-$C_{25}$alkyl group, which can optionally be substituted by E and or interrupted by D; a $C_6$-$C_{24}$aryl group, which can optionally be substituted by G, or a $C_2$-$C_{30}$heteroaryl group, which can optionally be substituted by G;
$X^8$ is $-N=$ and $X^9$ is $>N$-L-, or
$X^9$ is $=N-$ and $X^8$ is $>N$-L-;
L is a single bond, or a linking group;
$X^1$ is N, or $CR^9$,
$X^2$ is N, or $CR^{10}$,
$X^3$ is N, or $CR^{48}$,
$X^4$ is N, or $CR^{49}$,
$X^5$ is N, or $CR^{50}$, with the proviso that at least one of $X^3$, $X^4$ and $X^5$ is N,
$R^{48}$, $R^{49}$, $R^{50}$, $R^9$, $R^{10}$, $R^{9'}$ and $R^{10'}$ are independently of each other H, a $C_1$-$C_{25}$alkyl group, which can optionally be substituted by E and or interrupted by D; a $C_6$-$C_{24}$aryl group, which can optionally be substituted by G, or a $C_2$-$C_{30}$heteroaryl group, which can optionally be substituted by G; or
$R^9$ and $R^{10}$ and/or $R^{9'}$ and $R^{10'}$ together form a ring, which can optionally be substituted,
p is 0, or an integer 1, or 2; q is 0, or an integer 1, or 2;
D is $-CO-$, $-COO-$, $-S-$, $-SO-$, $-SO_2-$, $-O-$, $-NR^{65}-$, $-SiR^{70}R^{71}-$, $-POR^{72}-$, $-CR^{63}=CR^{64}-$, or $-C\equiv C-$,
E is $-OR^{69}$, $-SR^{69}$, $-NR^{65}R^{66}$, $-COR^{68}$, $-COOR^{67}$, $-CONR^{65}R^{66}$, $-CN$, or halogen,
G is E, or a $C_1$-$C_{18}$alkyl group, a $C_6$-$C_{24}$aryl group, a $C_6$-$C_{24}$aryl group which is substituted by $C_1$-$C_{18}$alkyl; a $C_2$-$C_{30}$heteroaryl group, or a $C_2$-$C_{30}$heteroaryl group, is substituted by $C_1$-$C_{18}$alkyl;
$R^{63}$ and $R^{64}$ are independently of each other H, $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by $-O-$;
$R^{65}$ and $R^{66}$ are independently of each other a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by $-O-$; or
$R^{65}$ and $R^{66}$ together form a five or six membered ring,
$R^{67}$ is a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by $-O-$, R⁶⁸ is H; a C₆-C₁₈aryl group; a C₆-C₁₈aryl group, which is substituted by C₁-C₁₈alkyl, or C₁-C₁₈alkoxy; a C₁-C₁₈alkyl group; or a C₁-C₁₈alkyl group, which is interrupted by —O—, R⁶⁹ is a C₆-C₁₈aryl; a C₆-C₁₈aryl, which is substituted by C₁-C₁₈alkyl, or C₁-C₁₈alkoxy; a C₁-C₁₈alkyl group; or a C₁-C₁₈alkyl group, which is interrupted by —O—, R⁷⁰ and R⁷¹ are independently of each other a C₁-C₁₈alkyl group, a C₆-C₁₈aryl group, or a C₆-C₁₈aryl group, which is substituted by C₁-C₁₈alkyl, and R⁷² is a C₁-C₁₈alkyl group, a C₆-C₁₈aryl group, or a C₆-C₁₈aryl group, which is substituted by C₁-C₁₈alkyl, with the proviso that the following compound is excluded:

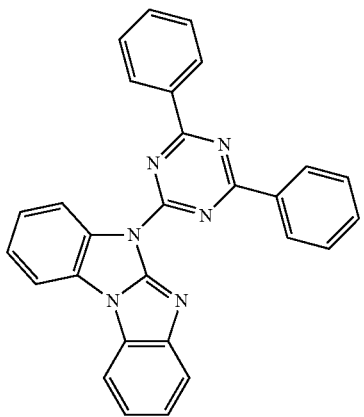

The compounds of the present invention may be used for electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and electroluminescent devices (=Organic light-emitting diodes (OLEDs)).

Accordingly, a further subject of the present invention is directed to an electronic device, comprising a compound according to the present invention. The electronic device is preferably an electroluminescent device.

The compounds of formula I can in principal be used in any layer of an EL device, but are preferably used as host, electron transport and/or hole blocking material. Particularly, the compounds of formula I are used as host and/or electron transporting material for green, or blue light emitting phosphorescent emitters with good efficiency and durability.

Hence, a further subject of the present invention is directed to an electron transport layer, comprising a compound of formula I according to the present invention.

A further subject of the present invention is directed to an emitting layer, comprising a compound of formula I according to the present invention. In said embodiment a compound of formula I is preferably used as host material in combination with a phosphorescent emitter.

A further subject of the present invention is directed to a hole blocking layer, comprising a compound of formula I according to the present invention.

The compound of formula I is preferably a compound of formula

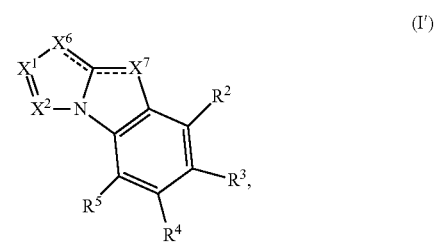

wherein $X^1$, $X^2$, $X^6$ and $X^7$ are as defined above; $R^2$, $R^3$, $R^4$ and $R^5$ are independently of each other H, a C₁-C₂₅alkyl group, which can optionally be substituted by E and or interrupted by D; a C₆-C₂₄aryl group, which can optionally be substituted by G, or a C₂-C₃₀heteroaryl group, which can optionally be substituted by G; wherein E, D and G are as defined above.

The compound of formula I' may be a compound of formula

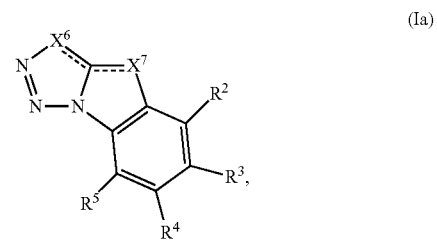

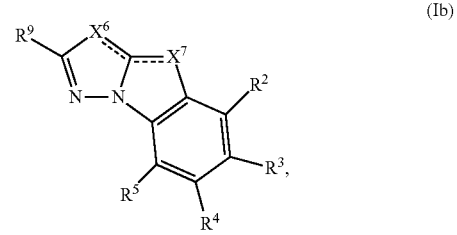

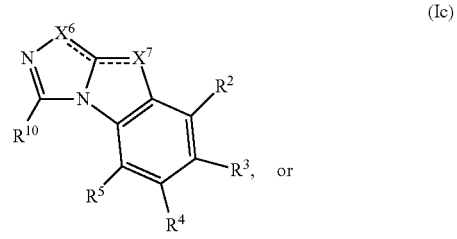

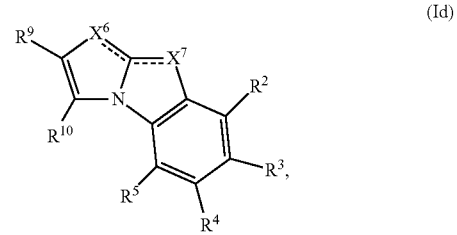

$X^6$ is —N═ and $X^7$ is or $X^7$ is ═N— and $X^6$ is —NR⁶—. Especially preferred are compounds of formula Id, wherein R⁹ and R¹⁰ together form a ring

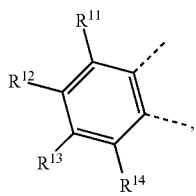

wherein $R^{11}$, $R^{12}$, $R^{13}$ and $R^{14}$ are as defined below. $R^{11}$, $R^{12}$, $R^{13}$ and $R^{14}$ are preferably H.

$R^2$, $R^3$, $R^4$ and $R^5$ are preferably H.

Compounds of formula I, which are not axially symmetric, such as, for example, compounds of formula Id, wherein $R^9$ and $R^{10}$ is H, can exist in two isomeric forms:

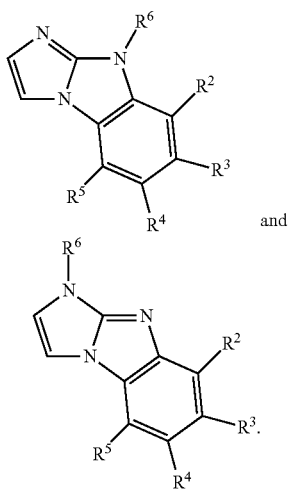

Reference is made to Example 5, which describes the synthesis of a mixture of the following compounds:

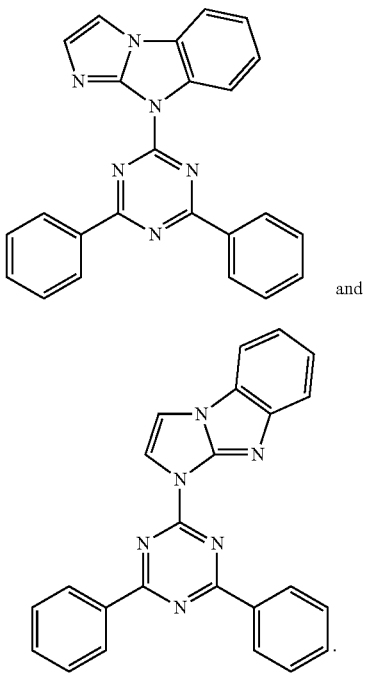

F-1a and

F-1b $R^9$ and $R^{10}$ are preferably H, $C_6$-$C_{14}$aryl, such as, for example, phenyl, naphthyl, or biphenylyl, which may optionally be substituted by one, or more $C_1$-$C_8$alkyl groups;

or $C_2$-$C_{30}$heteroaryl, such as, for example, dibenzofuranyl, which may optionally be substituted by one, or more $C_1$-$C_8$alkyl groups.

In a preferred embodiment the present invention is directed to compounds of formula (II)

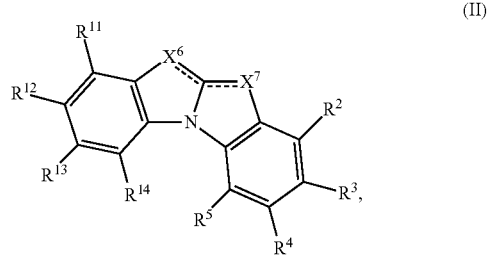

wherein $X^6$ and $X^7$ are as defined above.

$R^{11}$, $R^{12}$, $R^{13}$ and $R^{14}$ are independently of each other H, a $C_1$-$C_{25}$alkyl group, which can optionally be substituted by E and or interrupted by D; a $C_6$-$C_{24}$aryl group, which can optionally be substituted by G, or a $C_2$-$C_{30}$heteroaryl group, which can optionally be substituted by G, and E, D, G, L, $X^3$, $X^4$, $X^5$, $R^1$, $R^{1'}$, $R^2$, $R^3$, $R^4$ and $R^5$ are as defined above. Preferably, $R^2$, $R^3$, $R^4$, $R^5$, $R^{11}$, $R^{12}$, $R^{13}$ and $R^{14}$ are H.

Preferably, $X^6$ is —N= and $X^7$ is —NR$^6$—, or $X^7$ is =N— and $X^6$ is —NR$^6$—; wherein $R^6$ is a group of formula

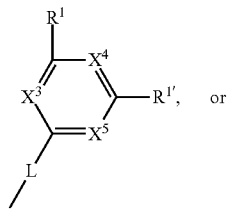

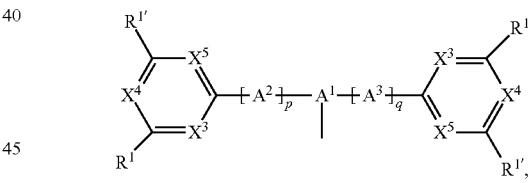

especially

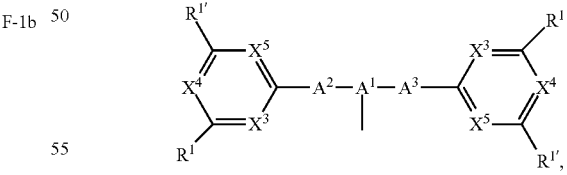

wherein $A^1$ is a group of formula

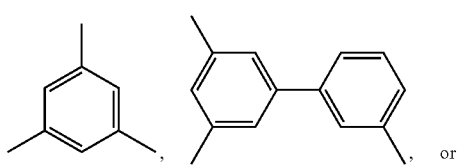

-continued

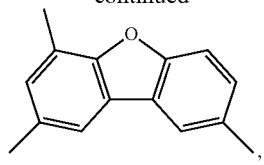

$A^2$ and $A^3$ are a group of formula

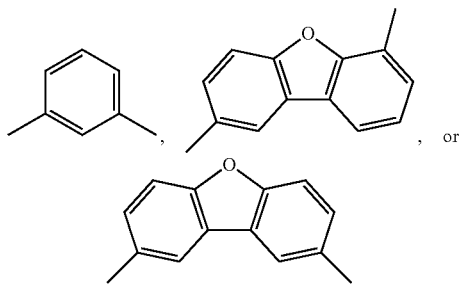

The group of formula

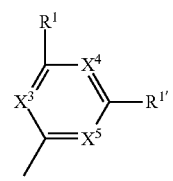

is preferably a group of formula

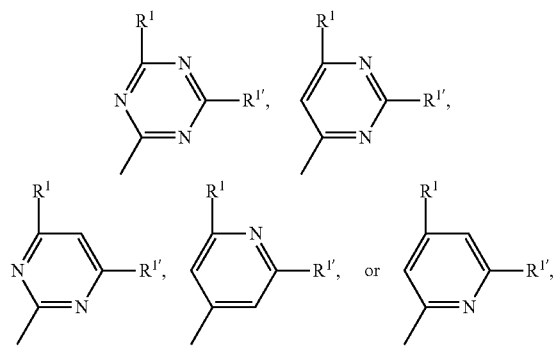

more preferably a group of formula

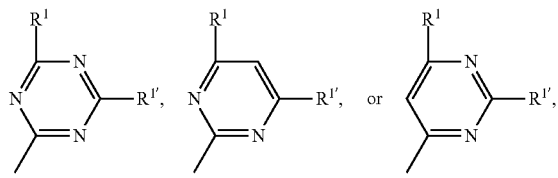

most preferred a group of formula

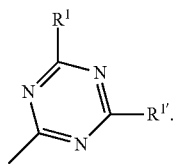

$R^1$ is preferably different from a hydrogen atom. If $X^4$ is N, $R^1$ is preferably different from a hydrogen atom. L is preferably a single bond, or a group of formula $-(A^4)_r-(A^5)_s-A^6-$, In said embodiment compounds of formula

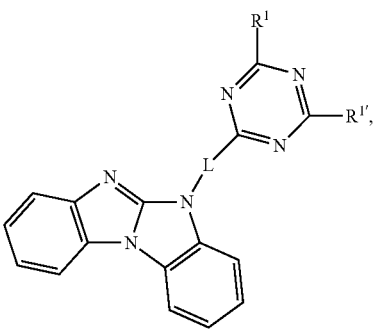

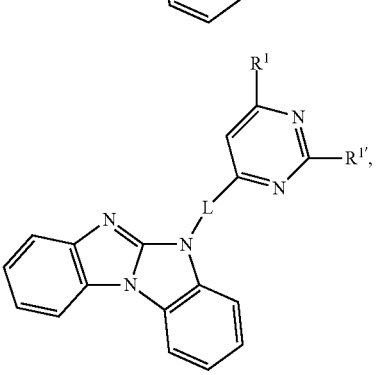

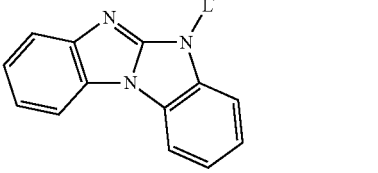

are more preferred, wherein $R^1$, $R^{1'}$ and L are as defined above.

Compounds of formula IIa, IIb and IIc are even more preferred.

$R^1$ and $R^{1'}$ may be H, a $C_1$-$C_{25}$alkyl group, which can optionally be substituted by E and or interrupted by D. A $C_6$-$C_{24}$aryl group, which can optionally be substituted by G, or a $C_2$-$C_{30}$heteroaryl group, which can optionally be substituted by G, are preferred.

The $C_6$-$C_{24}$aryl group $R^1$, or $R^{1'}$, which optionally can be substituted by G, is typically phenyl, naphthyl, especially 1-naphthyl, or 2-naphthyl, biphenylyl, terphenylyl, pyrenyl, 2-, 4-, or 9-fluorenyl, phenanthryl, or anthryl, which may be unsubstituted or substituted by, for example, one, or more $C_1$-$C_8$alkyl groups.

The $C_2$-$C_{30}$heteroaryl group $R^1$, or $R^{1'}$, which optionally can be substituted by G, represents a ring with five to seven ring atoms or a condensed ring system, wherein nitrogen, oxygen or sulfur are the possible hetero atoms, and is typically a heterocyclic group with five to 30 atoms having at least six conjugated π-electrons such as thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, 4-imidazo[1,2-a]benzimidazoyl, 5-benzimidazo[1,2-a]benzimidazoyl, carbazolyl, or phenoxazinyl, which can be unsubstituted or substituted.

Preferred $C_2$-$C_{30}$heteroaryl groups are pyridyl, triazinyl, pyrimidinyl, 4-imidazo[1,2-a]benzimidazoyl, 5-benzimidazo[1,2-a]benzimidazoyl, carbazolyl (such as, for example, 3-(9-phenyl-carbazolyl), or 9-carbazolyl), or dibenzofuranyl (such as, for example, dibenzofuran-2-yl, or dibenzofuran-4-yl), which can be unsubstituted or substituted especially by $C_6$-$C_{10}$aryl, or $C_6$-$C_{10}$aryl, which is substituted by $C_1$-$C_8$alkyl; or $C_2$-$C_5$heteroaryl.

The $C_6$-$C_{24}$aryl and $C_2$-$C_{30}$heteroaryl groups may be substituted by G and are preferably substituted by one, or more $C_1$-$C_8$alkyl groups.

L is a linking group or a single bond. In a preferred embodiment of the present invention L is a single bond. In another preferred embodiment L is a group of formula -$(A^4)_r$-$(A^5)_s$-$A^6$-, wherein r is 0, or 1; s is 0, or 1. L is preferably a single bond, or a group of formula -$(A^4)_r$-$(A^5)_s$-$A^6$-, wherein r is 0, or 1; s is 0, or 1.

$A^4$, $A^5$ and $A^6$ are independently of each other a $C_6$-$C_{24}$arylen group, which can optionally be substituted by G, or a $C_2$-$C_{30}$heteroarylen group, which can optionally be substituted by G.

The $C_6$-$C_{24}$arylen groups $A^4$, $A^5$ and $A^6$, which optionally can be substituted by G, are typically phenylene, naphthylene, especially 1-naphthylene, or 2-naphthylene, pyrenylene, 2- or 9-fluorenylene, phenanthrylene, or anthrylene, which may be unsubstituted or substituted.

The $C_2$-$C_{30}$heteroarylen groups $A^4$, $A^5$ and $A^6$, which optionally can be substituted by G, represent a ring with five to seven ring atoms or a condensed ring system, wherein nitrogen, oxygen or sulfur are the possible hetero atoms, and is typically a heterocyclic group with five to 30 atoms having at least six conjugated-electrons such as thienylene, benzothiophenylene, dibenzothiophenylene, thianthrenylene, furylene, furfurylene, 2H-pyranylene, benzofuranylene, isobenzofuranylene, dibenzofuranylene, phenoxythienylene, pyrrolylene, imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, chinolylene, isochinolylene, phthalazinylene, naphthyridinylene, chinoxalinylene, chinazolinylene, cinnolinylene, pteridinylene, carbazolylene, carbolinylene, benzotriazolylene, benzoxazolylene, phenanthridinylene, acridinylene, pyrimidinylene, phenanthrolinylene, phenazinylene, isothiazolylene, phenothiazinylene, isoxazolylene, furazanylene, carbazolylene, or phenoxazinylene, which can be unsubstituted or substituted.

Preferred $C_6$-$C_{24}$arylen groups are 1,3-phenylene, 3,3'-biphenylylene, 3,3'-m-terphenylene, 2- or 9-fluorenylene, phenanthrylene, which may be unsubstituted or substituted.

Preferred $C_2$-$C_{30}$heteroarylen groups are pyridylene, triazinylene, pyrimidinylene, carbazolylene, dibenzofuranylene which can be unsubstituted or substituted, especially by $C_6$-$C_{10}$aryl, $C_6$-$C_{10}$aryl which is substituted by $C_1$-$C_4$alkyl, or $C_2$-$C_5$heteroaryl. The $C_6$-$C_{24}$arylen and $C_2$-$C_{30}$heteroarylen groups maybe substituted by G and are preferably substituted by one, or more $C_1$-$C_8$alkyl groups.

In a preferred embodiment $A^4$, $A^5$ and $A^6$ are independently of each other a group of formula

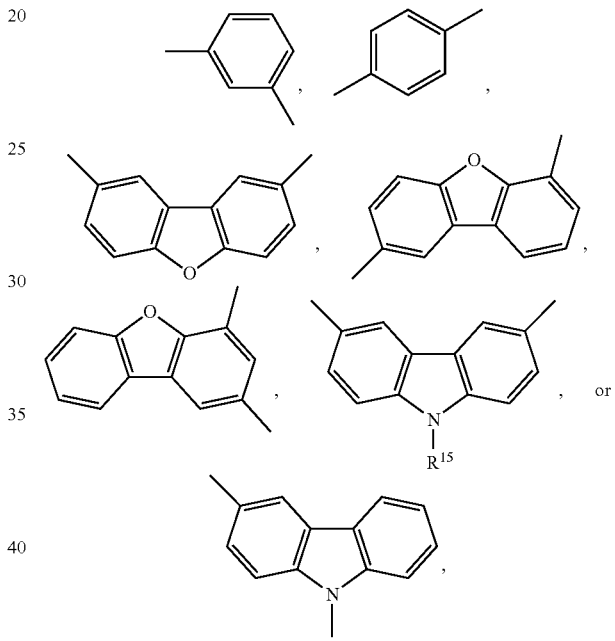

wherein $R^{15}$ is a $C_6$-$C_{18}$aryl group; or a $C_6$-$C_{18}$aryl group, which is substituted by one, or more $C_1$-$C_{18}$alkyl groups.

In a preferred embodiment L is a group of formula -$(A^4)_r$-$(A^5)_s$-$A^6$-, or wherein $A^4$, $A^5$ and $A^6$ are independently of each other a group of formula wherein
R$^{41}$ may be the same, or different in each occurrence and is F, C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, C$_2$-C$_{20}$heteroaryl, or C$_2$-C$_{20}$heteroaryl which is substituted by G,
m1 is 0, or an integer of 1 to 4,
m2 is 0, or an integer 1 to 3,
r is 0, or 1; s is 0, or 1;
X$^{13}$ is —O—, —S—, or —NR$^{15}$—,
R$^{15}$ is a C$_1$-C$_{18}$alkyl group; or a C$_1$-C$_{18}$alkyl group, which is interrupted by —O—; a C$_6$-C$_{18}$aryl group; a C$_6$-C$_{18}$aryl group, which is substituted by one, or more C$_1$-C$_{18}$alkyl groups, or C$_1$-C$_{18}$alkoxy groups; a C$_2$-C$_{20}$heteroaryl group, or a C$_2$-C$_{20}$heteroaryl group, which is substituted by one, or more C$_1$-C$_{18}$alkyl groups,
R$^7$ and R$^8$ are a C$_1$-C$_{18}$alkyl group, and
E, D and G are as defined above.

Examples of preferred groups L are shown below:

Groups of formula are preferred.

As the term "a C$_2$-C$_{30}$heteroaryl group" includes, for example, groups of formula -continued groups A¹, A² and A³ can be, for example, substituted by one, or more groups of formula and resulting, for example, in compounds of formula (III)

wherein A¹ is a group of formula

, , or

, especially ,

A² and A³ are a group of formula

, or , and R¹ and/or R¹' are a group of formula

, , or especially , ,

, ,

,

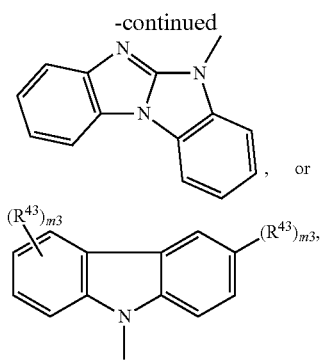, or

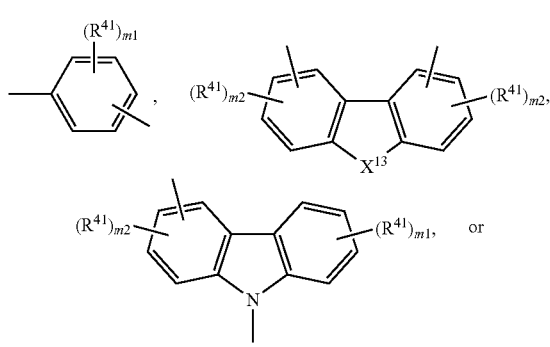

$R^{16}$ is a $C_6$-$C_{18}$aryl group; or a $C_6$-$C_{18}$aryl group, which is substituted by one, or more $C_1$-$C_{18}$alkyl groups, such as, for example, phenyl, naphthyl, or biphenylyl, which may optionally be substituted by one, or more $C_1$-$C_8$alkyl groups. $R^{91}$, $R^{92}$, $R^{93}$, $R^{94}$ and $R^{95}$ are independently of each other H, or a $C_1$-$C_{25}$alkyl group, which can optionally be substituted by E and or interrupted by D; preferably H, or a $C_1$-$C_8$alkyl group.

$R^2$, $R^3$, $R^4$, $R^5$, $R^{11}$, $R^{12}$, $R^{13}$ and $R^{14}$ are independently of each other H, a $C_1$-$C_{25}$alkyl group, which can optionally be substituted by E and or interrupted by D; a $C_6$-$C_{24}$aryl group, which can optionally be substituted by G, or a $C_2$-$C_{30}$heteroaryl group, which can optionally be substituted by G.

$R^{43}$ may be the same, or different in each occurrence and is F, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, or $C_2$-$C_{20}$heteroaryl which is substituted by G.

m3 is 0, or an integer of 1 to 4.

$X^3$ is N, or $CR^{48}$, $X^4$ is N, or $CR^{48}$ and $X^5$ is N, or $CR^{50}$, with the proviso that at least one of $X^3$, $X^4$ and $X^5$ is N.

$X^8$ is —N= and $X^9$ is >N-L-, or $X^9$ is =N— and $X^8$ is >N-L-.

p is 0, or an integer 1, or 2. q is 0, or an integer 1, or 2.

The group of formula -$(A^2)_p$-$A^1$-$(A^3)_r$- is, for example, a group of formula -$A^1$, $\backslash A^1$-$A^2$-, -$A^2$-$\backslash A^1$-$A^3$-, or -$(A^2)_2$-$A^1$-$A^3$-.

$A^2$ and $A^3$ are independently of each other a $C_6$-$C_{24}$arylen group, which can optionally be substituted by G, or a $C_2$-$C_{30}$heteroarylen group, which can optionally be substituted by G. The same preferences for $A^2$ and $A^3$ apply as for $A_4$.

Preferably, $A^2$ and $A^3$ are independently of each other a group of formula

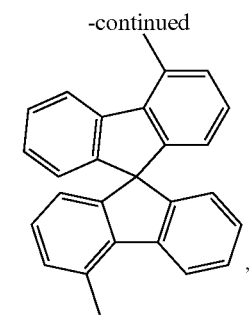

wherein
$R^{41}$ may be the same, or different in each occurrence and is F, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, or $C_2$-$C_{20}$heteroaryl which is substituted by G, m1 is 0, or an integer of 1 to 4, m2 is 0, or an integer 1 to 3, $X^{13}$ is —O—, —S—, or —N$R^{15}$—, $R^{15}$ is a $C_1$-$C_{18}$alkyl group; or a $C_1$-$C_{18}$alkyl group, which is interrupted by —O—; a $C_6$-$C_{18}$aryl group; a $C_6$-$C_{18}$aryl group, which is substituted by one, or more $C_1$-$C_{18}$alkyl groups, or $C_1$-$C_{18}$alkoxy groups; a $C_2$-$C_{20}$heteroaryl group, or a $C_2$-$C_{20}$heteroaryl group, which is substituted by one, or more $C_1$-$C_{18}$alkyl groups.

A group of formula

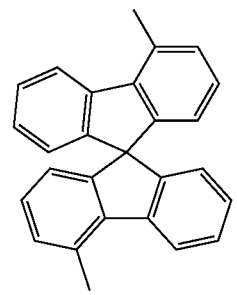 [SMILES: Cc1cccc2c1-c1ccccc1C21c2ccccc2-c2c(C)cccc21]

is less preferred than groups of formula

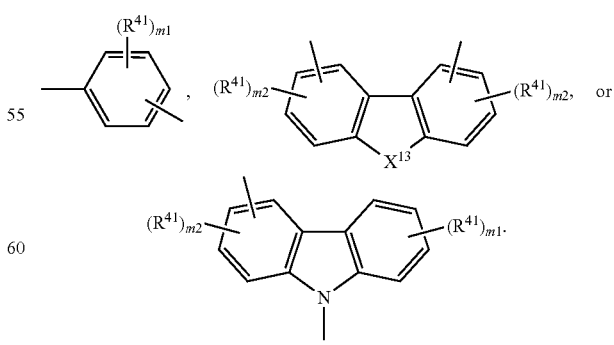

More preferably, $A^2$ and $A^3$ are independently of each other a group of formula

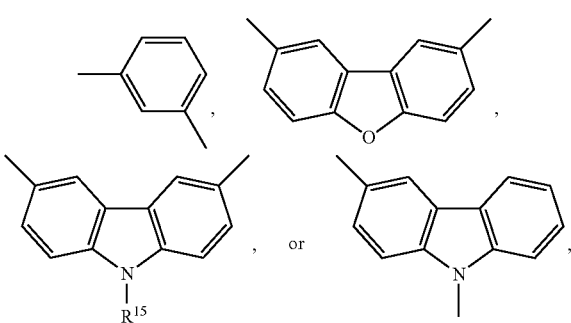

wherein R$^{15}$ is a C$_6$-C$_{18}$aryl group; or a C$_6$-C$_{18}$aryl group, which is substituted by one, or more C$_1$-C$_{18}$alkyl groups, especially

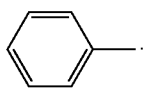

Most preferred, A$^2$ and A$^3$ are a group of formula

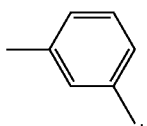

A$^1$ is a "Branching Unit" having more than two linkage sites. Examples of "Branching Units" are the above-mentioned C$_6$-C$_{24}$arylen groups, or C$_2$-C$_{30}$heteroarylen groups (which can optionally be substituted by G) having three linkage sites.

Examples of A$^1$ are groups of formula

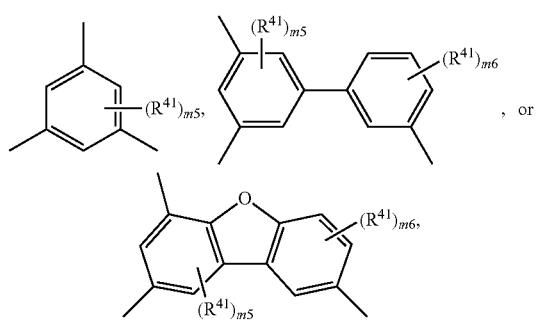

wherein R$^{41}$ is as defined above. m5 is 0, or 1 and m6 is 0, 1, or 2. m5 is preferably 0. m6 is preferably 0. Most preferred A$^1$ is a group of formula

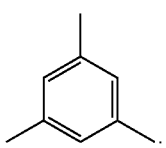

Examples of preferred groups -(A$^2$)$_p$-A$^1$-(A$^3$)$_r$- are shown below:

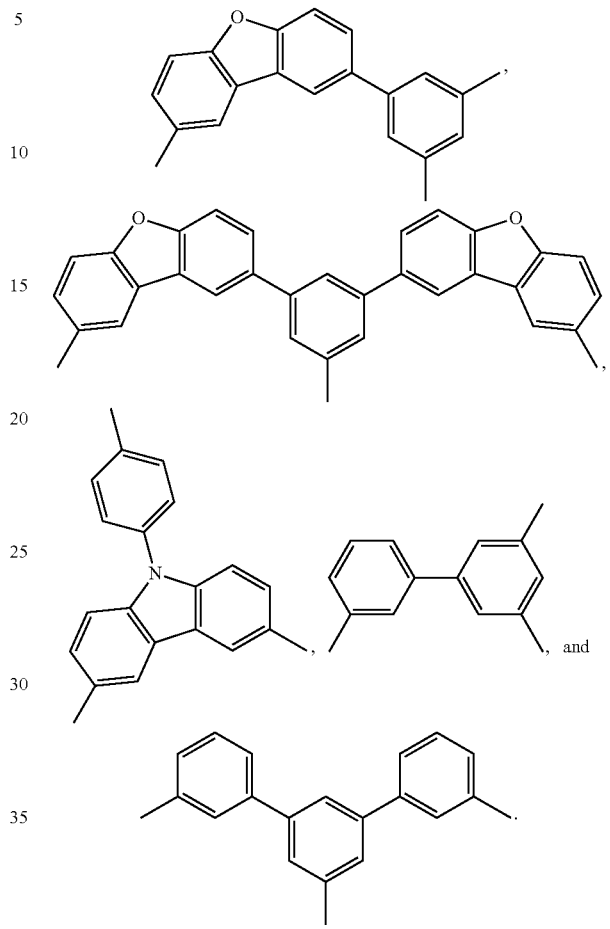

R$^1$ and R$^{1'}$ are independently of each other a group of formula

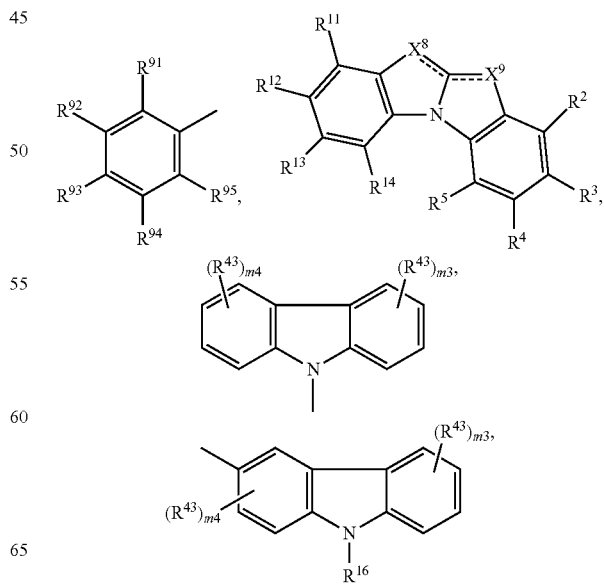

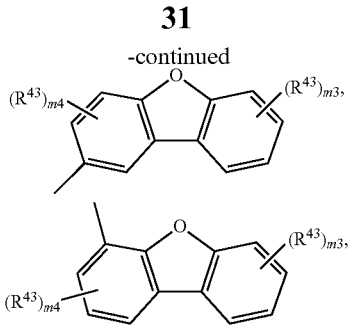

or a group —(SiR²⁰R²¹R²²), wherein
X⁸ is —N═ and X⁹ is >N-L-,
X⁹ is ═N— and X⁸ is >N-L-,
R², R³, R⁴, R⁵, R¹¹, R¹², R¹³ and R¹⁴ are independently of each other H, a $C_1$-$C_{25}$alkyl group, which can optionally be substituted by E and or interrupted by D; a $C_6$-$C_{24}$aryl group, which can optionally be substituted by G, or a $C_2$-$C_{30}$heteroaryl group, which can optionally be substituted by G,
R¹⁶ is a $C_6$-$C_{18}$aryl group; or a $C_6$-$C_{18}$aryl group, which is substituted by one, or more $C_1$-$C_{18}$alkyl groups.
R²⁰, R²¹ and R²² are independently of each other a $C_6$-$C_{18}$aryl group; or a $C_6$-$C_{18}$aryl group, which is substituted by one, or more $C_1$-$C_{18}$alkyl groups,
R⁴³ may be the same, or different in each occurrence and is F, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, or $C_2$-$C_{20}$heteroaryl which is substituted by G,
R⁹¹, R⁹², R⁹³, R⁹⁴ and R⁹⁵ are independently of each other H, a $C_1$-$C_{25}$alkyl group, which can optionally be substituted by E and or interrupted by D;
m3 is 0, or an integer of 1 to 4, m4 is 0, or an integer of 1 to 3, and
L, E, D, and G are as defined above.

More preferably, R¹ and R¹' are independently of each other a group of formula

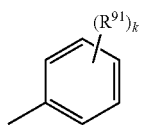

(k is 0, 1, 2, or 3 and R⁹¹ is H, or $C_1$-$C_8$alkyl), such as, for example,

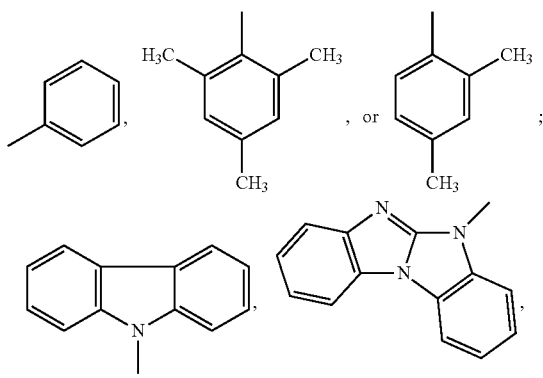

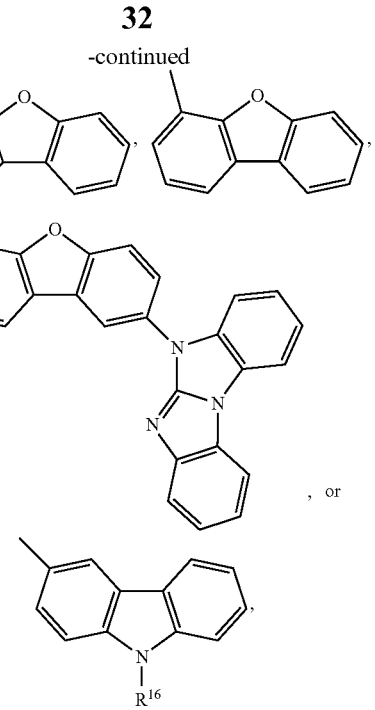

R¹⁶ is a $C_6$-$C_{18}$aryl group; or a $C_6$-$C_{18}$aryl group, which is substituted by one, or more $C_1$-$C_{18}$alkyl groups, especially

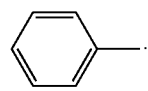

D is preferably —CO—, —COO—, —S—, —SO—, —SO₂—, —O—, —NR⁶⁵—, wherein R⁶⁵ is $C_6$-$C_{18}$alkyl, such as methyl, ethyl, n-propyl, iso-propyl, n-butyl, isobutyl, or sec-butyl, or $C_6$-$C_{14}$aryl, such as phenyl, tolyl, naphthyl, or biphenylyl.
E is preferably —OR⁶⁹; —SR⁶⁹; —NR⁶⁵R⁶⁵; —COR⁶⁸; —COOR⁶⁷; —CONR⁶⁵R⁶⁵; or —CN; wherein R⁶⁵, R⁶⁷, R⁶⁸ and R⁶⁹ are independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as, for example, phenyl, naphthyl, especially 1-naphthyl, or 2-naphthyl, biphenylyl, terphenylyl, pyrenyl, 2-, 4-, or 9-fluorenyl, phenanthryl, or anthryl, which may be unsubstituted or substituted by, for example, one, or more $C_1$-$C_8$alkyl groups; or $C_2$-$C_{30}$heteroaryl, such as, for example, pyridyl, triazinyl, pyrimidinyl, 4-imidazo[1,2-a]benzimidazoyl, 5-benzimidazo[1,2-a]benzimidazoyl, carbazolyl (such as, for example, 3-(9-phenyl-carbazolyl), or 9-carbazolyl), or dibenzofuranyl (such as, for example, dibenzofuran-2-yl, or dibenzofuran-4-yl), which can be unsubstituted or substituted especially by $C_6$-$C_{10}$aryl, or $C_6$-$C_{10}$aryl, which is substituted by $C_1$-$C_8$alkyl.
G has the same preferences as E, or is $C_6$-$C_{18}$alkyl, such as methyl, ethyl, n-propyl, iso-propyl, n-butyl, isobutyl, sec-butyl, hexyl, octyl, or 2-ethyl-hexyl, or is $C_6$-$C_{18}$perfluoroalkyl, such, for example, —CF₃.
R², R³, R⁴, R⁵R¹¹, R¹², R¹³ and R¹⁴ are preferably H.
R⁴¹ is preferably H, $C_6$-$C_{14}$aryl, such as phenyl, tolyl, naphthyl, or biphenylyl, which may optionally be substituted by $C_1$-$C_8$alkyl.
R⁴³ is preferably H, $C_6$-$C_{14}$aryl, such as phenyl, tolyl, naphthyl, or biphenylyl, which may optionally be substituted by $C_1$-$C_8$alkyl.

m3 is preferably 0, or 1, most preferred 0. m4 is preferably 0, or 1, most preferred 0.

Examples of preferred compounds of formula I are compounds A-1 to A-18, B-1 to B-18, C-1 to C-18 and D-1 to D-19 shown in claim 9.

Halogen is fluorine, chlorine, bromine and iodine.

$C_1$-$C_{25}$alkyl ($C_6$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy.

The term "cycloalkyl group" is typically $C_4$-$C_8$cycloalkyl, especially $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted.

$C_6$-$C_{24}$aryl ($C_6$-$C_{18}$aryl), which optionally can be substituted, is typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, which may be unsubstituted or substituted.

$C_2$-$C_{30}$heteroaryl ($C_2$-$C_{20}$heteroaryl) represents a ring with five to seven ring atoms or a condensed ring system, wherein nitrogen, oxygen or sulfur are the possible hetero atoms, and is typically a heterocyclic group with five to 30 atoms having at least six conjugated π-electrons such as thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, 4-imidazo[1,2-a]benzimidazoyl, 5-benzimidazo[1,2-a]benzimidazoyl, carbazolyl, or phenoxazinyl, which can be unsubstituted or substituted.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, or a cyano group.

The $C_6$-$C_{24}$aryl ($C_6$-$C_{18}$aryl) and $C_2$-$C_{30}$heteroaryl groups are preferably substituted by one, or more $C_1$-$C_8$alkyl groups.

The term "aryl ether group" is typically a $C_{6-24}$aryloxy group, that is to say O—$C_{6-24}$aryl, such as, for example, phenoxy or 4-methoxyphenyl.

If a substituent, such as, for example $R^{41}$ occurs more than one time in a group, it can be different in each occurrence.

The wording "substituted by G" means that one, or more, especially one to three substituents G might be present.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—CH($C_2H_5$) $C_4H_9$), $CH_2$—$CH(OR^{y'})$—$CH_2$—O—$R^y$, where $R^y$ is $C_1$-$C_{18}$alkyl, $C_5$-$C_{12}$cycloalkyl, phenyl, $C_7$-$C_{15}$-phenylalkyl, and $R^{y'}$ embraces the same definitions as $R^y$ or is H; $C_1$-$C_8$alkylene-COO—$R^z$, e.g. $CH_2COOR^z$, $CH(CH_3)CO$-$OR^z$, $C(CH_3)_2COOR^z$, where $R^z$ is H, $C_1$-$C_{18}$alkyl, $(CH_2CH_2O)_{1-9}$—$R^x$, and $R^x$ embraces the definitions indicated above; $CH_2CH_2$—O—CO—CH=$CH_2$; $CH_2CH(OH)$ $CH_2$—O—CO—$C(CH_3)$=$CH_2$.

The synthesis of

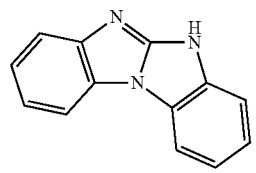 [SMILES: c1ccc2c(c1)nc1[nH]c3ccccc3n12]

is described, for example, in Achour, Reddouane; Zniber, Rachid, Bulletin des Societes Chimiques Beiges 96 (1987) 787-92.

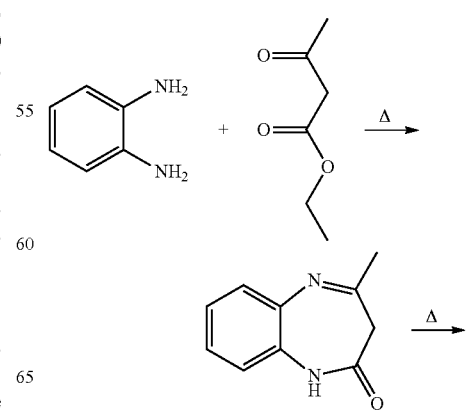

-continued

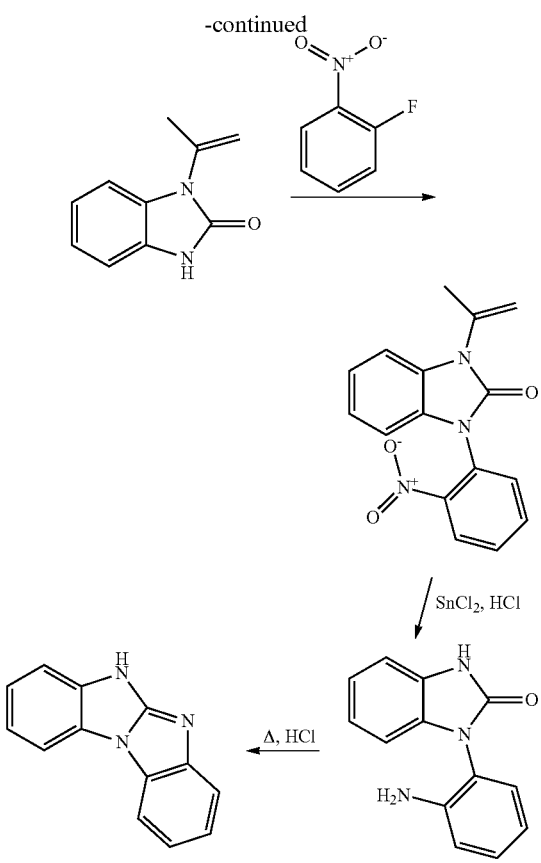

Suitable base skeletons of the formula

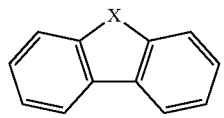

are either commercially available (especially in the cases when X is S, O, NH), or can be obtained by processes known to those skilled in the art. Reference is made to WO2010079051 and EP1885818.

The halogenation can be performed by methods known to those skilled in the art. Preference is given to brominating or iodinating in the 3 and 6 positions (dibromination) or in the 3 or 6 positions (monobromination) of the base skeleton of the formula (II) 2,8 positions (dibenzofuran and dibenzothiophene) or 3,6 positions (carbazole).

Optionally substituted dibenzofurans, dibenzothiophenes and carbazoles can be dibrominated in the 2,8 positions (dibenzofuran and dibenzothiophene) or 3,6 positions (carbazole) with bromine or NBS in glacial acetic acid or in chloroform. For example, the bromination with $Br_2$ can be effected in glacial acetic acid or chloroform at low temperatures, e.g. 0° C. Suitable processes are described, for example, in M. Park, J. R. Buck, C. J. Rizzo, Tetrahedron, 54 (1998) 12707-12714 for X=NPh, and in W. Yang et al., J. Mater. Chem. 13 (2003) 1351 for X=S. In addition, 3,6-dibromocarbazole, 3,6-dibromo-9-phenylcarbazole, 2,8-dibromodibenzothiophene, 2,8-dibromodibenzofuran, 2-bromocarbazole, 3-bromodibenzothiophene, 3-bromodibenzofuran, 3-bromocarbazole, 2-bromodibenzothiophene and 2-bromodibenzofuran are commercially available.

Monobromination in the 4 position of dibenzofuran (and analogously for dibenzothiophene) is described, for example, in J. Am. Chem. Soc. 1984, 106, 7150. Dibenzofuran (dibenzothiophene) can be monobrominated in the 3 position by a sequence known to those skilled in the art, comprising a nitration, reduction and subsequent Sandmeyer reaction.

Monobromination in the 2 position of dibenzofuran or dibenzothiophene and monobromination in the 3 position of carbazole are effected analogously to the dibromination, with the exception that only one equivalent of bromine or NBS is added.

Alternatively, it is also possible to utilize iodinated dibenzofurans, dibenzothiophenes and carbazoles.

The preparation is described, inter alia, in Tetrahedron. Lett. 47 (2006) 6957-6960, Eur. J. Inorg. Chem. 24 (2005) 4976-4984, J. Heterocyclic Chem. 39 (2002) 933-941, J. Am. Chem. Soc. 124 (2002) 11900-11907, J. Heterocyclic Chem, 38 (2001) 77-87.

For the nucleophilic substitution, Cl- or F-substituted dibenzofurans, dibenzothiophenes and carbazoles are required. The chlorination is described, inter alia, in J. Heterocyclic Chemistry, 34 (1997) 891-900, Org. Lett., 6 (2004) 3501-3504; J. Chem. Soc. [Section] C: Organic, 16 (1971) 2775-7, Tetrahedron Lett. 25 (1984) 5363-6, J. Org. Chem. 69 (2004) 8177-8182. The fluorination is described in J. Org. Chem. 63 (1998) 878-880 and J. Chem. Soc., Perkin Trans. 2, 5 (2002) 953-957.

The introduction of the group

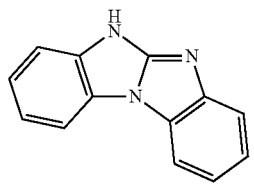 [SMILES: c1ccc2c(c1)nc1[nH]c3ccccc3n12]

is performed in the presence of a base. Suitable bases are known to those skilled in the art and are preferably selected from the group consisting of alkali metal and alkaline earth metal hydroxides such as NaOH, KOH, $Ca(OH)_2$, alkali metal hydrides such as NaH, KH, alkali metal amides such as $NaNH_2$, alkali metal or alkaline earth metal carbonates such as $K_2CO_3$ or $Cs_2CO_3$, and alkali metal alkoxides such as NaOMe, NaOEt. In addition, mixtures of the aforementioned bases are suitable. Particular preference is given to NaOH, KOH, NaH or $K_2CO_3$.

Heteroarylation can be effected, for example, by copper-catalyzed coupling of

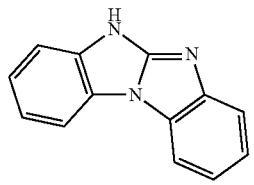 [SMILES: c1ccc2c(c1)nc1[nH]c3ccccc3n12]

to a halogenated compound of the formula

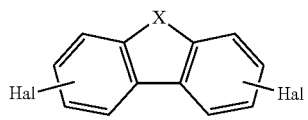

(Ullmann reaction).

The N-arylation was, for example, disclosed in H. Gilman and D. A. Shirley, J. Am. Chem. Soc. 66 (1944) 888; D. Li et al., Dyes and Pigments 49 (2001) 181-186 and Eur. J. Org. Chem. (2007) 2147-2151. The reaction can be performed in solvent or in a melt. Suitable solvents are, for example, (polar) aprotic solvents such as dimethyl sulfoxide, dimethylformamide, N-methyl-2-pyrrolidone (NMP), tridecane or alcohols.

The synthesis of 9-(8-bromodibenzofuran-2-yl)carbazole,

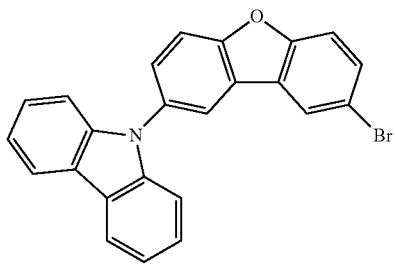 [SMILES: Brc1ccc2oc3ccc(-n4c5ccccc5c5ccccc54)cc3c2c1]

is described in WO2010079051. The synthesis of 2-bromo-8-iodo-dibenzofurane,

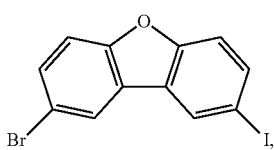 [SMILES: Brc1ccc2oc3ccc(I)cc3c2c1]

is described in EP1885818.

Diboronic acid or diboronate group containing dibenzofurans, dibenzothiophenes and carbazoles can be readily prepared by an increasing number of routes. An overview of the synthetic routes is, for example, given in Angew. Chem. Int. Ed. 48 (2009) 9240-9261.

By one common route diboronic acid or diboronate group containing dibenzofurans, dibenzothiophenes, and carbazoles can be obtained by reacting halogenated dibenzofurans, dibenzothiophenes and carbazoles with $(OY^1)_2B$—$B(OY^1)_2$,

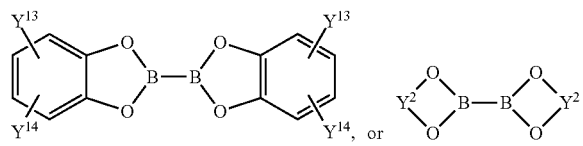

in the presence of a catalyst, such as, for example, [1,1'-bis(diphenylphosphino)ferrocene]dichloropalladium(II), complex $(Pd(Cl)_2(dppf))$, and a base, such as, for example, potassium acetate, in a solvent, such as, for example, dimethyl formamide, dimethyl sulfoxide, dioxane and/or toluene (cf. Prasad Appukkuttan et al., Synlett 8 (2003) 1204), wherein $Y^1$ is independently in each occurrence a $C_1$-$C_{18}$alkylgroup and $Y^2$ is independently in each occurrence a $C_2$-$C_{10}$alkylene group, such as —$CY^3Y^4$—$CY^5Y^6$—, or —$CY^7Y^8$—$CY^9Y^{10}$—$CY^{11}Y^{12}$—, wherein $Y^3, Y^4, Y^5, Y^6, Y^7, Y^8, Y^9, Y^{10}, Y^{11}$ and $Y^{12}$ are independently of each other hydrogen, or a $C_1$-$C_{18}$alkylgroup, especially —$C(CH_3)_2C(CH_3)_2$—, —$C(CH_3)_2CH_2C(CH_3)_2$—, or —$CH_2C(CH_3)_2CH_2$—, and $Y^{13}$ and $Y^{14}$ are independently of each other hydrogen, or a $C_1$-$C_{18}$alkylgroup.

Diboronic acid or diboronate group containing dibenzofurans, dibenzothiophenes and carbazoles can also be prepared by reacting halogenated dibenzofurans, dibenzothiophenes and carbazoles with alkyl lithium reagents, such as, for example, n-butyl lithium, or t-buthyl lithium, followed by reaction with boronic esters, such as, for example, $B(isopropoxy)_3$, $B(methoxy)_3$, or

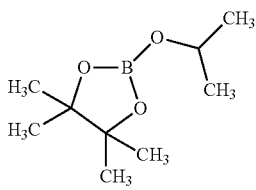

(cf. Synthesis (2000) 442-446). Diboronic acid or diboronate group containing dibenzofurans, dibenzothiophenes and carbazoles can also be prepared by reacting dibenzofurans, dibenzothiophenes and carbazoles with lithium amides, such as, for example, lithium diisopropylamide (LDA) followed by reaction with boronic esters such as, for example, $B(isopropoxy)_3$, $B(methoxy)_3$, or

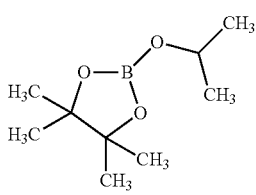

(J. Org. Chem. 73 (2008) 2176-2181).

The synthesis of pyrimidine building blocks is described, for example, in WO2012/080052 (U.S. 61/422,249):

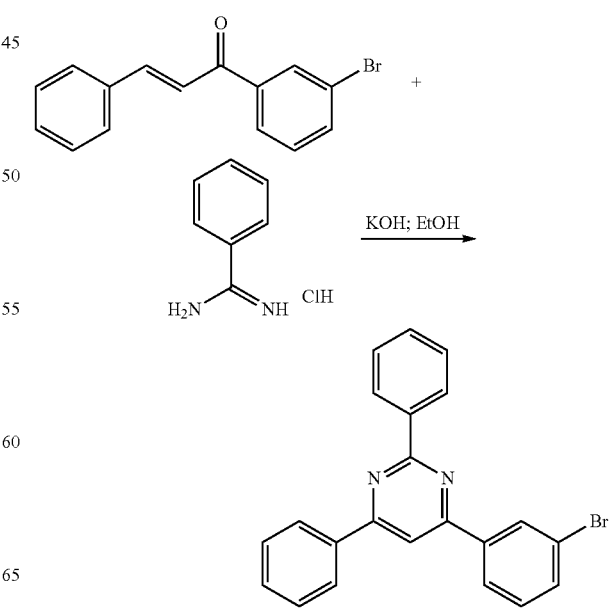

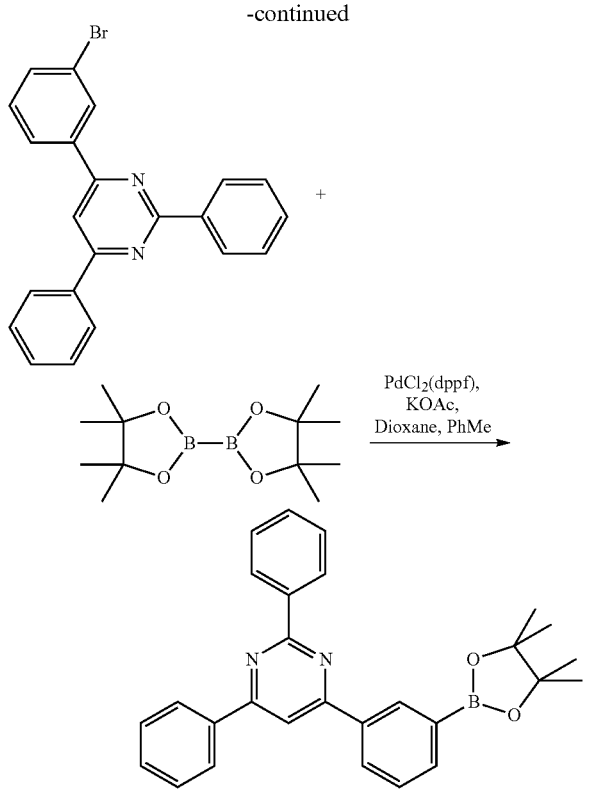

Diboronic acid or diboronate group containing dibenzofurans, dibenzothiophenes and carbazoles, such as, for example,

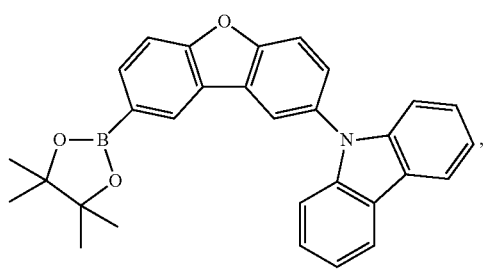 [SMILES: CC1(C)OB(c2ccc3oc4ccc(-n5c6ccccc6c6ccccc65)cc4c3c2)OC1(C)C]

can be reacted with equimolar amounts of halogenated triazines, such as, for example,

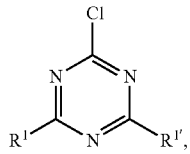

in a solvent and in the presence of a catalyst. The catalyst may be one of the μ-halo(triisopropylphosphine)(η³-allyl)palladium(II) type (see for example WO99/47474).

Preferably, the Suzuki reaction is carried out in the presence of an organic solvent, such as an aromatic hydrocarbon or a usual polar organic solvent, such as benzene, toluene, xylene, tetrahydrofurane, or dioxane, or mixtures thereof, most preferred toluene. Usually, the amount of the solvent is chosen in the range of from 1 to 10 l per mol of boronic acid derivative. Also preferred, the reaction is carried out under an inert atmosphere such as nitrogen, or argon. Further, it is preferred to carry out the reaction in the presence of an aqueous base, such as an alkali metal hydroxide or carbonate such as NaOH, KOH, $Na_2CO_3$, $K_2CO_3$, $Cs_2CO_3$ and the like, preferably an aqueous $K_2CO_3$ solution is chosen. Usually, the molar ratio of the base to boronic acid or boronic ester derivative is chosen in the range of from 0.5:1 to 50:1, very especially 1:1. Generally, the reaction temperature is chosen in the range of from 40 to 180° C., preferably under reflux conditions. Preferred, the reaction time is chosen in the range of from 1 to 80 hours, more preferably from 20 to 72 hours. In a preferred embodiment a usual catalyst for coupling reactions or for polycondensation reactions is used, preferably Pd-based, which is described in WO2007/101820. The palladium compound is added in a ratio of from 1:10000 to 1:50, preferably from 1:5000 to 1:200, based on the number of bonds to be closed. Preference is given, for example, to the use of palladium(II) salts such as $PdAc_2$ or $Pd_2 dba_3$ and to the addition of ligands selected from the group consisting of

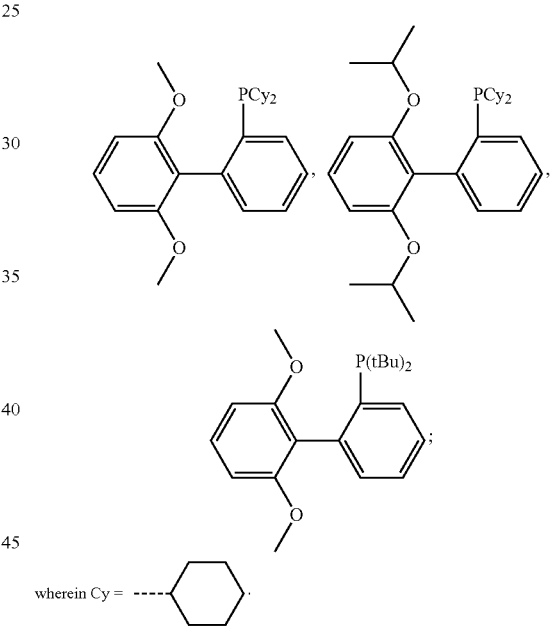

The ligand is added in a ratio of from 1:1 to 1:10, based on Pd. Also preferred, the catalyst is added as in solution or suspension. Preferably, an appropriate organic solvent such as the ones described above, preferably benzene, toluene, xylene, THF, dioxane, more preferably toluene, or mixtures thereof, is used. The amount of solvent usually is chosen in the range of from 1 to 10 l per mol of boronic acid derivative. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, G. Wegner in Macromol. Rapid Commun. 17 (1996) 239-252 and G. A. Molander and B. Canturk, Angew. Chem., 121 (2009) 9404-9425.

A possible synthetic route for compound A-1, or similar compounds is shown in the reaction scheme below:

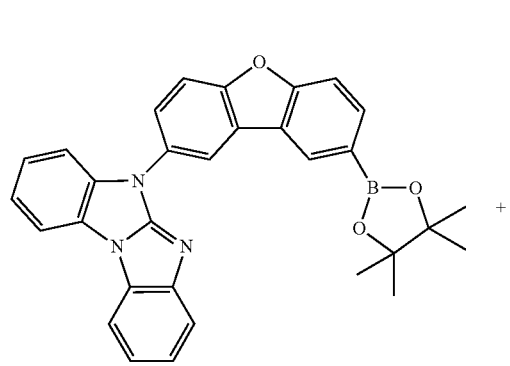

+

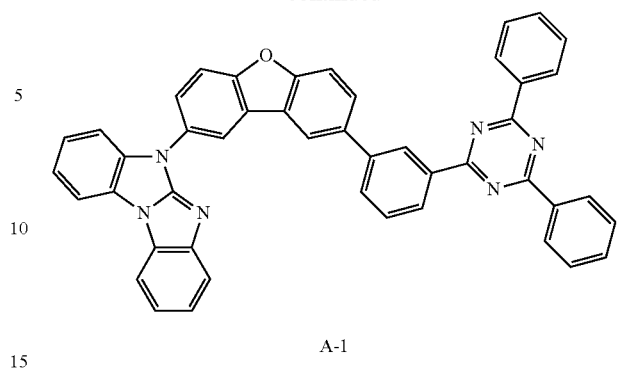

A-1

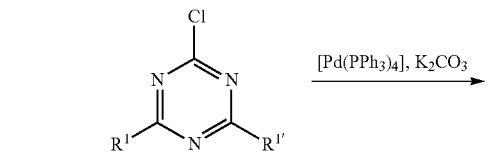

[Pd(PPh₃)₄], K₂CO₃ →

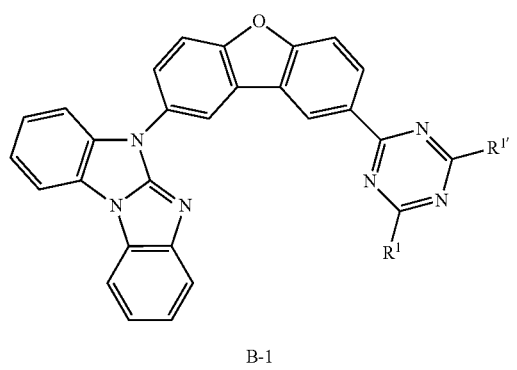

B-1

Reference is made to Lichang Zeng, Thomas Y.-H. Lee, Paul B. Merkel and Shaw H. Chen, J. Mater. Chem. 19 (2009) 8772-8781. The synthesis of 2-(3-bromophenyl)-4,6-diphenyl-1,3,5-triazine is described in WO2011/019156.

A possible synthetic route for compounds B-1 and B-13 is shown in the reaction scheme below:

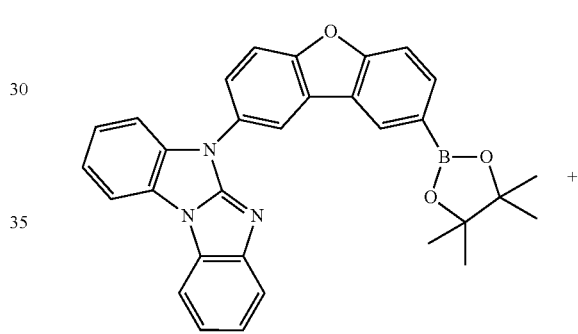

+

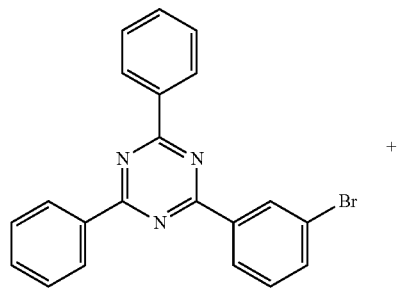

K₃PO₄*H₂O
sPhos,
Pd(OAc)₂
Dioxane,
PhMe

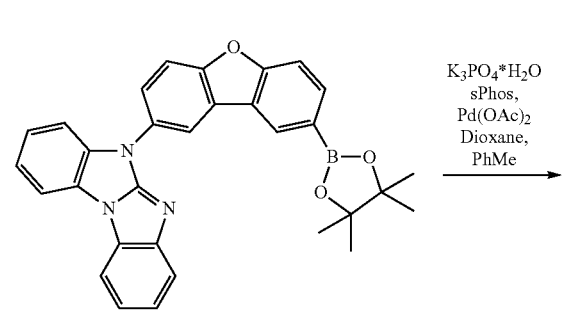

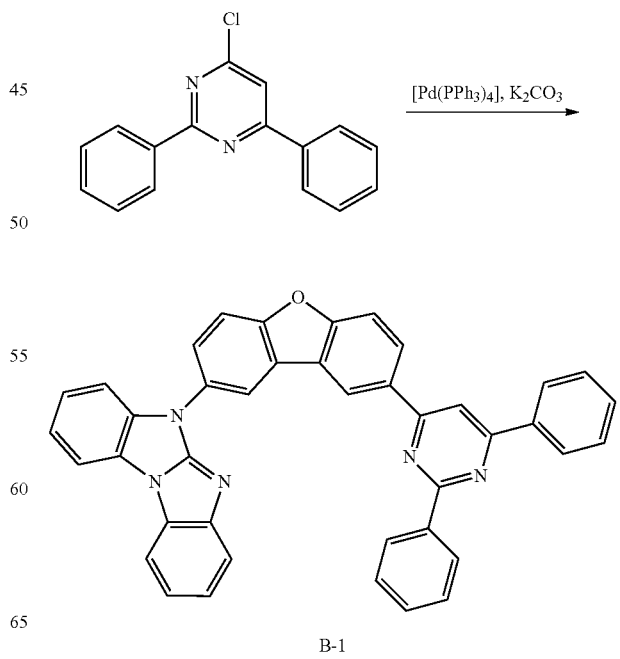

B-1

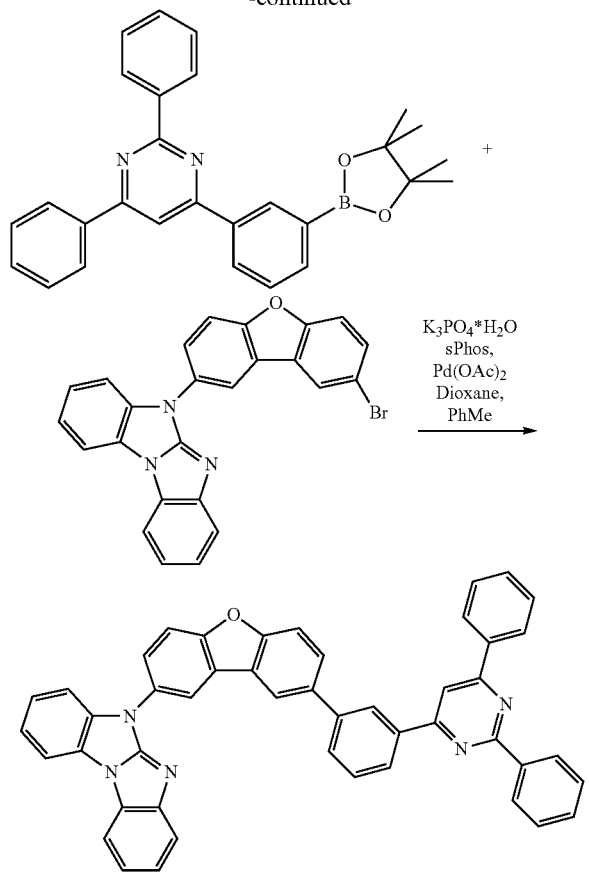

B-13

The synthesis of 4-chloro-2,6-diphenyl-pyrimidine is described in WO05/033084. The synthesis of 4,6-diaryl-2-chloropyrimidines can be done according to, or in analogy to the methods described Journal of Heterocyclic Chemistry 43 (2006) 127-131.

It has been found that the compounds of the formula I are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs), the compounds of the formula I being particularly suitable in OLEDs for use as matrix material in a light-emitting layer and/or as hole/exciton blocker material and/or as electron transport material, especially in combination with a phosphorescence emitter. In the case of use of the inventive compounds of the formula I in OLEDs, OLEDs which have good efficiencies and a long lifetime and which can be operated especially at a low use and operating voltage are obtained. The inventive compounds of the formula I are suitable especially for use as electron transporting, matrix and/or hole/exciton blocker materials for blue and green emitters, for example light blue or deep blue emitters, these being especially phosphorescence emitters. Furthermore, the compounds of the formula I can be used as transport (conductor)/complementary materials in organic electronics applications selected from switching elements and organic solar cells.

In the emission layer or one of the emission layers of an OLED, it is also possible to combine an emitter material with a matrix material of the compound of the formula I and a further matrix material which has, for example, a good hole conductor (hole transport) property. This achieves a high quantum efficiency of this emission layer.

When a compound of the formula I is used as matrix material in an emission layer and additionally as hole/exciton blocker material, owing to the chemical identity or similarity of the materials, an improved interface between the emission layer and the adjacent hole/exciton blocker material is obtained, which can lead to a decrease in the voltage with equal luminance and to an extension of the lifetime of the OLED. Moreover, the use of the same material for hole/exciton blocker material and for the matrix of an emission layer allows the production process of an OLED to be simplified, since the same source can be used for the vapor deposition process of the material of one of the compounds of the formula I.

Suitable structures of organic electronic devices are known to those skilled in the art and are specified below.

The organic transistor generally includes a semiconductor layer formed from an organic layer with hole transport capacity and/or electron transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor.

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or electron transport capacity. In addition, it is possible for further layers known to those skilled in the art to be present in the organic solar cell. The layer with electron transport capacity may comprise the compounds of formula I.

It is likewise possible that the compounds of the formula I are present both in the light-emitting layer (preferably as matrix material) and in the blocking layer for holes (as hole/exciton blockers) and/or as electron transporting material in the electron transporting layer.

The present invention further provides an organic light-emitting diode comprising an anode An and a cathode Ka and a light-emitting layer E arranged between the anode An and the cathode Ka, and if appropriate at least one further layer selected from the group consisting of at least one blocking layer for holes/excitons, at least one blocking layer for electrons/excitons, at least one hole injection layer, at least one hole transport layer, at least one electron injection layer and at least one electron transport layer, wherein the at least one compound of the formula I is present in the light-emitting layer E and/or in at least one of the further layers. The at least one compound of the formula I is preferably present in the light-emitting layer and/or the blocking layer for holes and/or electron transport layer.

Structure of the Inventive OLED

The inventive organic light-emitting diode (OLED) thus generally has the following structure:

an anode (An) and a cathode (Ka) and a light-emitting layer E arranged between the anode (An) and the cathode (Ka).

The inventive OLED may, for example—in a preferred embodiment—be formed from the following layers:
1. Anode
2. Hole transport (conductor) layer
3. Light-emitting layer
4. Blocking layer for holes/excitons
5. Electron transport (conductor) layer
6. Cathode Layer sequences different than the aforementioned structure are also possible, and are known to those skilled in the art. For example, it is possible that the OLED does not have all of the layers mentioned; for example, an OLED with layers (1) (anode), (3) (light-emitting layer) and (6) (cathode) is likewise suitable, in which case the functions of the layers (2) (hole conductor layer) and (4) (blocking layer for holes/excitons) and (5) (electron conductor layer) are assumed by the adjacent layers. OLEDs which have layers (1), (2), (3) and (6), or layers (1), (3), (4), (5) and (6), are likewise suitable. In addition, the OLEDs may have a blocking layer for electrons/excitons between the anode (1) and the hole conductor layer (2).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. For example, a material used in the hole conductor layer, in one embodiment, may simultaneously block excitons and/or electrons.

Furthermore, the individual layers of the OLED among those specified above may in turn be formed from two or more layers. For example, the hole conductor layer may be formed from a layer into which holes are injected from the electrode, and a layer which transports the holes away from the hole-injecting layer into the light-emitting layer. The electron conduction layer may likewise consist of a plurality of layers, for example a layer in which electrons are injected by the electrode, and a layer which receives electrons from the electron injection layer and transports them into the light-emitting layer.

In order to obtain particularly efficient OLEDs, for example, the HOMO (highest occupied molecular orbital) of the hole transport layer should be matched to the work function of the anode, and the LUMO (lowest unoccupied molecular orbital) of the electron transport layer should be matched to the work function of the cathode, provided that the aforementioned layers are present in the inventive OLEDs.

The anode (1) is an electrode which provides positive charge carriers. It may be formed, for example, from materials which comprise a metal, a mixture of various metals, a metal alloy, a metal oxide or a mixture of various metal oxides. Alternatively, the anode may be a conductive polymer. Suitable metals comprise metals and alloys of the metals of the main groups, transition metals and of the lanthanoids, especially the metals of groups Ib, IVa, Va and VIa of the periodic table of the elements, and the transition metals of group VIIIa. When the anode is to be transparent, generally mixed metal oxides of groups IIb, IIIb and IVb of the periodic table of the elements (IUPAC version) are used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed. The material used for the anode (1) is preferably ITO.

Suitable hole transport materials for layer (2) of the inventive OLEDs are disclosed, for example, in Kirk-Othmer Encyclopedia of Chemical Technology, 4th edition, Vol. 18, pages 837 to 860, 1996. Both hole-transporting molecules and polymers can be used as the hole transport material. Hole-transporting molecules typically used are selected from the group consisting of tris[N-(1-naphthyl)-N-(phenylamino)]triphenylamine (1-NaphDATA), 4,4'-bis [N-(1-naphthyl)-N-phenylamino]biphenyl (α-NPD), N,N'-diphenyl-N,N'-bis(3-methyl-phenyl)-[1,1'-biphenyl]-4,4',-diamine (TPD), 1,1-bis[(di-4-tolylamino)phenyl] cyclohexane (TAPC), N,N'-bis(4-methylphenyl)-N,N'-bis (4-ethylphenyl)-[1,1'-(3,3',-dimethyl)-biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino) benzaldehyde diphenylhydrazone (DEH), triphenylamine (TPA), bis[4-(N,N-diethylamino)-2-methyl-phenyl](4-methylphenyl)methane (MPMP), 1-phenyl-3-[p-(diethylamino)styryl]-54p-(diethyl-amino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4''-tris(N,N-diphenylamino) triphenylamine (TDTA), 4,4',4''-tris(N-carbazolyl)-triphenylamine (TCTA), N,N'-bis(naphthalen-2-yl)-N,N'-bis (phenyl)benzidine (β-NPB), N,N'-bis(3-methylphenyl)-N,N'-bis(phenyl)-9,9-spirobifluorene (Spiro-TPD), N,N'-bis (naphthalen-1-yl)-N,N'-bis(phenyl)-9,9-spirobifluorene (Spiro-NPB), N,N'-bis(3-methylphenyl)-N,N'-bis(phenyl)-9,9-dimethylfluorene (DMFL-TPD), di[4-(N,N-ditolylamino)phenyl]cyclohexane, N,N'-bis(naphthalen-1-yl)-N,N'-bis-(phenyl)-9,9-dimethylfluorene, N,N'-bis(naphthalen-1-yl)-N,N'-bis(phenyl)-2,2-dimethyl-benzidine, N,N'-bis (naphthalen-1-yl)-N,N'-bis(phenyl)benzidine, N,N'-bis(3-methyl-phenyl)-N,N'-bis(phenyl)benzidine, 2,3,5,6-tetrafluoro-7,7,8,8-tetracyanoquinodimethane (F4-TCNQ), 4,4',4''-tris(N-3-methylphenyl-N-phenylamino)triphenylamine, 4,4',4''-tris(N-(2-naphthyl)-N-phenyl-amino)triphenylamine, pyrazino[2,3-f][1,10]phenanthroline-2,3-dicarbonitrile (PPDN), N,N,N',N'-tetrakis(4-methoxyphenyl) benzidine (MeO-TPD), 2,7-bis[N,N-bis(4-methoxyphenyl) amino]-9,9-spirobifluorene (MeO-Spiro-TPD), 2,2'-bis[N, N-bis(4-methoxyphenyl)amino]-9,9-spirobifluorene (2,2'-MeO-Spiro-TPD), N,N'-diphenyl-N,N'-di[4-(N,N-ditolylamino)phenyl]benzidine (NTNPB), N,N'-diphenyl-N, N'-di[4-(N,N-diphenylamino)phenyl]benzidine (NPNPB), N,N'-di(naphthalen-2-yl)-N,N'-diphenylbenzene-1,4-diamine ((3-NPP), N,N'-bis(3-methylphenyl)-N,N'-bis(phenyl)-9,9-diphenylfluorene (DPFL-TPD), N,N'-bis(naphthalen-1-yl)-N,N'-bis(phenyl)-9,9-diphenylfluorene (DPFL-NPB), 2,2',7,7'-tetrakis(N,N-diphenylamino)-9,9'-spirobifluorene (Spiro-TAD), 9,9-bis[4-(N,N-bis(biphenyl-4-yl)amino)phenyl]-9H-fluorene (BPAPF), 9,9-bis[4-(N,N-bis(naphthalen-2-yl)amino)phenyl]-9H-fluorene (NPAPF), 9,9-bis[4-(N,N-bis(naphthalen-2-yl)-N,N'-bisphenylamino) phenyl]-9H-fluorene (NPBAPF), 2,2',7,7'-tetrakis[N-naphthalenyl(phenyl)amino]-9,9'-spirobifluorene (Spiro-2NPB), N,N'-bis(phenanthren-9-yl)-N,N'-bis(phenyl)benzidine (PAPB), 2,7-bis[N,N-bis(9,9-spiro-bifluoren-2-yl)amino]-9, 9-spirobifluorene (Spiro-5), 2,2'-bis[N,N-bis(biphenyl-4-yl) amino]-9,9-spirobifluorene (2,2'-Spiro-DBP), 2,2'-bis(N,N-diphenylamino)-9,9-spirobifluorene (Spiro-BPA), 2,2',7,7'-tetra(N,N-ditolyl)aminospirobifluorene (Spiro-TTB), N,N, N',N'-tetranaphthalen-2-ylbenzidine (TNB), porphyrin compounds and phthalocyanines such as copper phthalocyanines and titanium oxide phthalocyanines. Hole-transporting polymers typically used are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

In addition—in one embodiment—it is possible to use carbene complexes as hole transport materials, the band gap of the at least one hole transport material generally being greater than the band gap of the emitter material used. In the context of the present application, "band gap" is understood to mean the triplet energy. Suitable carbene complexes are, for example, carbene complexes as described in WO 2005/019373 A2, WO 2006/056418 A2, WO 2005/113704, WO 2007/115970, WO 2007/115981 and WO 2008/000727. One example of a suitable carbene complex is Ir(dpbic)$_3$ with the formula:

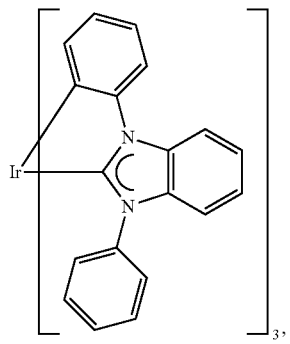

which is disclosed, for example, in WO2005/019373. In principle, it is possible that the hole transport layer comprises at least one compound of the formula I as hole transport material.

The light-emitting layer (3) comprises at least one emitter material. In principle, it may be a fluorescence or phosphorescence emitter, suitable emitter materials being known to those skilled in the art. The at least one emitter material is preferably a phosphorescence emitter. The phosphorescence emitter compounds used with preference are based on metal complexes, and especially the complexes of the metals Ru, Rh, Ir, Pd and Pt, in particular the complexes of Ir, have gained significance. The compounds of the formula I can be used as the matrix in the light-emitting layer.

Suitable metal complexes for use in the inventive OLEDs are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981, WO 2008/000727, WO2010129323, WO2010056669 and WO10086089.

Further suitable metal complexes are the commercially available metal complexes tris(2-phenylpyridine)iridium (III), iridium(III) tris(2-(4-tolyl)pyridinato-N,C$^{2'}$), bis(2-phenylpyridine)(acetylacetonato)iridium(III), iridium(III) tris(1-phenylisoquinoline), iridium(III) bis(2,2'-benzothienyl)pyridinato-N,C$^{3'}$) (acetylacetonate), tris(2-phenylquinoline)iridium(III), iridium(III) bis(2-(4,6-difluorophenyl)-pyridinato-N,C$^{2}$)picolinate, iridium(III) bis(1-phenylisoquinoline)(acetylacetonate), bis(2-phenylquinoline)(acetylacetonato)iridium(III), iridium(III) bis(di-benzo[f,h]quinoxaline)(acetylacetonate), iridium(III) bis(2-methyldi-benzo[f,h]quinoxaline)(acetylacetonate) and tris(3-methyl-1-phenyl-4-trimethylacetyl-5-pyrazolino)terbium(III), bis[1-(9,9-dimethyl-9H-fluoren-2-yl)isoquinoline](acetylacetonato)iridium(III), bis(2-phenylbenzothiazolato)(acetylacetonato)iridium(III), bis(2-(9,9-dihexylfluorenyl)-1-pyridine)(acetylacetonato)iridium(III), bis(2-benzo[b]thiophen-2-yl-pyridine)(acetylacetonato) iridium(III).

In addition, the following commercially available materials are suitable: tris(dibenzoyl-acetonato)mono(phenanthroline)europium(III), tris(dibenzoylmethane)-mono (phenanthroline)europium(III), tris(dibenzoylmethane) mono(5-aminophenanthroline)europium(III), tris(di-2-naphthoylmethane)mono(phenanthroline)europium(III), tris (4-bromobenzoyl-methane)mono(phenanthroline)europium (III), tris(di(biphenyl)methane)-mono(phenanthroline) europium(III), tris(dibenzoylmethane)mono(4,7-diphenyl-phenanthroline)europium(III), tris(dibenzoylmethane)mono (4,7-di-methyl-phenanthroline)europium(III), tris (dibenzoylmethane)mono(4,7-dimethylphenanthrolinedisulfonic acid)europium(III) disodium salt, tris[di (4-(2-(2-ethoxyethoxy)ethoxy)-benzoylmethane)]mono (phenanthroline)europium(III) and tris[d][4-(2-(2-ethoxyethoxy)ethoxy)benzoylmethane)]mono(5-aminophenanthroline)europium(III), osmium(II) bis(3-(trifluoromethyl)-5-(4-tert-butylpyridyl)-1,2,4-triazolato) diphenylmethylphosphine, osmium(II) bis(3-(trifluoromethyl)-5-(2-pyridyl)-1,2,4-triazole) dimethylphenylphosphine, osmium(II) bis(3-(trifluoromethyl)-5-(4-tert-butylpyridyl)-1,2,4-triazolato) dimethylphenylphosphine, osmium(II) bis(3-(trifluoromethyl)-5-(2-pyridyl)-pyrazolato) dimethylphenylphosphine, tris[4,4'-di-tert-butyl(2,2)-bipyridine]ruthenium(III), osmium(II) bis(2-(9,9-dibutylfluorenyl)-1-isoquinoline(acetylacetonate).

The light emitting layer comprises preferably a compound of the formula

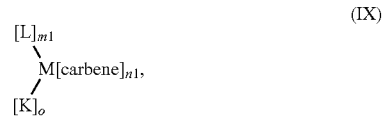

which are described in WO 2005/019373 A2, wherein the symbols have the following meanings:
M is a metal atom selected from the group consisting of Co, Rh, Ir, Nb, Pd, Pt, Fe, Ru, Os, Cr, Mo, W, Mn, Tc, Re, Cu, Ag and Au in any oxidation state possible for the respective metal atom;
Carbene is a carbene ligand which may be uncharged or monoanionic and monodentate, bidentate or tridentate, with the carbene ligand also being able to be a biscarbene or triscarbene ligand;
L is a monoanionic or dianionic ligand, which may be monodentate or bidentate;
K is an uncharged monodentate or bidentate ligand selected from the group consisting of phosphines; phosphonates and derivatives thereof, arsenates and derivatives thereof; phosphites; CO; pyridines; nitriles and conjugated dienes which form a π complex with $M^1$;

n1 is the number of carbene ligands, where n1 is at least 1 and when n1>1 the carbene ligands in the complex of the formula I can be identical or different;

m1 is the number of ligands L, where m1 can be 0 or ≥1 and when m1>1 the ligands L can be identical or different;

o is the number of ligands K, where o can be 0 or ≥1 and when o>1 the ligands K can be identical or different;

where the sum n1+m1+o is dependent on the oxidation state and coordination number of the metal atom and on the denticity of the ligands carbene, L and K and also on the charge on the ligands, carbene and L, with the proviso that n1 is at least 1.

Carbene complexes which are suitable triplet emitters are described, for example, in WO2006/056418A2, WO2005/113704, WO2007/115970, WO2007/115981, WO2008/000727, WO2009050281, WO2009050290, WO2011051404 and WO2011073149. More preferred are metal-carbene complexes of the general formula

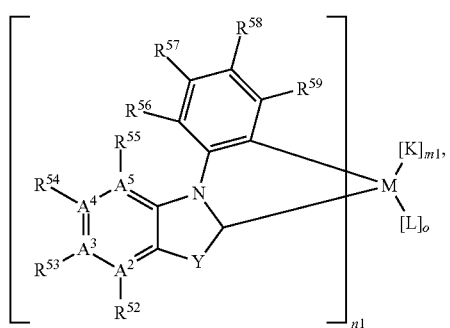

(IXa)

which are described in WO2011/073149, where M, n1, Y, $A^2$, $A^3$, $A^4$, $A^5$, $R^{51}$, $R^{52}$, $R^{53}$, $R^{54}$, $R^{55}$, $R^{56}$, $R^{57}$, $R^{58}$, $R^{59}$, K, L, m1 and o are each defined as follows:

M is Ir, or Pt, n1 is an integer selected from 1, 2 and 3,

Y is $NR^{51}$, O, S or $C(R^{25})_2$, $A^2$, $A^3$, $A^4$, and $A^5$ are each independently N or C, where 2 A=nitrogen atoms and at least one carbon atom is present between two nitrogen atoms in the ring, $R^{51}$ is a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, $R^{52}$, $R^{53}$, $R^{54}$ and $R^{55}$ are each, if $A^2$, $A^3$, $A^4$ and/or $A^5$ is N, a free electron pair, or, if $A^2$, $A^3$, $A^4$ and/or $A^5$ is C, each independently hydrogen, linear or branched alkyl radical optionally interrupted by at least one heteroatom, optionally bearing at least one functional group and having 1 to 20 carbon atoms, cycloalkyl radical optionally interrupted by at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{53}$ and $R^{54}$ together with $A^3$ and $A^4$ form an optionally substituted, unsaturated ring optionally interrupted by at least one further heteroatom and having a total of 5 to 18 carbon atoms and/or heteroatoms, $R^{56}$, $R^{57}$, $R^{58}$ and $R^{59}$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{56}$ and $R^{57}$, $R^{57}$ and $R^{58}$ or $R^{58}$ and $R^{59}$, together with the carbon atoms to which they are bonded, form a saturated, unsaturated or aromatic, optionally substituted ring optionally interrupted by at least one heteroatom and having a total of 5 to 18 carbon atoms and/or heteroatoms, and/or if $A^5$ is C, $R^{55}$ and $R^{56}$ together form a saturated or unsaturated, linear or branched bridge optionally comprising heteroatoms, an aromatic unit, heteroaromatic unit and/or functional groups and having a total of 1 to 30 carbon atoms and/or heteroatoms, to which is optionally fused a substituted or unsubstituted, five- to eight-membered ring comprising carbon atoms and/or heteroatoms, $R^{25}$ is independently a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, K is an uncharged mono- or bidentate ligand, L is a mono- or dianionic ligand, preferably monoanionic ligand, which may be mono- or bidentate, m1 is 0, 1 or 2, where, when m1 is 2, the K ligands may be the same or different, o is 0, 1 or 2, where, when o is 2, the L ligands may be the same or different.

The compound of formula IX is preferably a compound of the formula:
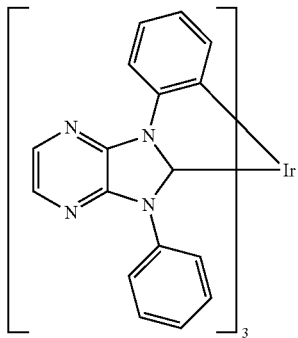
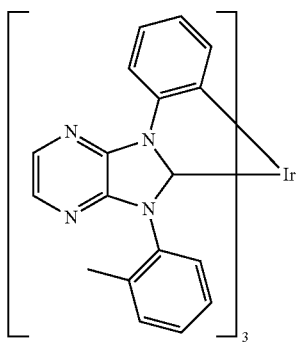
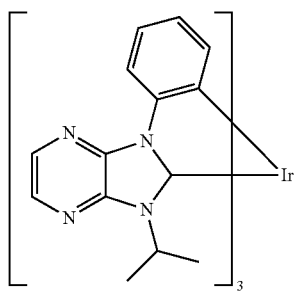
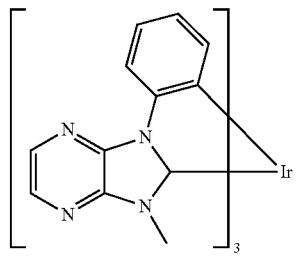
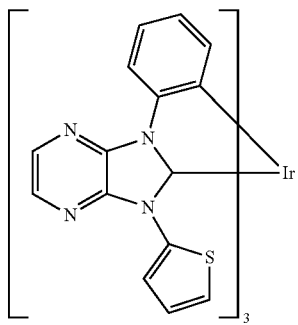
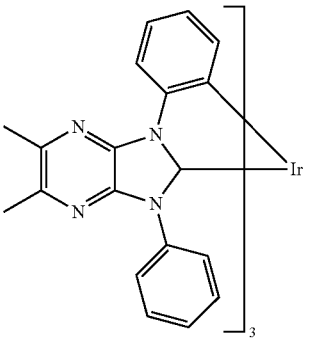
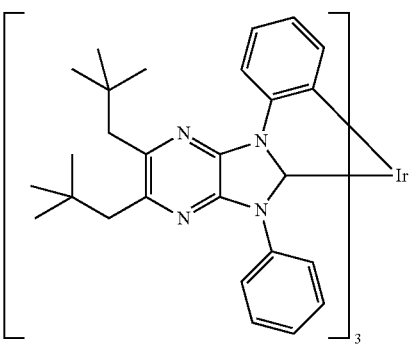
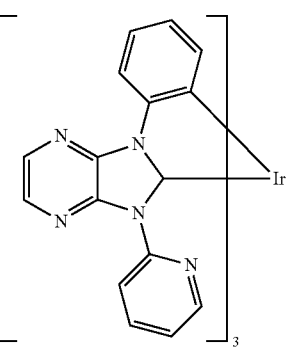
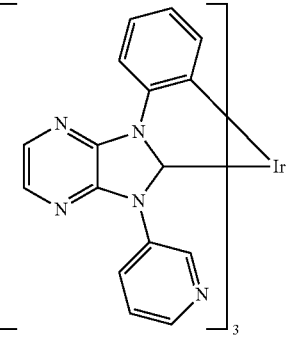
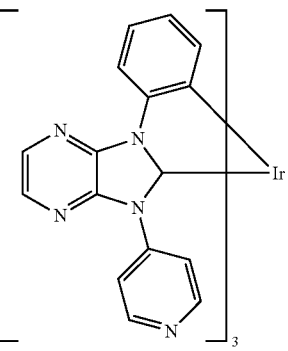

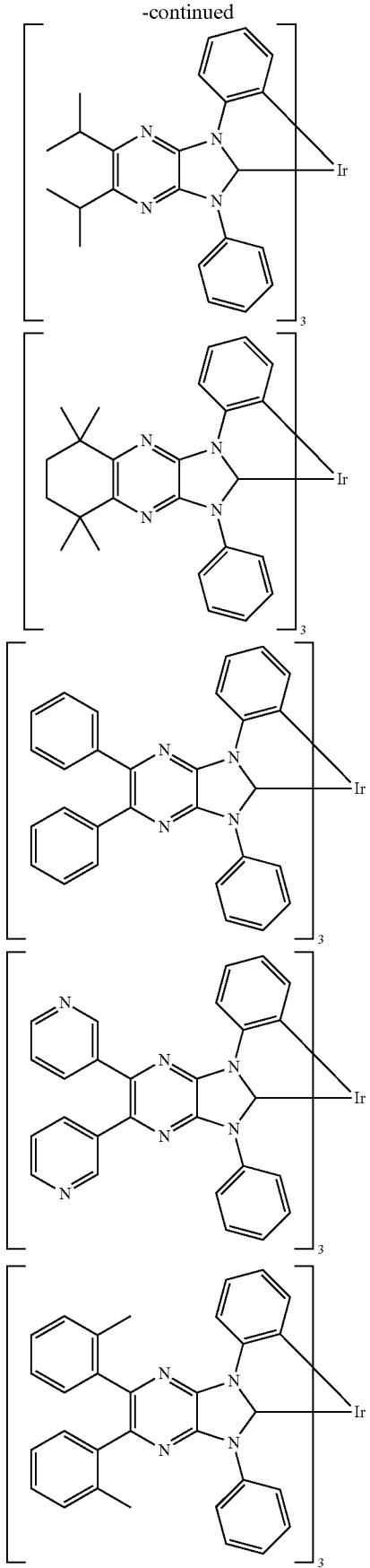
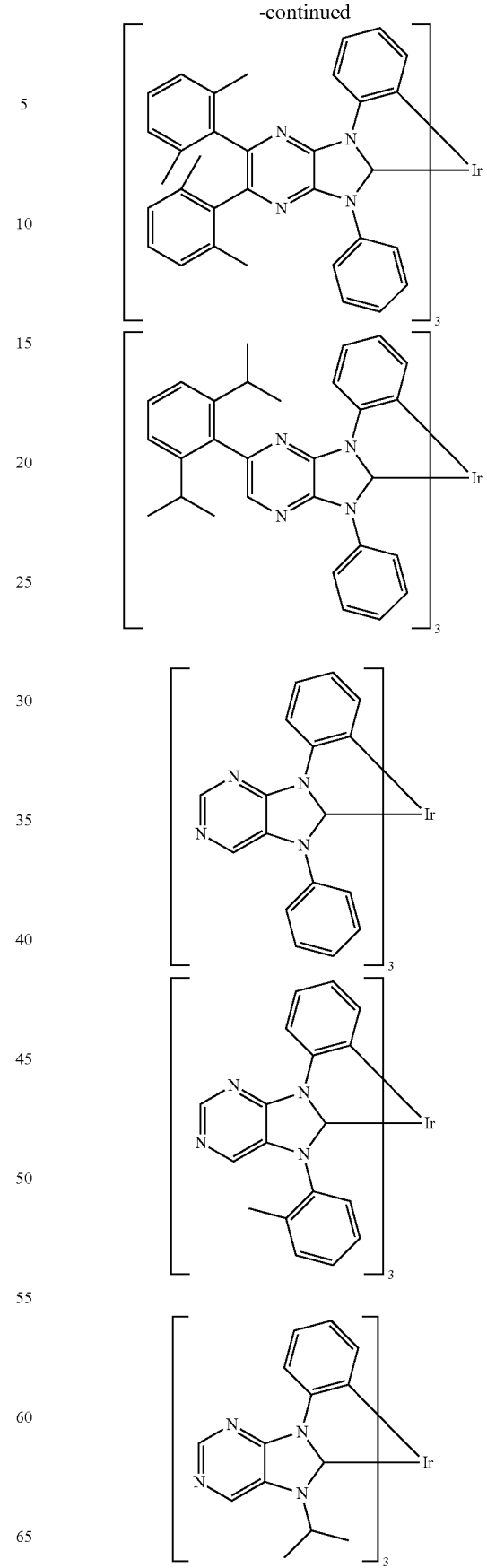

55
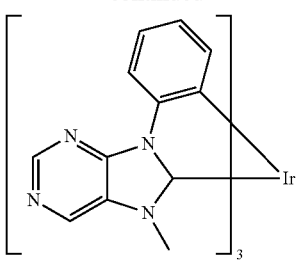
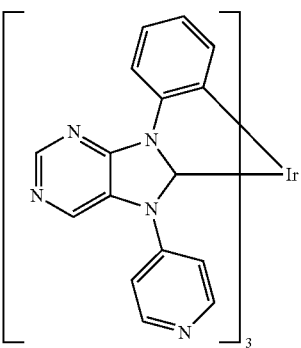
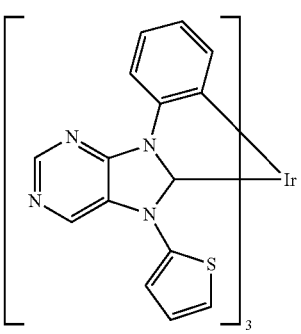
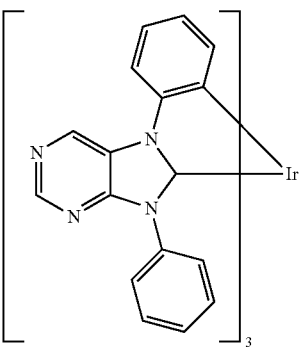
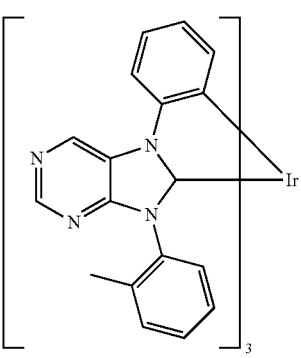
56
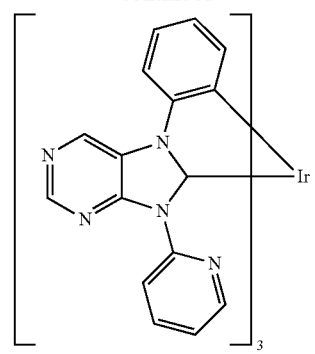
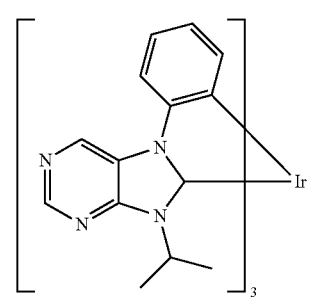
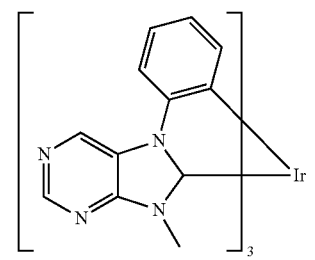
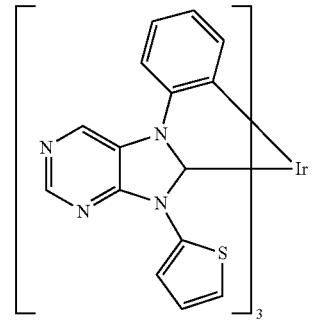
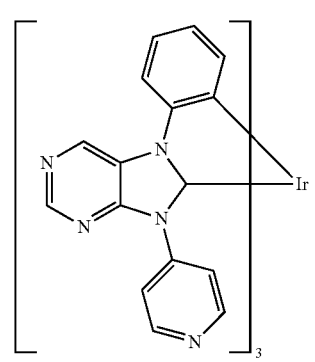

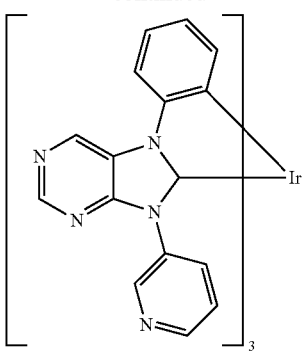
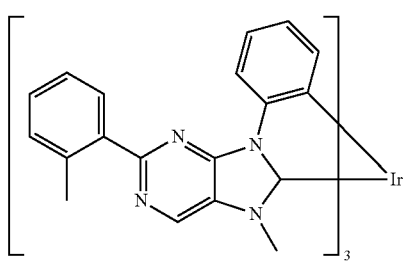
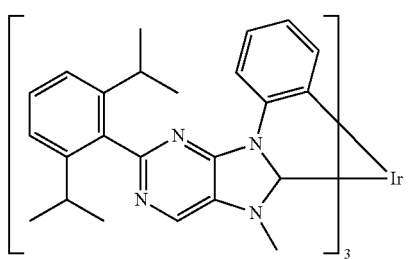
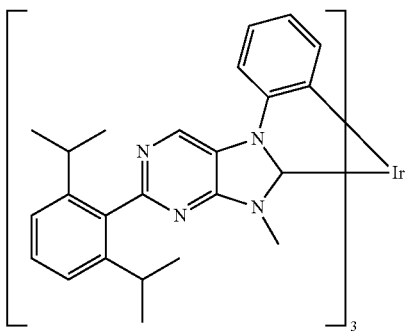
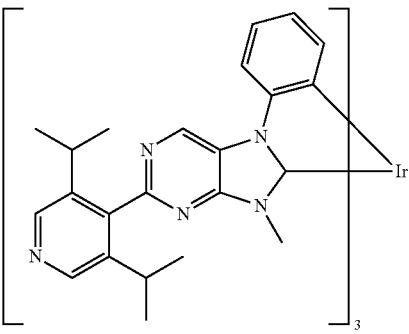
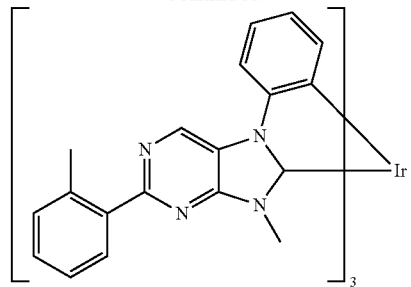
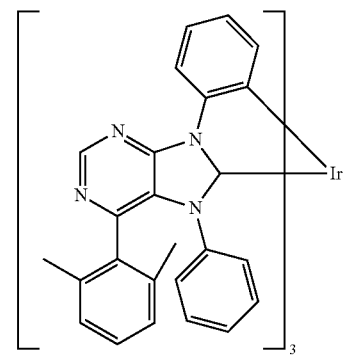
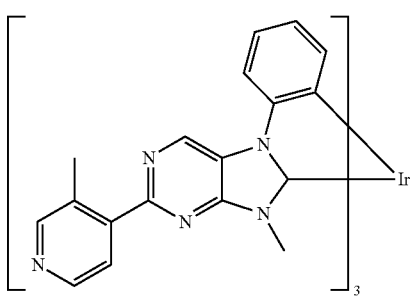
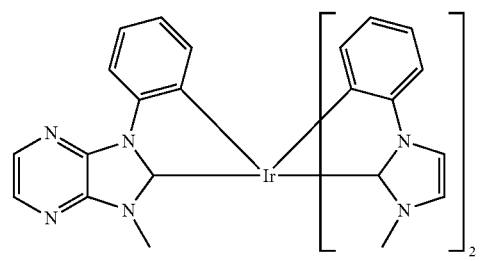
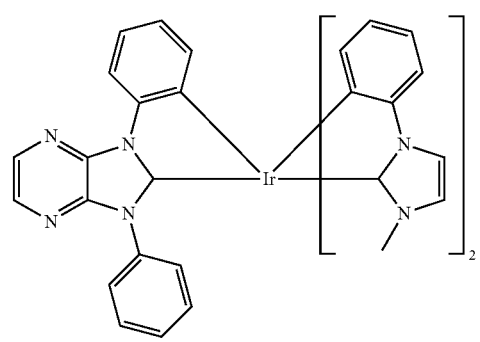

-continued
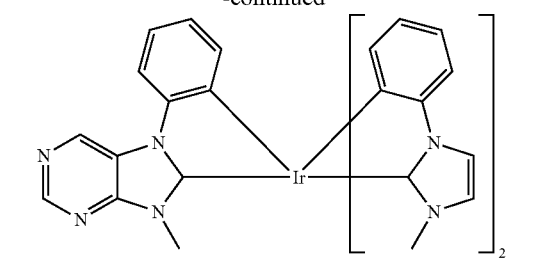
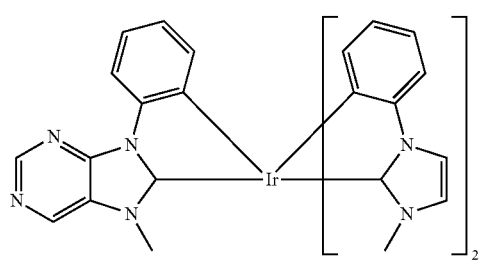
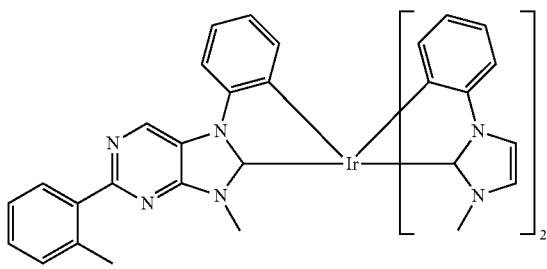
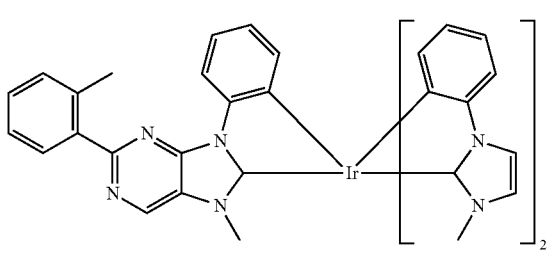
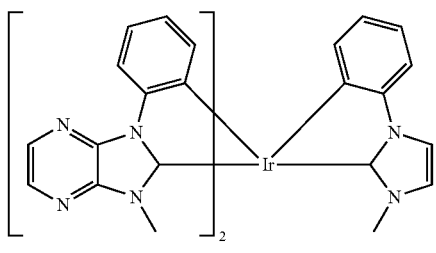
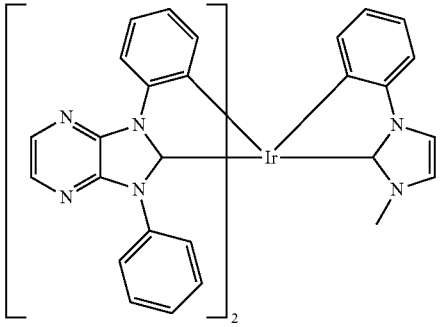
-continued
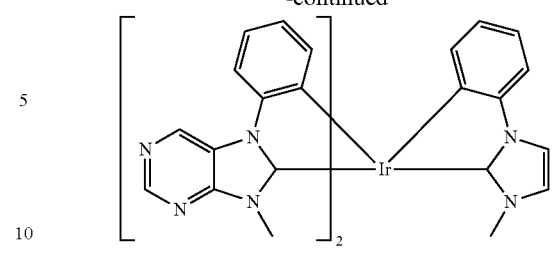
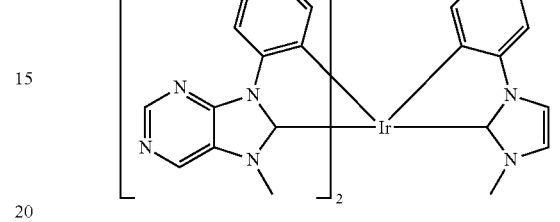
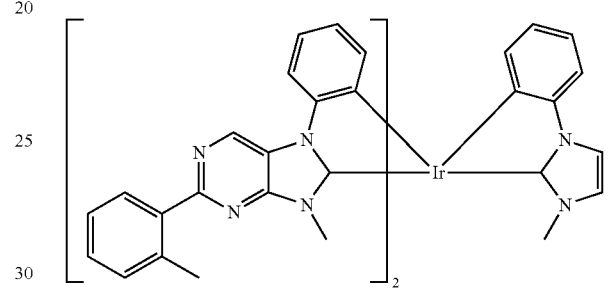
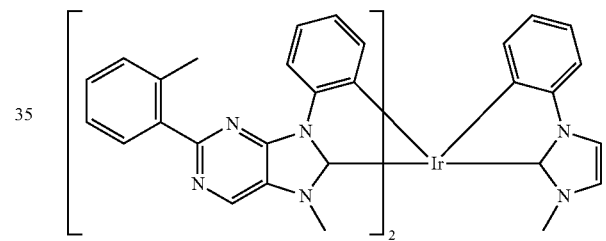
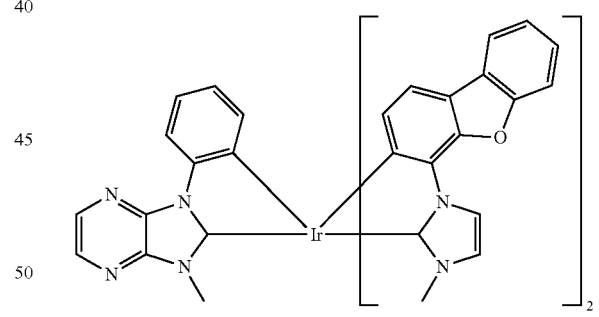
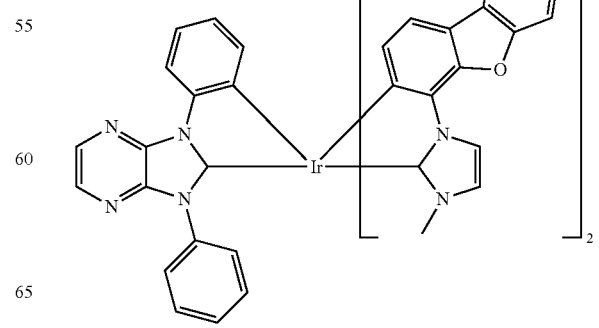

-continued
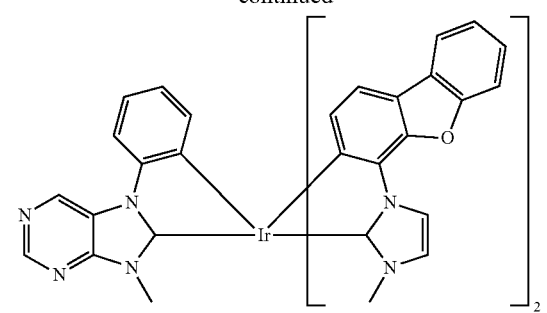
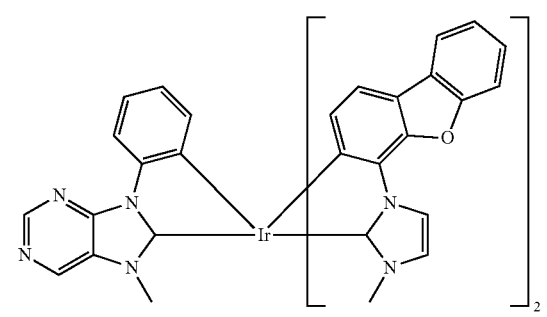
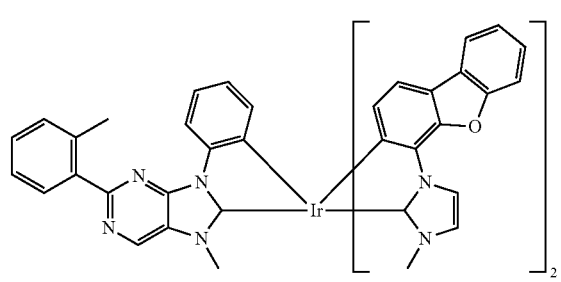
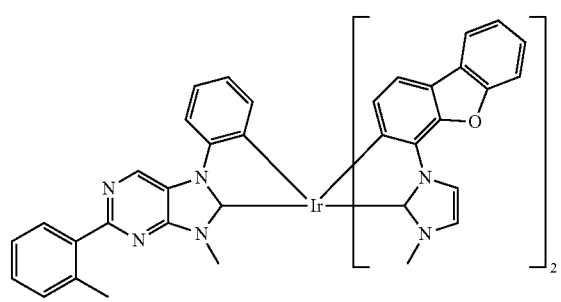
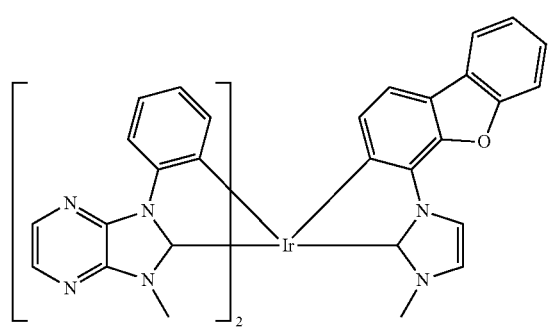
-continued
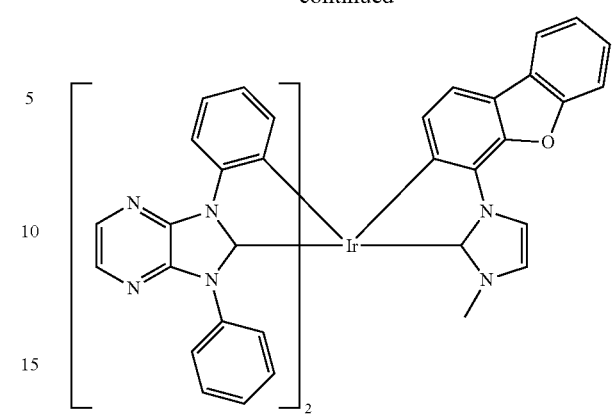
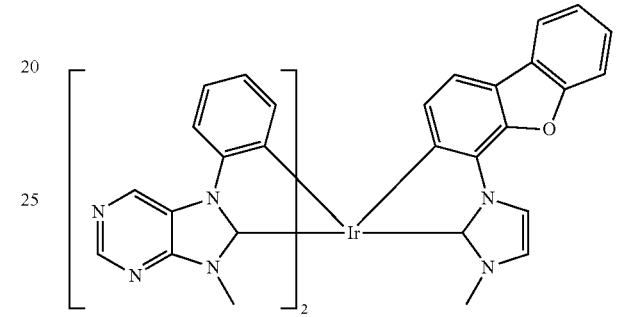
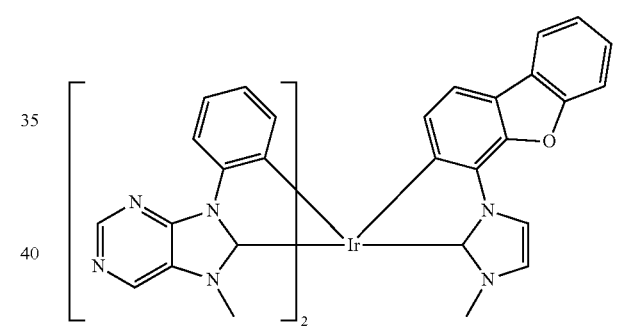
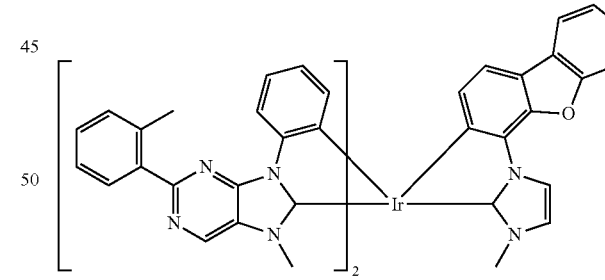
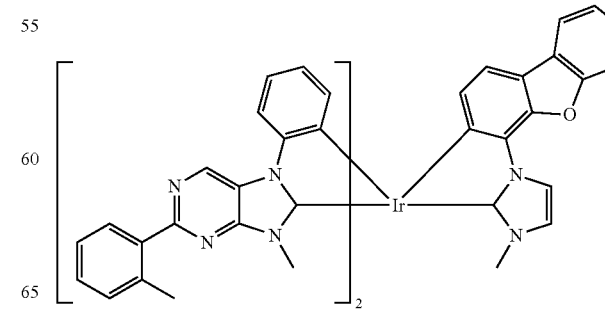

-continued
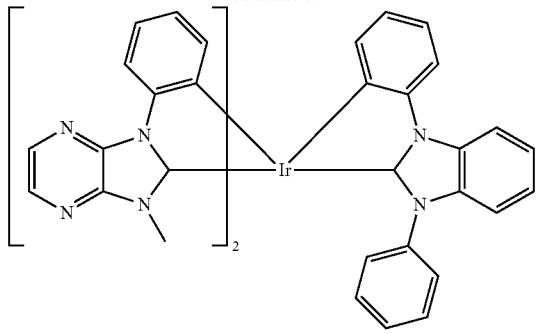
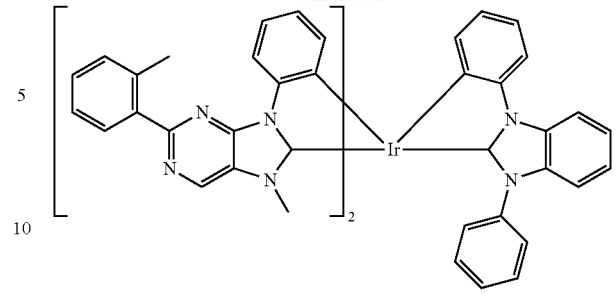
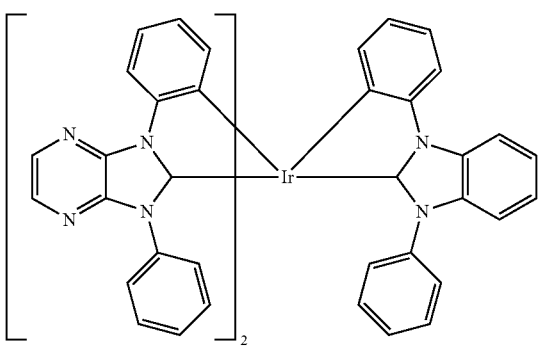
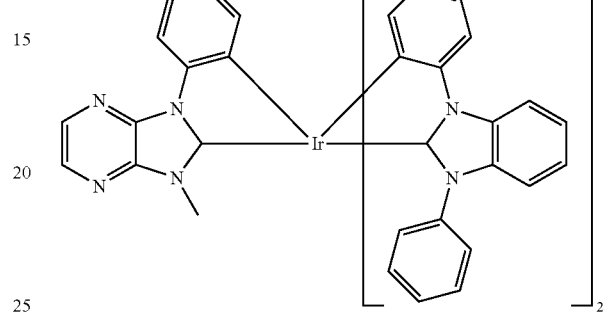
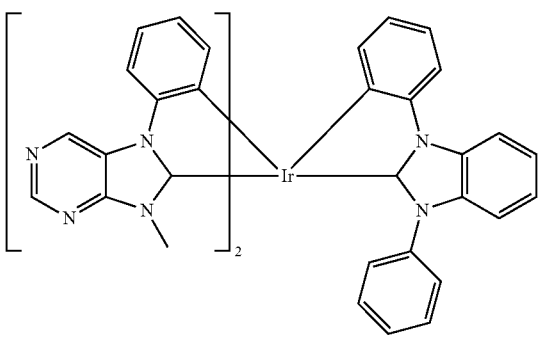
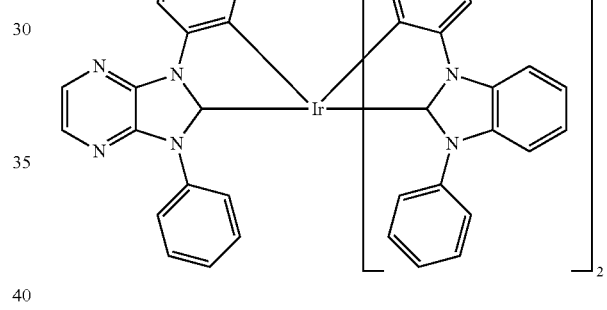
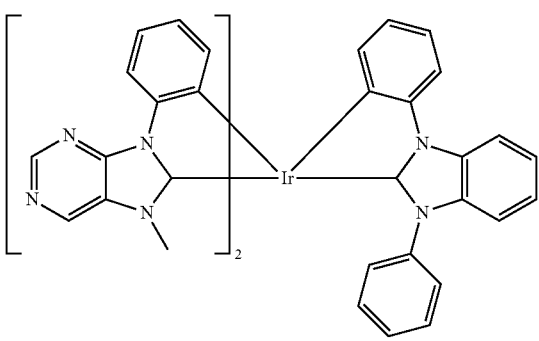
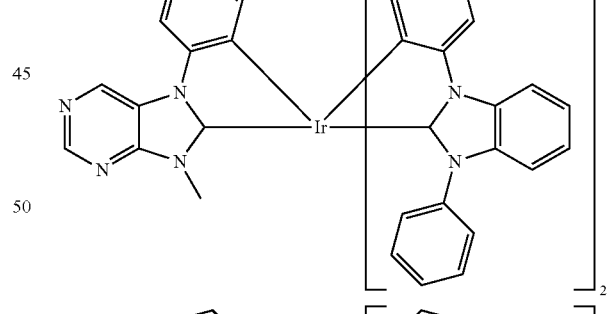
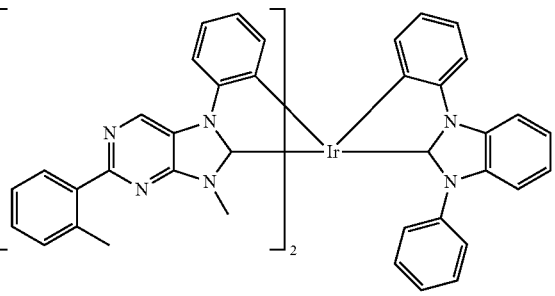
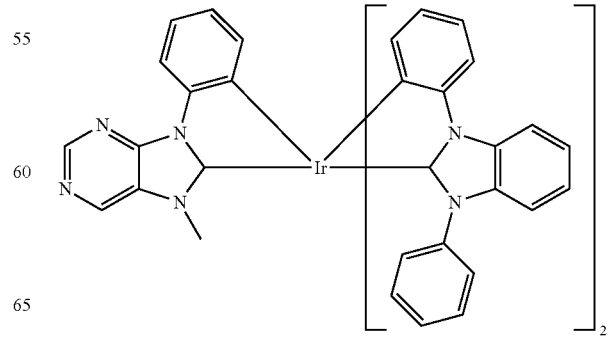

65
-continued
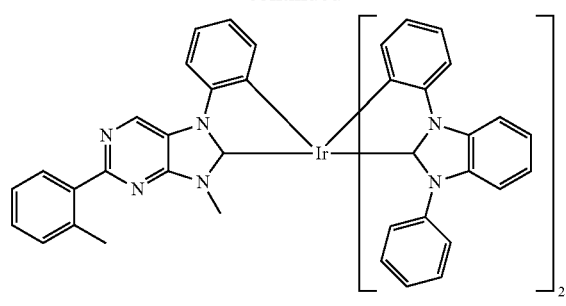
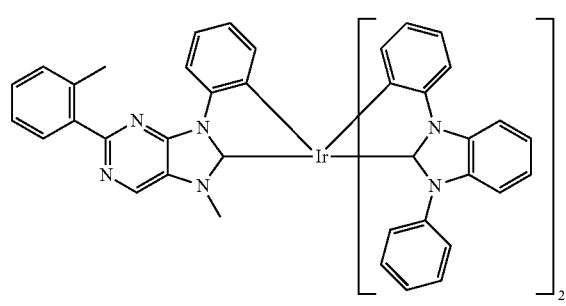
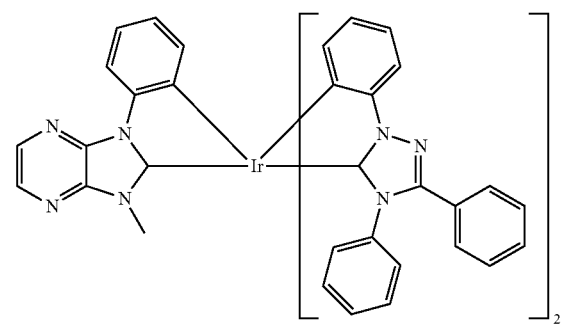
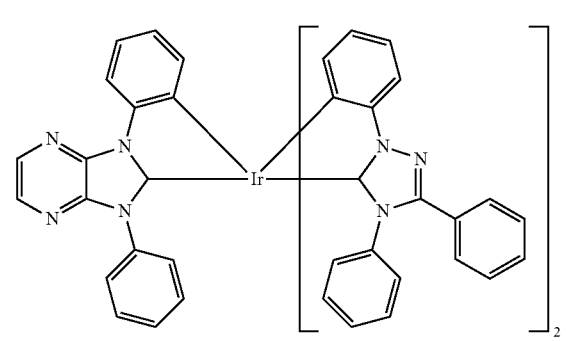
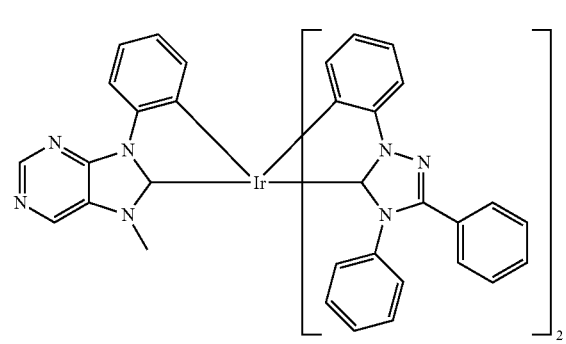
66
-continued
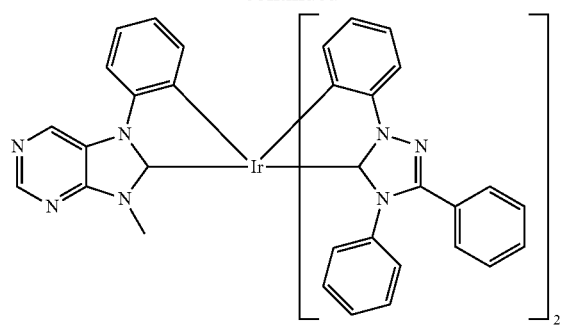
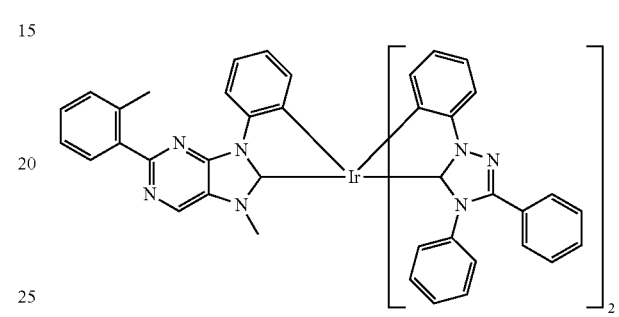
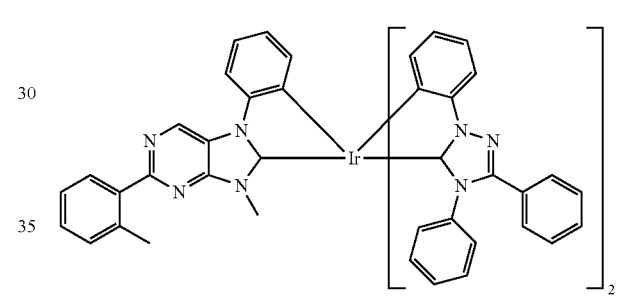
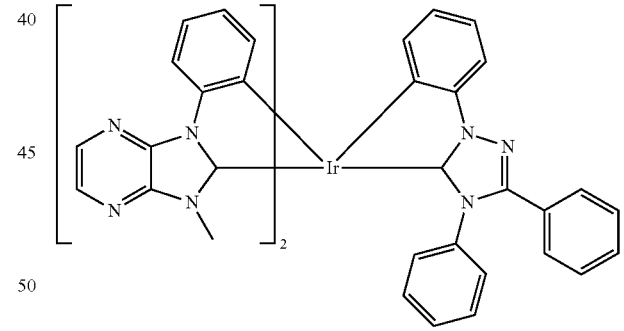
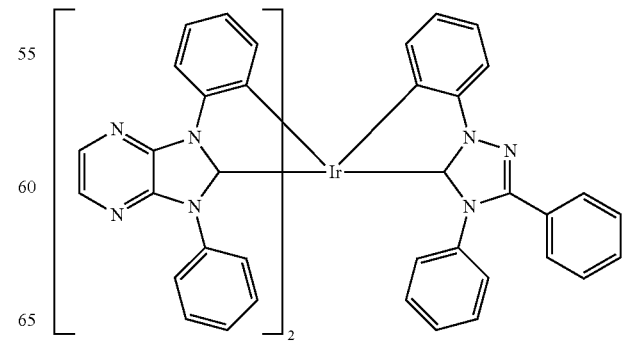

67
-continued
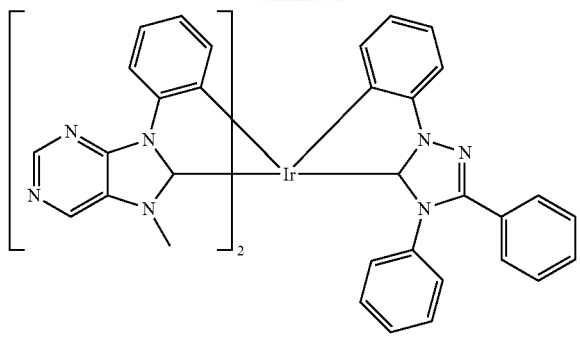
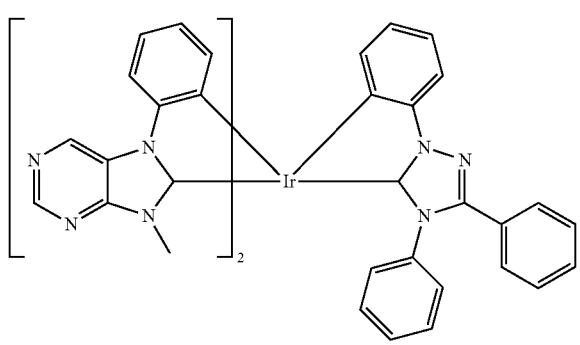
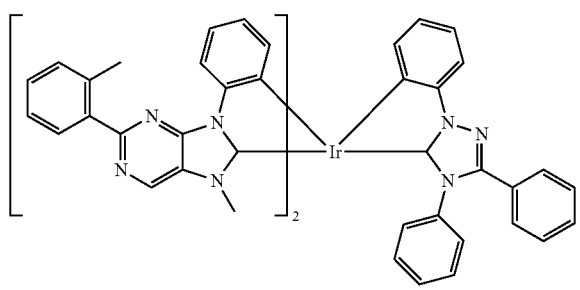
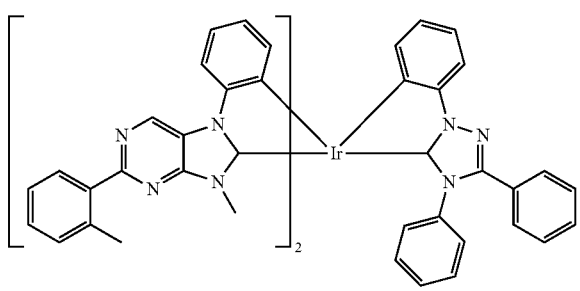
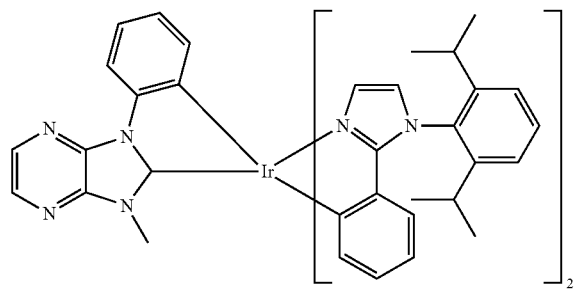
68
-continued
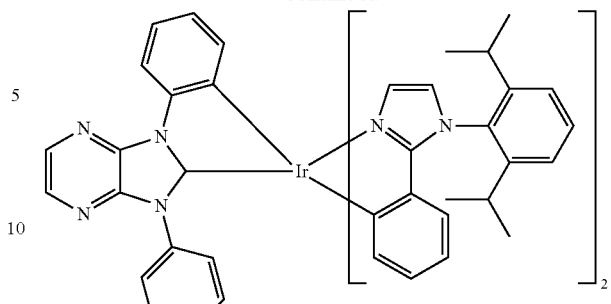
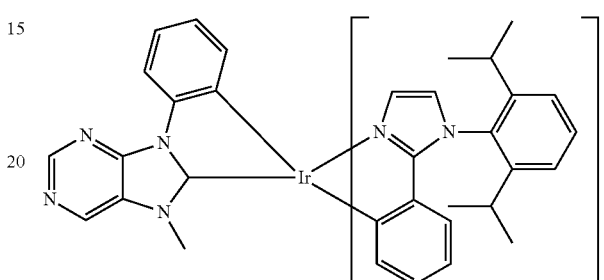
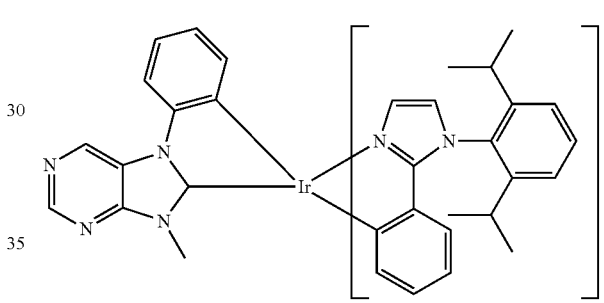
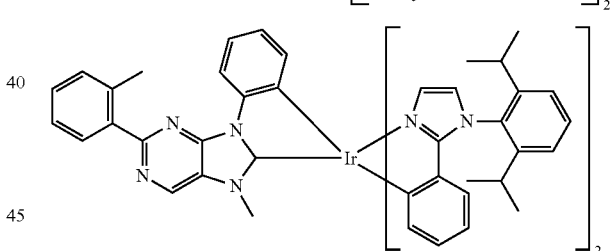
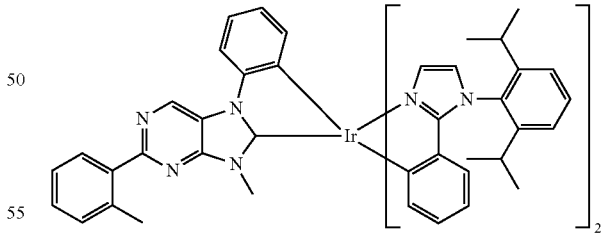
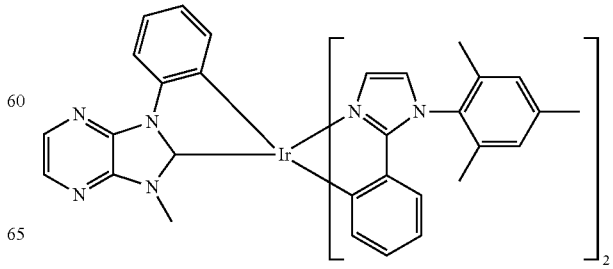

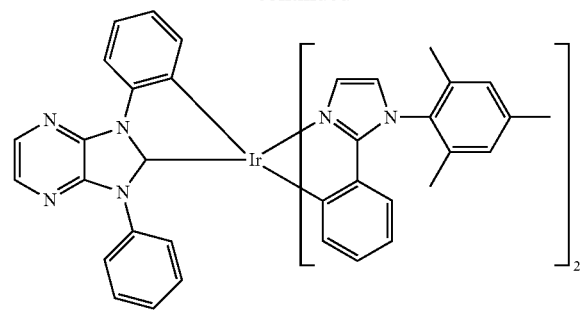
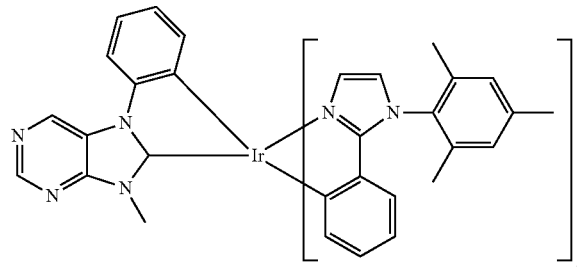
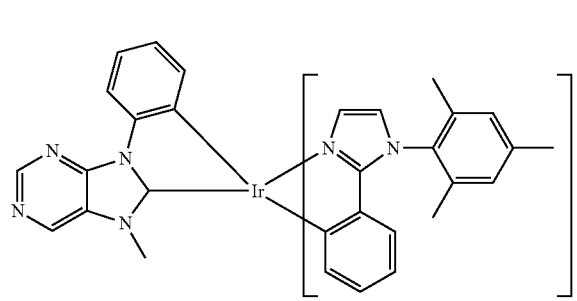
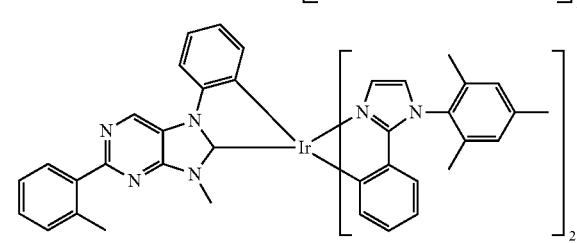
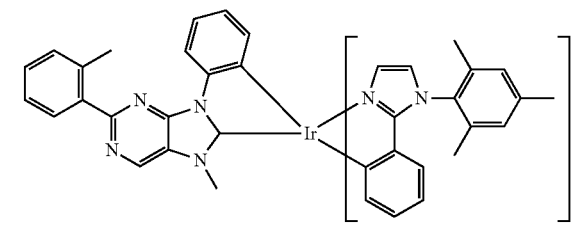
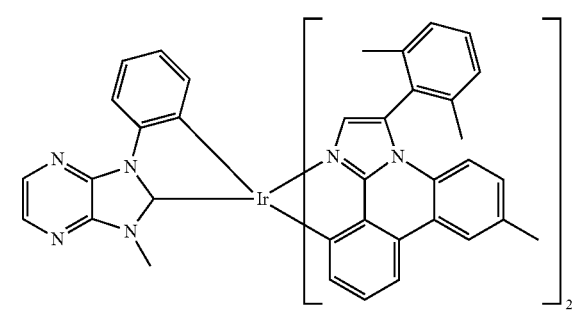
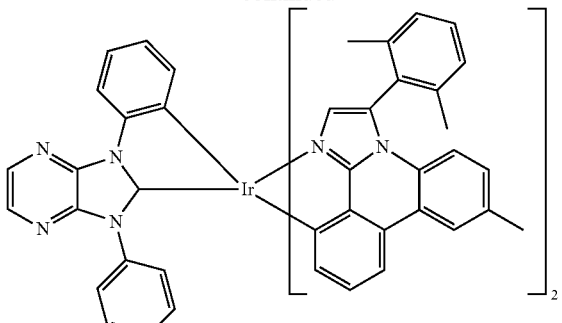
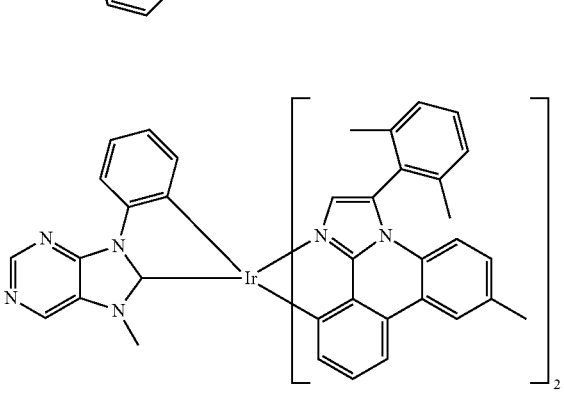
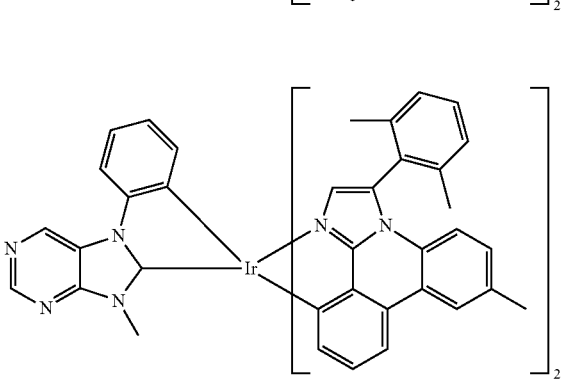
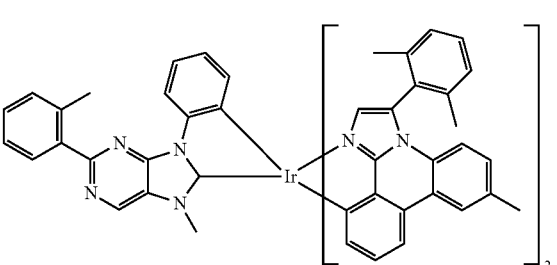
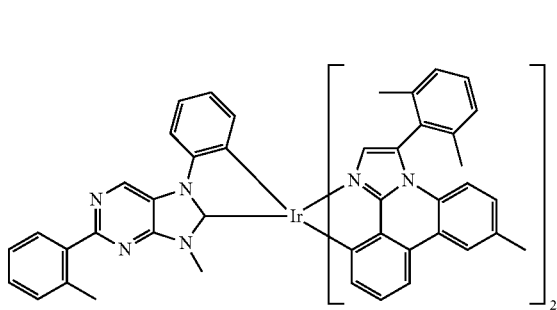

-continued
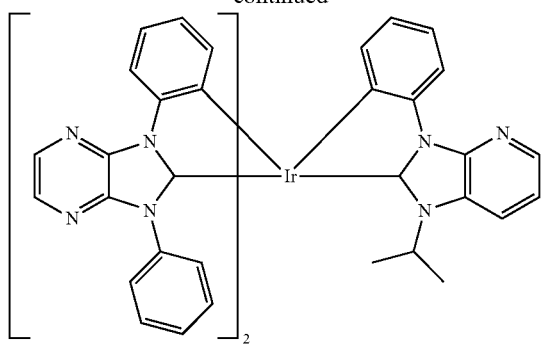
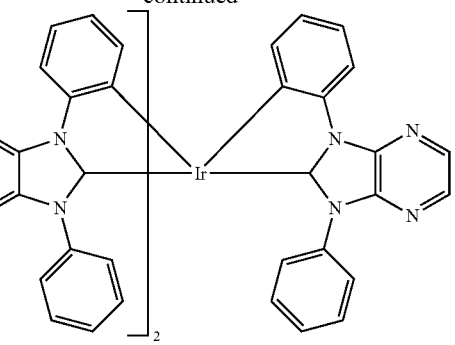
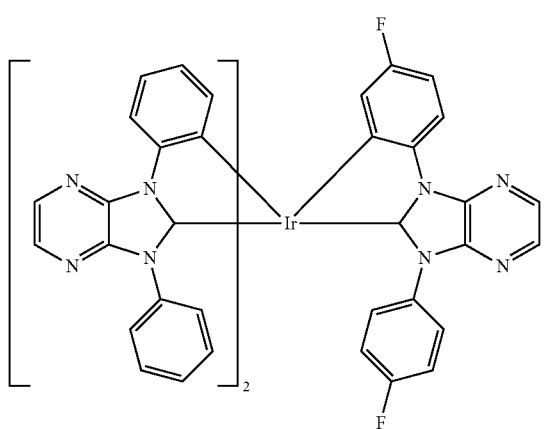
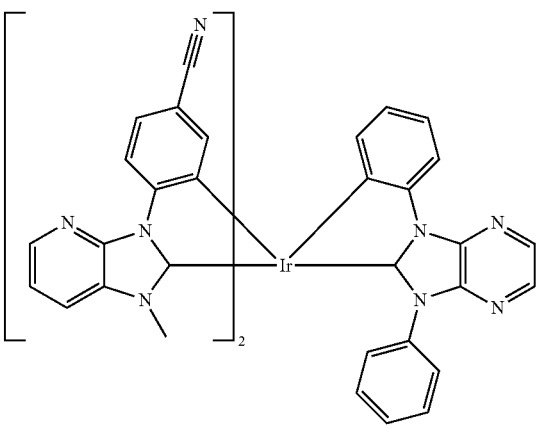
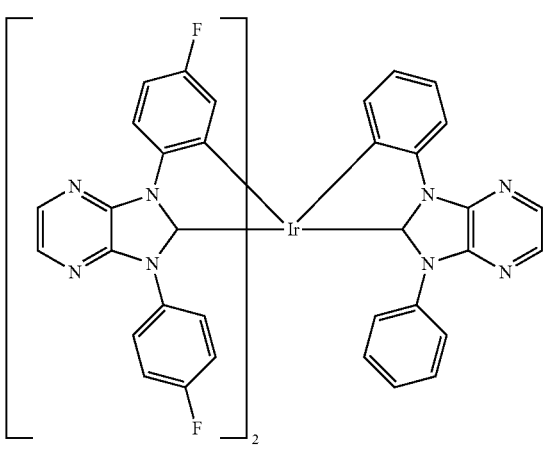
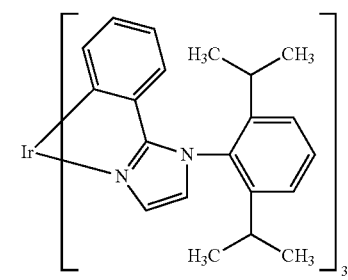
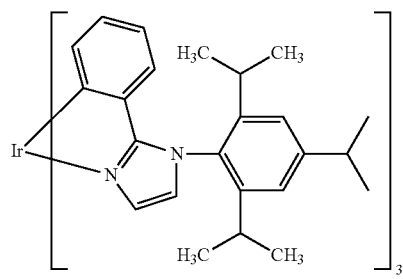
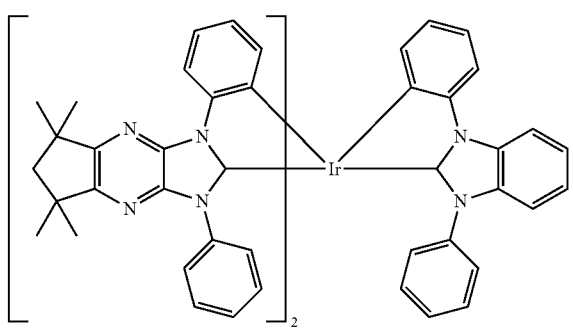
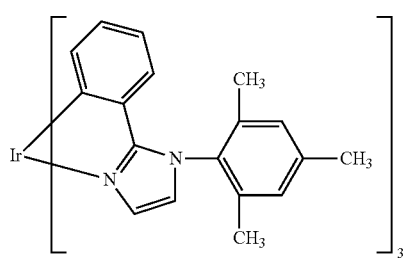

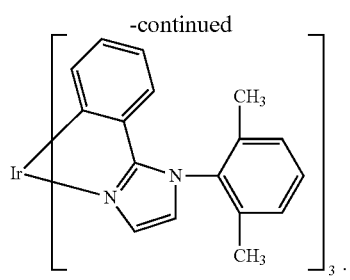

The homoleptic metal-carbene complexes may be present in the form of facial or meridional isomers, preference being given to the facial isomers.

In the case of the heteroleptic metal-carbene complexes, four different isomers may be present, preference being given to the pseudo-facial isomers.

The light-emitting layer may comprise further components in addition to the emitter material. For example, a fluorescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, be a small molecule, for example 4,4'-N,N'-dicarbazolebiphenyl (CDP=CBP) or tertiary aromatic amines, for example TCTA. In a preferred embodiment of the present invention, at least one compound of the formula I is used as matrix material.

In one embodiment of the present invention, the compounds of the formula X are used in the light-emitting layer as matrix material together with carbene complexes as triplet emitters.

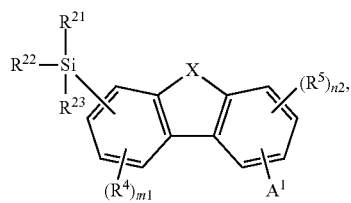

wherein
X is NR, S, O or PR;
R is aryl, heteroaryl, alkyl, cycloalkyl, or heterocycloalkyl;
$A^1$ is —$NR^6R^7$, —$P(O)R^8R^9$, —$S(O)_2R^{12}$, —$S(O)R^{13}$, —$SR^{14}$, or —$OR^{16}$;

$R^{21}$, $R^{22}$ and $R^{23}$ are independently of each other aryl, heteroaryl, alkyl, cycloalkyl, or heterocycloalkyl, wherein at least on of the groups $R^1$, $R^2$, or $R^3$ is aryl, or heteroaryl;
$R^4$ and $R^5$ are independently of each other alkyl, cycloalkyl, heterocycloalkyl, aryl, heteroaryl, a group $A^1$, or a group having donor, or acceptor characteristics;
n2 and m1 are independently of each other 0, 1, 2, or 3;
$R^6$, $R^7$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and
$R^8$, $R^9$, $R^{10}$, $R^{11}$, $R^{12}$, $R^{13}$, $R^{14}$ and $R^{15}$ are independently of each other aryl, heteroaryl, alkyl, cycloalkyl, or heterocycloalkyl. Compounds of formula X, such as, for example,

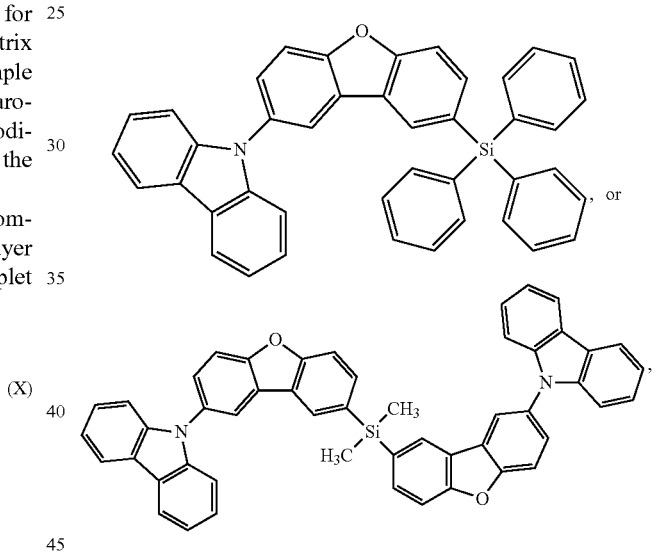

are described in WO2010079051 (PCT/EP2009/067120; in particular pages on 19 to 26 and in tables on pages 27 to 34, pages 35 to 37 and pages 42 to 43).

Additional matrix materials on basis of dibenzofurane are, for example, described in US2009066226, EP1885818B1, EP1970976, EP1998388 and EP2034538. Examples of particularly preferred matrix materials are shown below:

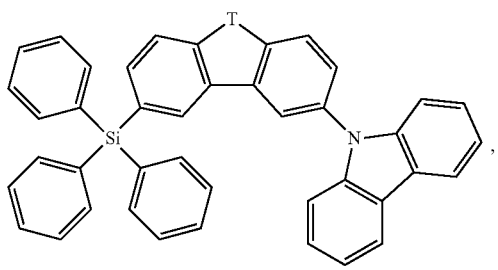

-continued
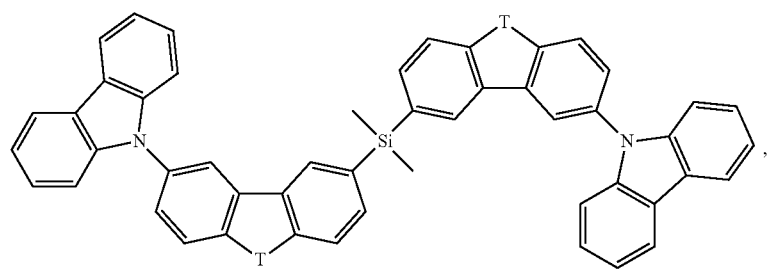
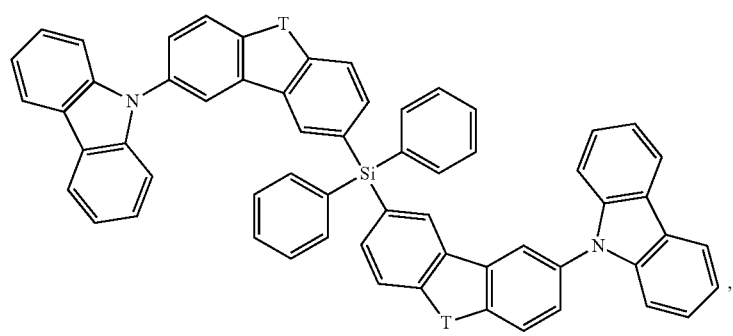
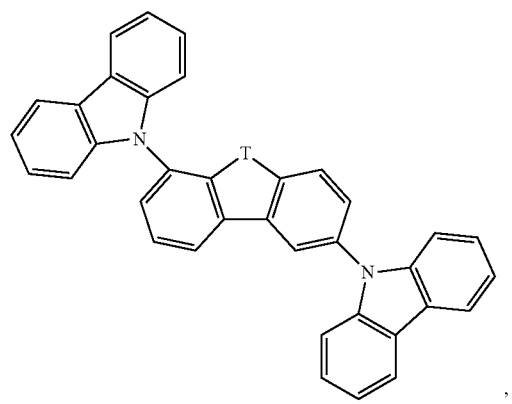
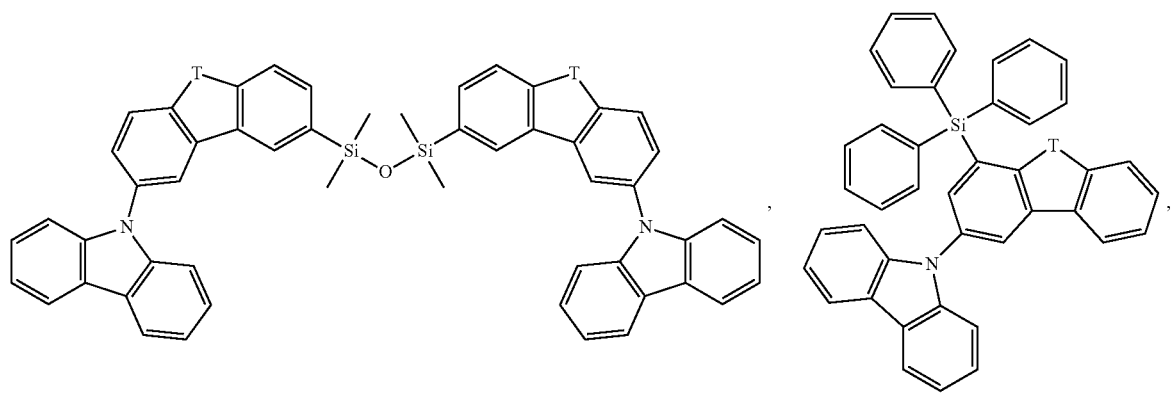

-continued
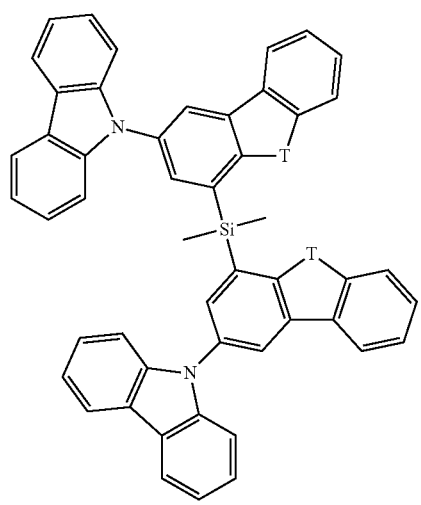
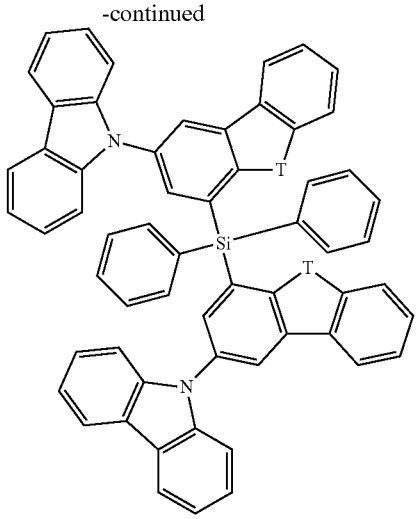
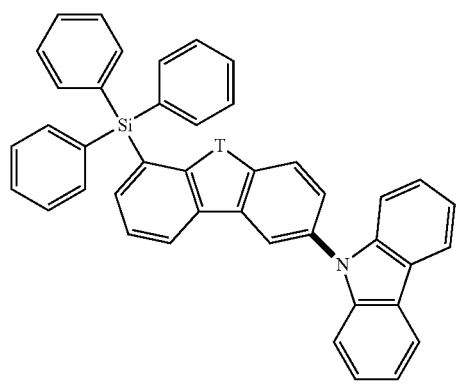
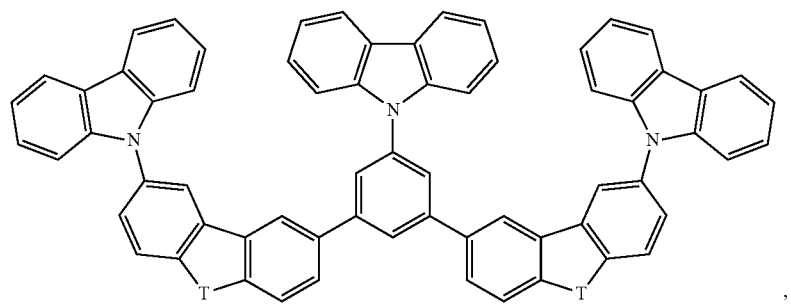
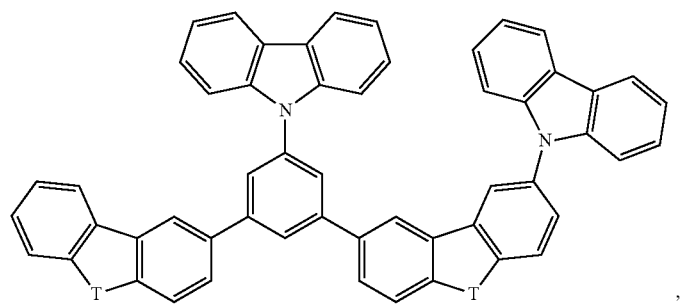

-continued
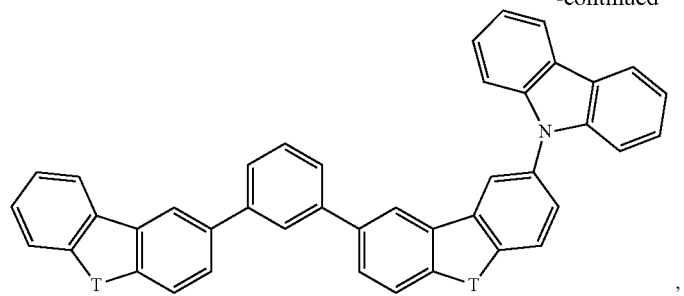
,
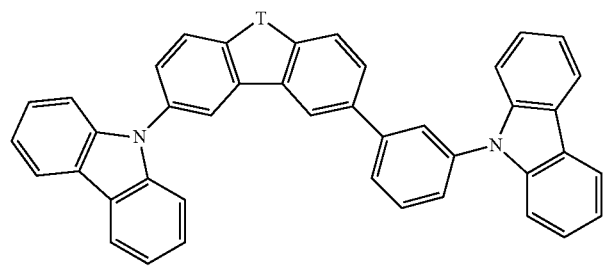
,
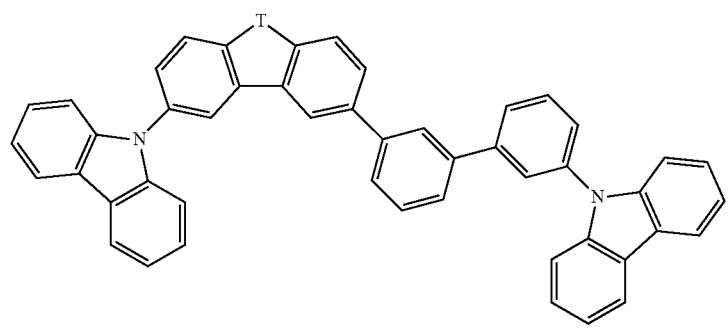
,
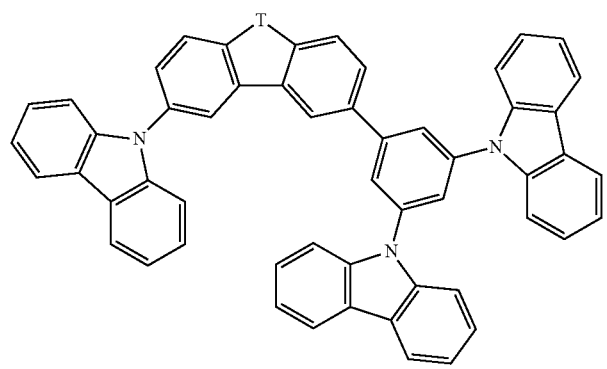
,
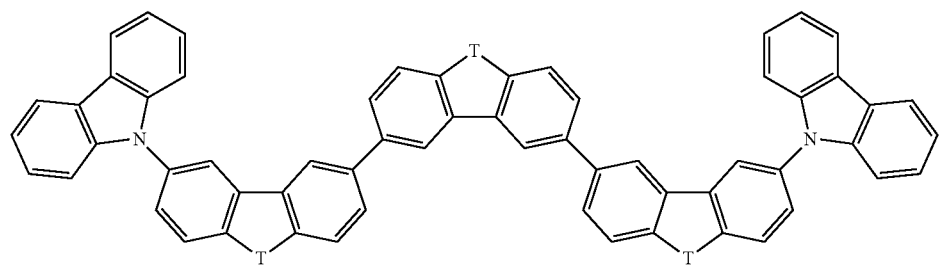
, -continued
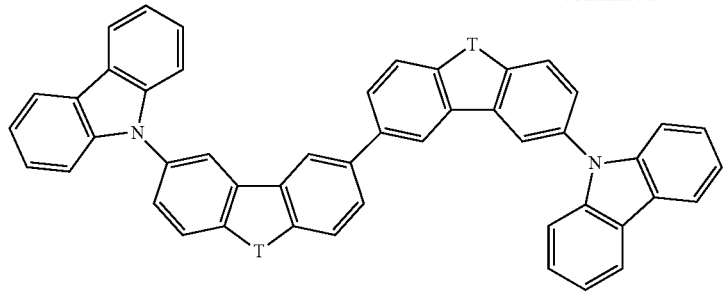
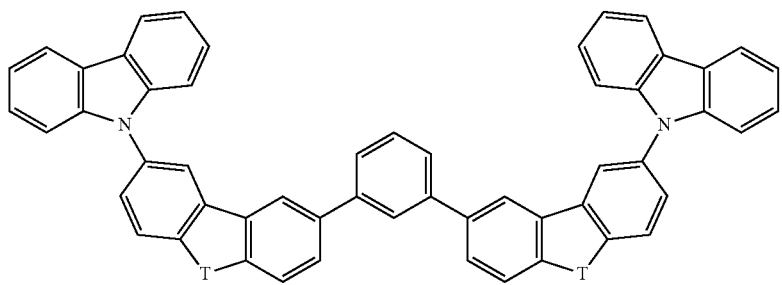
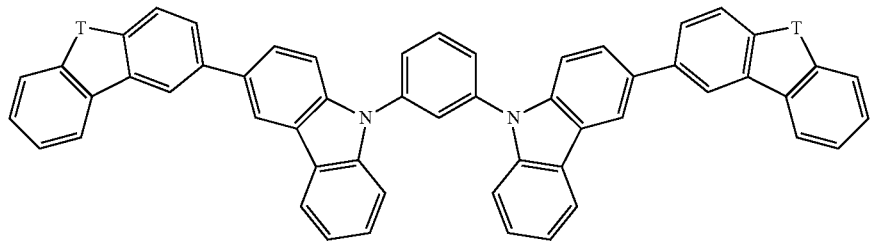
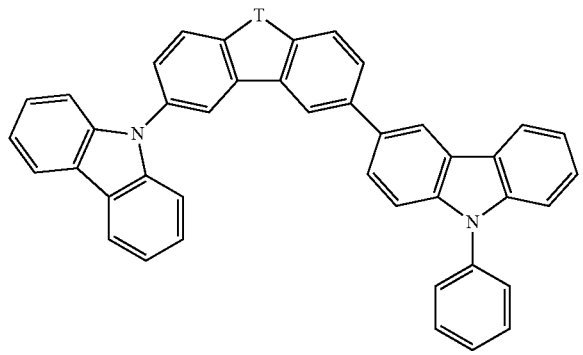
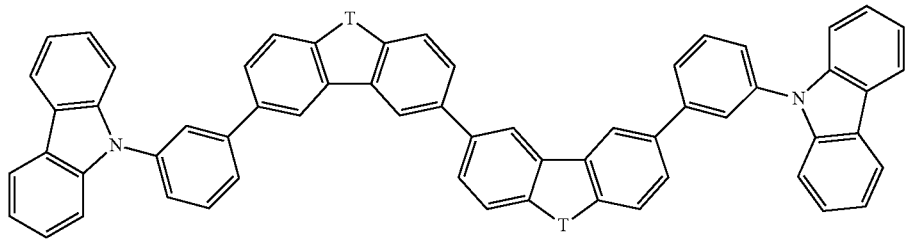

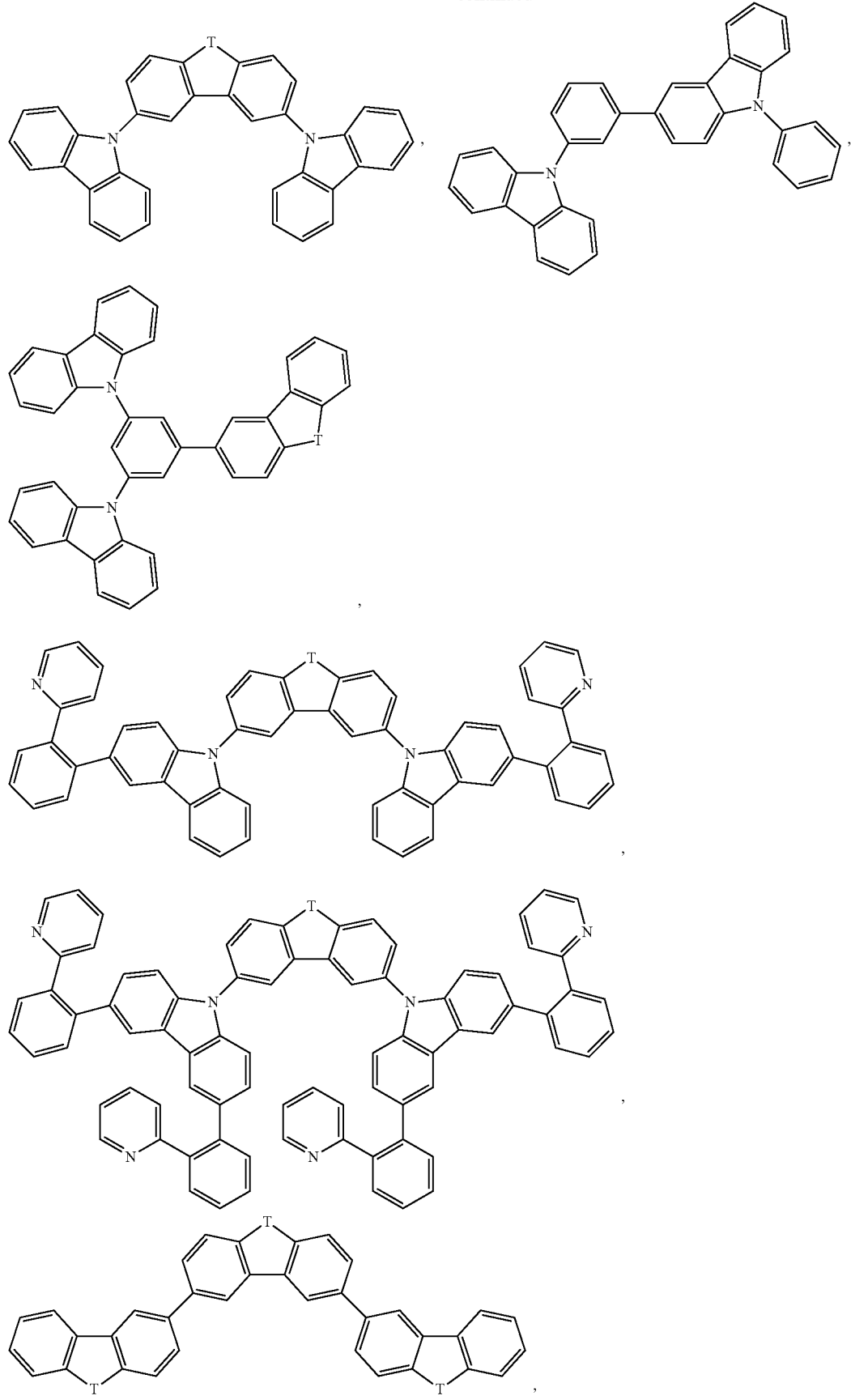

-continued
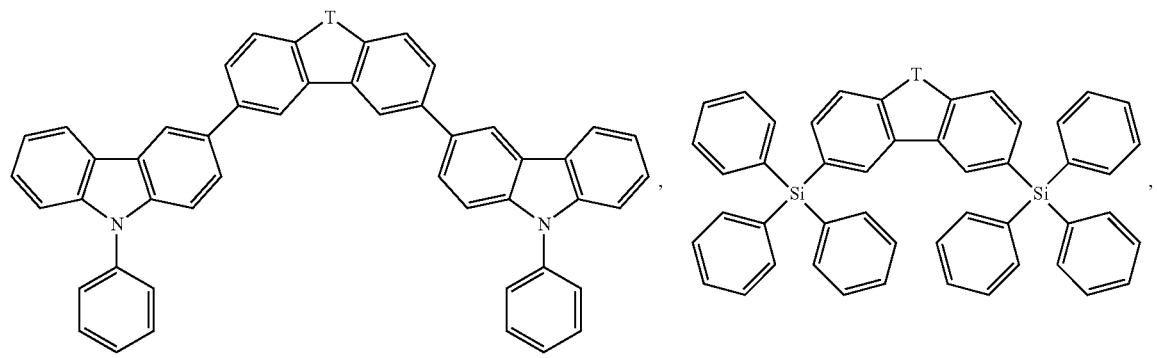
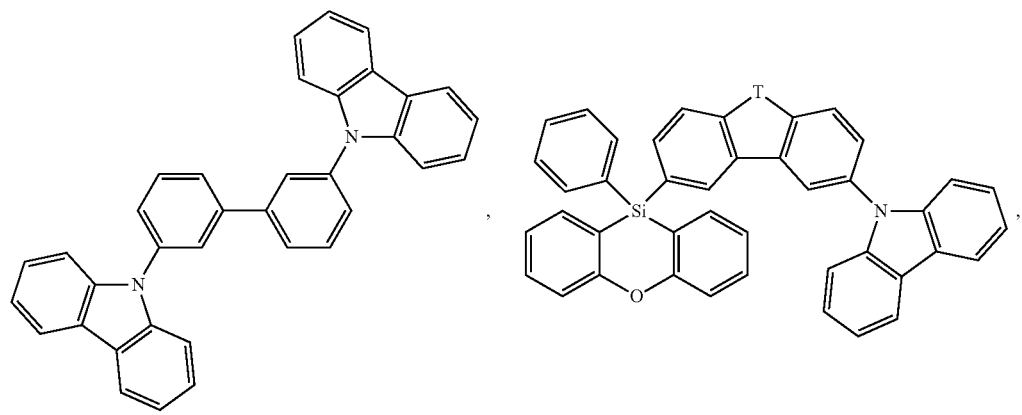
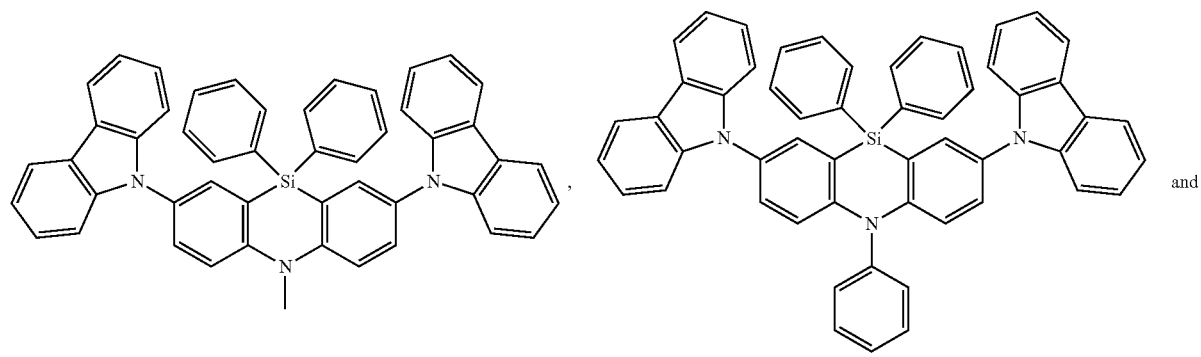
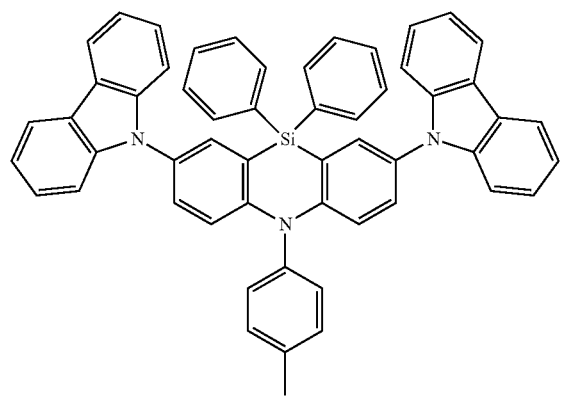

In the above-mentioned compounds T is O, or S, preferably O. If T occurs more than one time in a molecule, all groups T have the same meaning. Additional matrix materials, such as, for example,

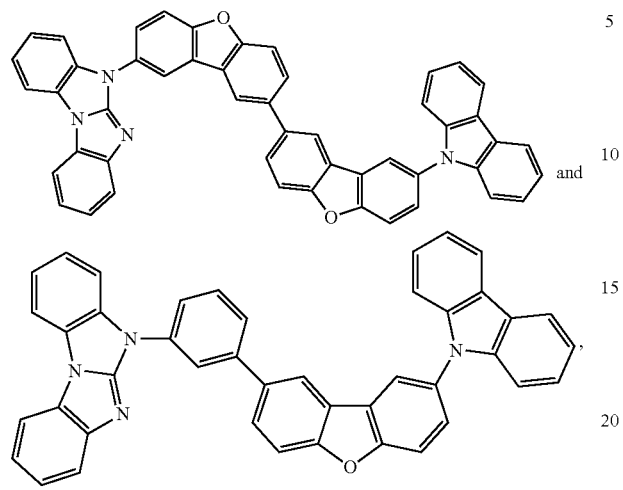

are described in WO2012/130709.

In a preferred embodiment, the light-emitting layer is formed from 2 to 40% by weight, preferably 5 to 35% by weight, of at least one of the aforementioned emitter materials and 60 to 98% by weight, preferably 75 to 95% by weight, of at least one of the aforementioned matrix materials—in one embodiment at least one compound of the formula I—where the sum total of the emitter material and of the matrix material adds up to 100% by weight.

In particularly preferred embodiment, the light-emitting layer comprises a compound of formula

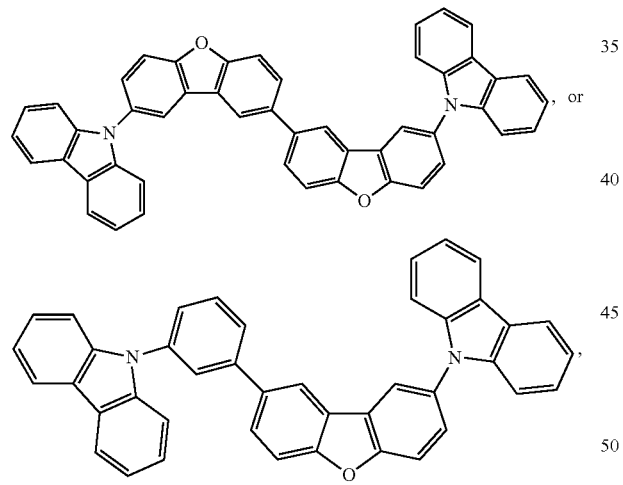

and two carbene complexes, preferably of formula

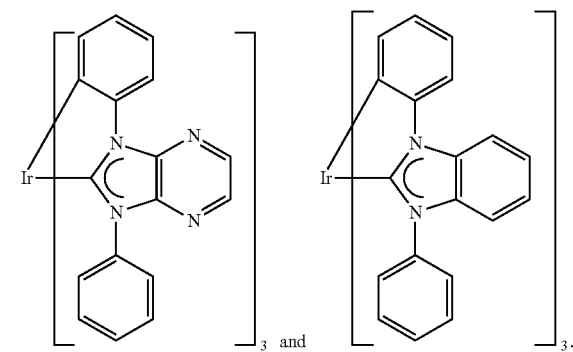

In said embodiment, the light-emitting layer is formed from 2 to 40% by weight, preferably 5 to 35% by weight, of

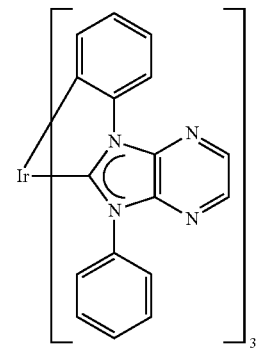

and 60 to 98% by weight, preferably 65 to 95% by weight, of a compound of the formula I and

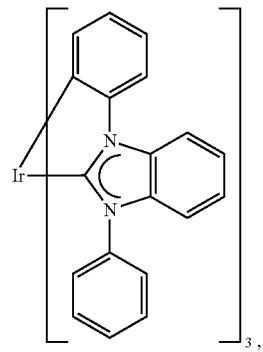

where the sum total of the carben complexes and of the compound of formula I adds up to 100% by weight.

Suitable metal complexes for use together with the compounds of the formula I as matrix material and/or hole/exciton blocker material and/or electron/exciton blocker material and/or hole injection material and/or electron injection material and/or hole transport material and/or electron transport material, preferably as matrix material and/or hole/exciton blocker material, in OLEDs are thus, for example, also carbene complexes as described in WO 2005/019373 A2, WO 2006/056418 A2, WO 2005/113704, WO 2007/115970, WO 2007/115981 and WO 2008/000727. Explicit reference is made here to the disclosure of the WO applications cited, and these disclosures shall be considered to be incorporated into the content of the present application.

The blocking layer for holes/excitons (4) may comprise a compound of the formula I, such as, for example, a compound (A-9). If the blocking layer for holes/excitons (4) does not comprise any compounds of the formula I, the OLED has—if a blocking layer for holes is present—hole blocker materials typically used in OLEDs, such as 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato)aluminum(III) (BAlq), phenothiazine S,S-dioxide derivates and 1,3,5-tris(N-phenyl-2-benzylimidazolyl)benzene) (TPBI), TPBI also being suitable as electron-conducting material. Further suitable hole blockers and/or electron transport materials are 2,2',2"-(1,3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2'-bipyridyl, 2-phenyl-9,10-di(naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris(2,4,6-trimethyl-3-(pyridin-3-yl)phenyl)borane, 2,9-bis(naphthalene-2-yl)-4,7-diphenyl-1,10-phenanthroline, 1-methyl-2-(4-(naphthalene-2-yl)phenyl)-1H-imidazo[4,5-f][1,10]phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene S-oxides and disilylbenzothiophene S,S-dioxides, as specified, for example, in PCT applications PCT/EP2008/058207 and PCT/EP2008/058106, which were yet to be published at the priority date of the present application, and disilyl compounds as disclosed in WO2008/034758, as a blocking layer for holes/excitons (4) or as matrix materials in the light-emitting layer (3).

In addition—in one embodiment—it is possible to use carbene complexes as hole transport materials, the band gap of the at least one hole transport material generally being greater than the band gap of the emitter material used. In the context of the present application, "band gap" is understood to mean the triplet energy. Suitable carbene complexes are, for example, carbene complexes as described in WO 2005/019373 A2, WO 2006/056418 A2, WO 2005/113704, WO 2007/115970, WO 2007/115981 and WO 2008/000727. One example of a suitable carbene complex is fac-Iridium-tris(1,3-diphenylbenzimidazolin-2-yliden-C,$C^{2'}$) (Ir(dpbic)$_3$) with the formula:

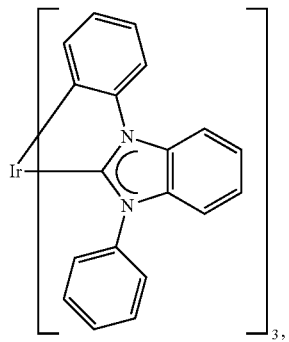

which is disclosed, for example, in WO2005/019373. Preferably, the hole transport layer comprises Ir(dpbic)$_3$ doped with molybdenum oxide (MoO$_x$), especially MoO$_3$, or rhenium oxide (ReO$_x$), especially ReO$_3$. The dopant is contained in an amount of from 0.1% by weight, preferably 1 to 8% by weight, more preferably 3 to 5% by weight, based on the amount of dopant and carbene complex.

Suitable electron transport materials for the layer (5) of the inventive OLEDs comprise compounds of the formula I, such as, for example, a compound (A-9); metals chelated to oxinoid compounds, such as 2,2',2''-(1,3,5-phenylene)tris[1-phenyl-1H-benzimidazole] (TPBI), tris(8-quinolinolato)aluminum (Alq$_3$), compounds based on phenanthroline, such as 2,9-dimethyl-4,7-diphenyl-1,10-phenanthroline (DDPA=BCP) or 4,7-diphenyl-1,10-phenanthroline (DPA), and azole compounds such as 2-(4-biphenylyl)-5-(4-t-butyl-phenyl)-1,3,4-oxadiazole (PBD) and 3-(4-biphenylyl)-4-phenyl-5-(4-t-butylphenyl)-1,2,4-triazole (TAZ), 8-hydroxyquinolinolatolithium (Liq), 4,7-diphenyl-1,10-phenanthroline (BPhen), bis(2-methyl-8-quinolinolato)-4-(phenyl-phenolato)aluminum (BAlq), 1,3-bis[2-(2,2'-bipyridin-6-yl)-1,3,4-oxadiazo-5-yl]benzene (Bpy-OXD), 6,6'-bis[5-(biphenyl-4-yl)-1,3,4-oxadiazo-2-yl]-2,2'-bipyridyl (BP-OXD-Bpy), 4-(naphthalen-1-yl)-3,5-diphenyl-4H-1,2,4-triazole (NTAZ), 2,9-bis(naphthalen-2-yl)-4,7-diphenyl-1,10-phenanthroline (NBphen), 2,7-bis[2-(2,2'-bipyridin-6-yl)-1,3,4-oxadiazo-5-yl]-9,9-dimethylfluorene (Bby-FOXD), 1,3-bis[2-(4-tert-butylphenyl)-1,3,4-oxadiazo-5-yl]benzene (OXD-7), tris(2,4,6-trimethyl-3-(pyridin-3-yl)-phenyl)borane (3TPYMB), 1-methyl-2-(4-(naphthalen-2-yl)phenyl)-1H-imidazo-[4,54][1,10]phenanthroline (2-NPIP), 2-phenyl-9,10-di(naphthalen-2-yl)anthracene (PADN), 2-(naphthalen-2-yl)-4,7-diphenyl-1,10-phenanthroline (HNBphen). The layer (5) may serve both to facilitate electron transport and as a buffer layer or barrier layer in order to prevent quenching of the exciton at the interfaces of the layers of the OLED. The layer (5) preferably improves the mobility of the electrons and reduces quenching of the exciton. In a preferred embodiment, BCP is used as the electron transport material. In another preferred embodiment, the electron transport layer comprises at least one compound of the formula I as electron transport material.

Among the materials mentioned above as hole transport materials and electron transport materials, some may fulfill several functions. For example, some of the electron-conducting materials are simultaneously hole-blocking materials when they have a low-lying HOMO.

These can be used, for example, in the blocking layer for holes/excitons (4). However, it is likewise possible that the function as a hole/exciton blocker is also adopted by the layer (5), such that the layer (4) can be dispensed with.

The charge transport layers can also be electronically doped in order to improve the transport properties of the materials used, in order firstly to make the layer thicknesses more generous (avoidance of pinholes/short circuits) and in order secondly to minimize the operating voltage of the device. For example, the hole transport materials can be doped with electron acceptors; for example, phthalocyanines or arylamines such as TPD or TDTA can be doped with tetrafluorotetracyanquinodimethane (F4-TCNQ) or with MoO$_3$ or WO$_3$. The electron transport materials can be doped, for example, with alkali metals, for example Alq$_3$ with lithium. In addition, electron transports can be doped with salts such as Cs$_2$CO$_3$, or 8-hydroxyquinolato-lithium (Liq). Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo. Appl. Phys. Lett., Vol. 82, No. 25, 23 Jun. 2003 and Pfeiffer et al., Organic Electronics 2003, 4, 89-103. For example, the hole transport layer may, in addition to a carbene complex, e.g. Ir(dpbic)$_3$, be doped with MoO$_3$ or WO$_3$. For example, the electron transport layer may comprise BCP doped with Cs$_2$CO$_3$.

The cathode (6) is an electrode which serves to introduce electrons or negative charge carriers. Suitable materials for the cathode are selected from the group consisting of alkali metals of group Ia, for example Li, Cs, alkaline earth metals of group IIa, for example calcium, barium or magnesium, metals of group IIb of the periodic table of the elements (old IUPAC version), comprising the lanthanides and actinides, for example samarium. In addition, it is also possible to use metals such as aluminum or indium, and combinations of all metals mentioned. In addition, alkali metal-comprising organometallic compounds, or alkali metal fluorides, such as, for example, LiF, CsF, or KF, can be applied between the organic layer and the cathode in order to reduce the operating voltage.

The OLED according to the present invention may additionally comprise further layers which are known to those skilled in the art. For example, a layer which facilitates the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to facilitate the transport of negative charge and/or to match the band gaps between the layers to one another. Alternatively, this layer may serve as a protective layer.

In a preferred embodiment, the inventive OLED, in addition to layers (1) to (6), comprises at least one of the following layers mentioned below:

a hole injection layer between the anode (1) and the hole-transporting layer (2) having a thickness of 2 to 100 nm, preferably 5 to 50 nm;

a blocking layer for electrons between the hole-transporting layer (2) and the light-emitting layer (3);

an electron injection layer between the electron-transporting layer (5) and the cathode (6).

Materials for a hole injection layer may be selected from copper phthalocyanine, 4,4',4"-tris(N-3-methylphenyl-N-phenylamino)triphenylamine (m-MTDATA), 4,4',4"-tris-(N-(2-naphthyl)-N-phenylamino)triphenylamine (2T-NATA), 4,4',4"-tris(N-(1-naphthyl)-N-phenylamino) triphenylamine (1T-NATA), 4,4',4"-tris(N,N-diphenylamino)triphenylamine (NATA), titanium oxide phthalocyanine, 2,3,5,6-tetrafluoro-7,7,8,8-tetracyanoquinodimethane (F4-TCNQ), pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spirobifluorene (MeO-Spiro-TPD), 2,2'-bis[N,N-bis(4-methoxyphenyl)amino]-9,9-spirobifluorene (2,2'-MeO-Spiro-TPD), N,N'-diphenyl-N,N'-di-[4-(N,N-ditolylamino)phenyl]benzidine (NTNPB), N,N'-diphenyl-N,N'-di-[4-(N,N-diphenylamino)phenyl] benzidine (NPNPB), N,N'-di(naphthalen-2-yl)-N,N'-diphenylbenzene-1,4-diamine (α-NPP). In principle, it is possible that the hole injection layer comprises at least one compound of the formula I as hole injection material. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

As a material for the electron injection layer, LiF, for example, can be selected. In principle, it is possible that the electron injection layer comprises at least one compound of the formula I as electron injection material.

In addition, it is possible that some of the layers used in the inventive OLED have been surface-treated in order to increase the efficiency of charge carrier transport.

The inventive OLED can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

In general, the different layers have the following thicknesses: anode (1) 50 to 500 nm, preferably 100 to 200 nm; hole-conducting layer (2) 5 to 100 nm, preferably 20 to 80 nm, light-emitting layer (3) 1 to 100 nm, preferably 10 to 80 nm, blocking layer for holes/excitons (4) 2 to 100 nm, preferably 5 to 50 nm, electron-conducting layer (5) 5 to 100 nm, preferably 20 to 80 nm, cathode (6) 20 to 1000 nm, preferably 30 to 500 nm. The relative position of the recombination zone of holes and electrons in the inventive OLED in relation to the cathode and hence the emission spectrum of the OLED can be influenced, among other factors, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. It is possible that the electron-conducting layer and/or the hole-conducting layer have greater thicknesses than the layer thicknesses specified when they are electrically doped.

Use of the compounds of the formula I in at least one layer of the OLED, preferably in the light-emitting layer (preferably as a matrix material) and/or in the transport layer for electrons and/or in the blocking layer for holes/excitons makes it possible to obtain OLEDs with high efficiency and with low use and operating voltage. Frequently, the OLEDs obtained by the use of the compounds of the formula I additionally have high lifetimes. The efficiency of the OLEDs can additionally be improved by optimizing the other layers of the OLEDs. For example, high-efficiency cathodes such as Ca or Ba, if appropriate in combination with an intermediate layer of LiF, can be used. Shaped substrates and novel hole-transporting materials which bring about a reduction in the operating voltage or an increase in the quantum efficiency are likewise usable in the inventive OLEDs. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, laptops, digital cameras, MP3 players, vehicles and destination displays on buses and trains. Further devices in which the inventive OLEDs can be used are, for example, keyboards; items of clothing; furniture; wallpaper.

In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight.

EXAMPLES

Example 1

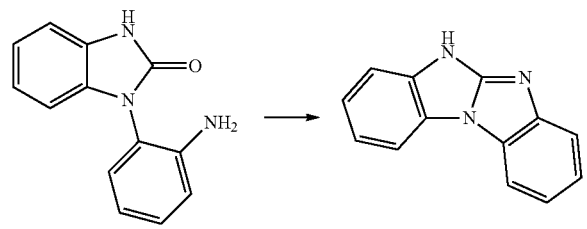 [SMILES: Nc1ccccc1-n1c(=O)[nH]c2ccccc21 ; c1ccc2c(c1)nc1[nH]c3ccccc3n12]

a) 11.3 g (50.0 mmol) 3-(2-aminophenyl)-1H-benzimidazol-2-one are added to 50 g polyphosphoric acid at 180° C. The reaction mixture is stirred at 220° C. for 3 h under nitrogen and poured into water. The product is filtered off and washed with water and methanol. 50 ml 30% sodium hydroxide solution are added to a suspension of the product in 200 ml THF. The mixture is stirred for 30 minutes and the organic phase is separated, dried with magnesium sulfate and the solvent is distilled off. 9.26 g of 6H-benzimidazolo[1,2-a]benzimidazole are obtained (yield: 89%).

$^1$H NMR (400 MHz, DMSO-d6): δ 7.88 (d, J=7.7 Hz, 2H), 7.39 (d, J=8.0 Hz, 2H), 7.12-7.16 (m, 2H), 6.97-7.01 (m, 2H).

The synthesis of 5H-benzimidazo[1,2-a]benzimidazole and 3-(2-aminophenyl)-1H-benzimidazol-2-one is described in Bull. Soc. Chem. Belg. 96 (1987) 787.

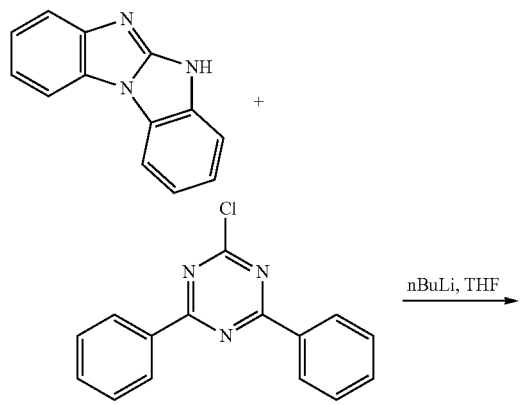

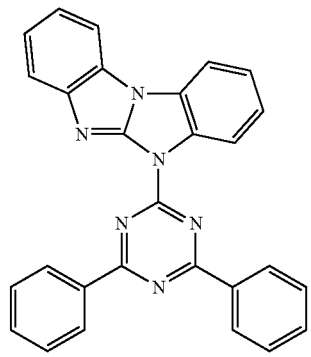

A-9 b) 9.7 ml (24.1 mmol) n-butyl-lithium 2.5 M in hexane are added to 5 g (24.21 mmol) 6H-benzimidazolo[1,2-a]benzimidazole in 100 ml water free THF at −78° C. under argon. The reaction mixture is stirred for 15 minutes at −78° C. and is then warmed to −25° C. Then the reaction mixture is cooled to 0° C., a solution of 2-chloro-4,6-diphenyl-1,3,5-triazine, the synthesis of which is described in WO2010/067894, in 50 ml THF is added, the reaction mixture is stirred for 15 minutes at 0° C. and is then heated under argon at 60° C. for 24 h. The product is filtered off, washed with THF, dissolved in DMSO and poured into water. After filtration 7.89 g of the compound A-9 are obtained (yield: 79%).

$^1$H NMR (400 MHz, CDCl$_3$): 9.02-9.04 (m, 1H), 8.84 (d, J=6.6 Hz, 4H), 8.00 (d, J=7.9 Hz, 1H), 7.80-7.86 (m, 2H), 7.61-7.68 (m, 6H), 7.40-7.52 (m, 2H), 7.36-7.45 (m, 2H).

MS (APCI (pos)): m/z (%): 439 (M$^{+1}$, 100%).

Example 2

The synthesis of compound A-10 is carried out in analogy to the synthesis of compound A-9.

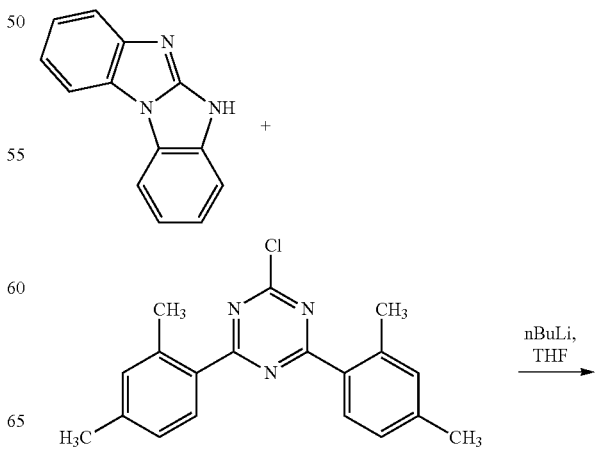

-continued

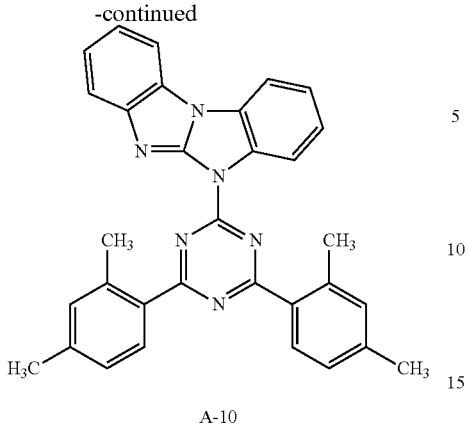

A-10

$^1$H NMR (400 MHz, CDCl$_3$): 8.93 (d, J=8.0 Hz, 1H), 8.28 (d, J=7.9 Hz, 2H), 7.92 (d, J=7.2 Hz, 1H), 7.85 (d, J=7.2 Hz, 1H), 7.78-7.80 (m, 1H), 7.35-7.46 (m, 4H), 7.20-7.24 (m, 4H), 2.89 (s, 6H), 2.44 (s, 6H). MS (APCI (pos): m/z (%): 495 (M$^{+1}$, 100%).

Example 3

The synthesis of compound A-11 is carried out in analogy to the synthesis of compound A-9.

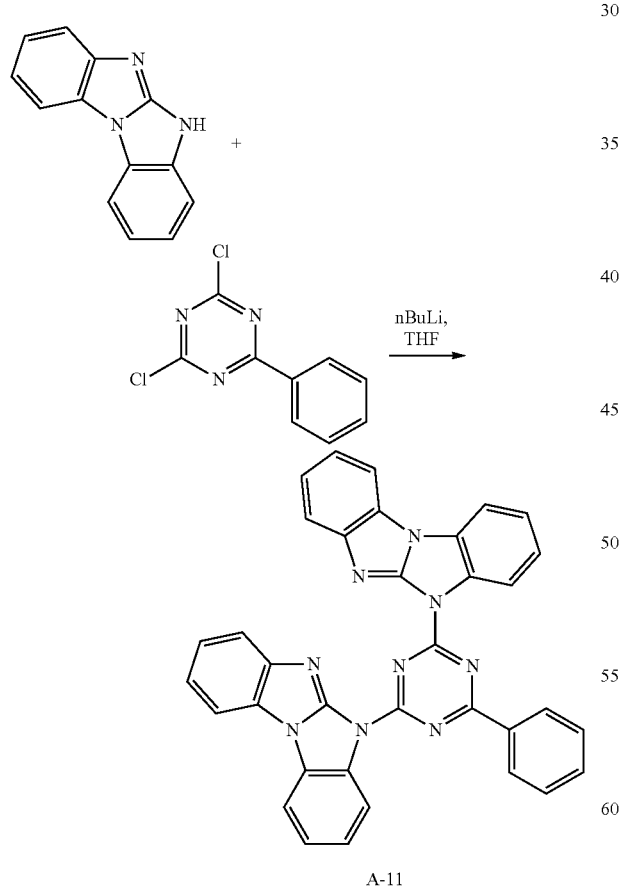

A-11

$^1$H NMR (400 MHz, TFA-d1): 8.94-8.97 (m, 2H), 8.69 (d, J=7.4, 2H), 8.21-8.27 (m, 4H), 7.69-7.95 (m, 13H).
MS (APCI (pos)): m/z: 568 (M$^{+1}$).

Example 4

The synthesis of compound A-12 is carried out in analogy to the synthesis of compound A-9.

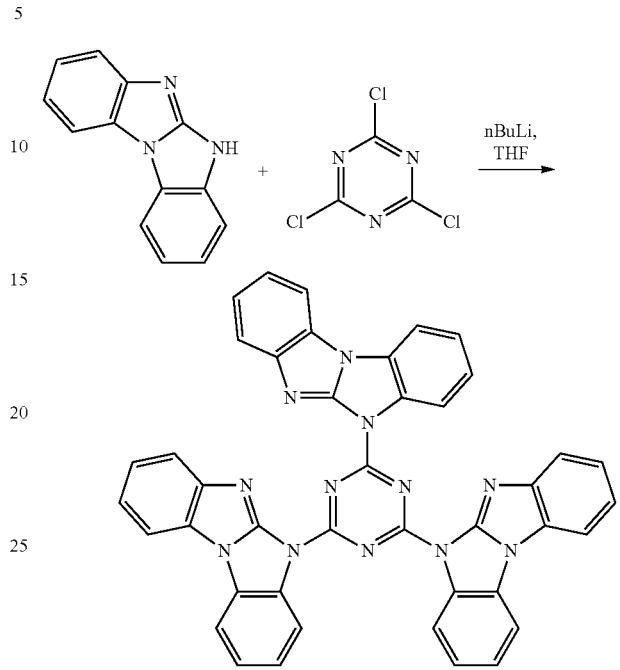

A-12

$^1$H NMR (400 MHz, TFA-d1): 8.77 (d, J=8.3 Hz, 3H), 8.28 (d, J=8.1 Hz, 3H), 8.25 (d, J=8.1 Hz, 3H), 7.71-7.91 (m, 15H).
MS (ESI): m/z: 697 (M$^{+1}$).

Example 5

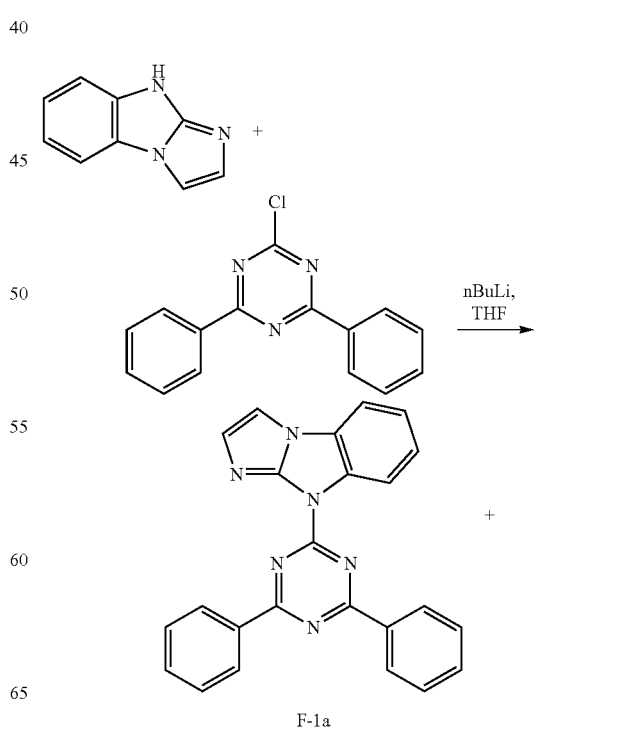

F-1a

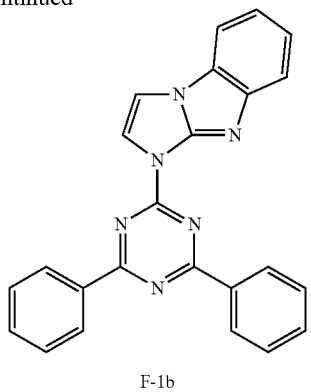

F-1b

The synthesis of 4H-imidazo[1,2-a]benzimidazole is described in ARKIVOC 2002 (v) 48-61. The synthesis of compound F-1a and F-1b is carried out in analogy to the synthesis of compound A-9. The main isomer F-1a precipitates from the reaction mixture and can be filtered off. The mother liquor contains the isomers F-1a and F-1b, which can be separated by HPLC.

Isomer F-1a:

$^1$H NMR (400 MHz, CDCl$_3$): 9.00 (d, J=8.2 Hz, 1H), 8.79-8.82 (m, 4H), 7.54-7.66 (m, 7H), 7.36-7.49 (m, 4H).

MS (APCI (pos): m/z (%): 389 (M$^{+1}$, 100%).

Isomer F-1b:

MS (APCI (pos): m/z (%): 389 (M$^{+1}$, 100%).

Example 6

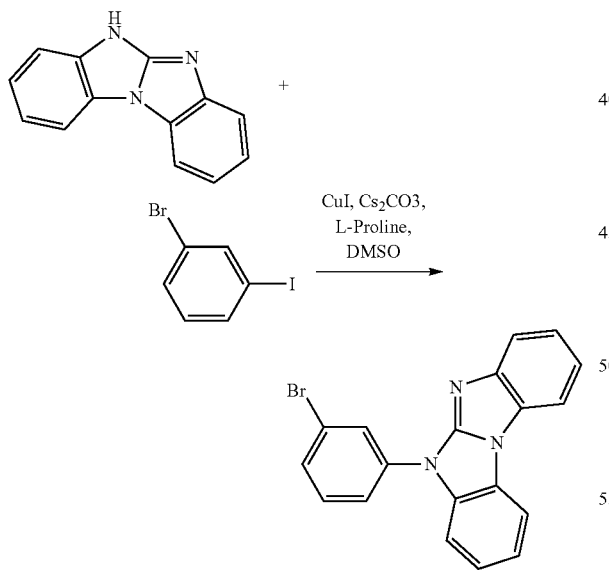

a) 7.78 g (25 mmol) 1-bromo-3-iodo-benzene, 16.3 g (50.0 mmol) caesium carbonate, 1.24 g (6.50 mmol) copper (I) iodide and 1.50 g (13.0 mmol) L-proline are added to 5.18 g (25.0 mmol) 5H-benzimidazo[1,2-a]benzimidazole in 100 ml dimethylsulfoxide (DMSO) under nitrogen. The reaction mixture is stirred for 18 h at 100° C. under nitrogen and is poured into water. The organic phase is extracted with dichloromethane. The organic phase is dried with magnesium sulfate. The solvent is distilled off. Column chromatography on silica gel with toluene results in the product (yield 8.35 g (92%)).

$^1$H NMR (400 MHz, CDCl$_3$): δ 8.25 (s, 1H), 7.90-8.05 (m, 3H), 7.95-8.05 (m, 3H), 7.71 (d, J=7.9 Hz, 1H), 7.65 (d, J=7.9 Hz, 1H). 7.50-7.65 (m, 2H), 7.26-7.45 (m, 4H).

b)

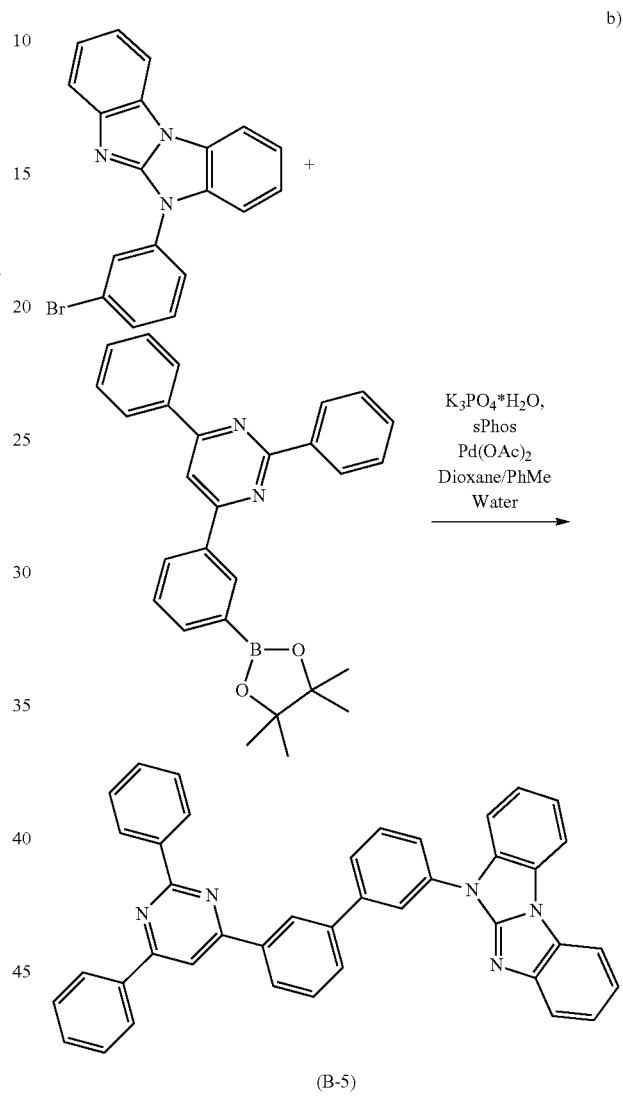

(B-5)

The synthesis of 2,4-diphenyl-6-[3-(4,4,5,5-tetramethyl-1,3,2-dioxaborolan-2-yl)phenyl]pyrimidine is described in Example 1 of WO2012/080052. 1.77 g (4.89 mmol) 5-(3-bromophenyl)benzimidazolo[1,2-a]benzimidazole and 5.63 g (24.4 mmol) potassium phosphate tribasic monohydrate, 25 ml dioxane, 50 ml toluene and 12 ml water are added to 2.55 g (5.86 mmol) of 2,4-diphenyl6-[3-(4,4,5,5-tetramethyl-1,3,2-dioxaborolan-2-yl)phenyl]pyrimidine. The mixture is degassed with argon. 120 mg (0.293 mmol) 2-dicyclohexylphosphino2',6'-dimethoxybiphenyl (SPhos) and 110 mg (0.049 mmol) palladium(II) acetate are added. The reaction mixture is degassed with argon and is stirred for 18 h at 100° C. under argon. 25 ml of a 1% sodium cyanide solution are added and the reaction mixture is refluxed for 1 h. Dichloromethane and water are added, and the organic phase is separated. The organic phase is washed with water and dried with magnesium sulfate. Column chromatography on silica gel with toluene/ethyl acetate (15/1 and then 10/1) results in the crude product, which is crystallized from toluene (yield: 1.08 g (38%)).

$^1$H NMR (400 MHz, DMSO-d6+TFA-d1): δ 8.85 (s, 1H), 8.66-8.69 (m, 2H), 8.65 (s, 1H), 8.49-8.59 (m, 5H), 8.37 (s, 1H), 8.19-8.22 (m, 1H), 8.03 (d, J=8.3 Hz, 1H), 7.93-7.95 (m, 2H), 7.75-7.81 (m, 3H), 7.54-7.71 (m, 10H). MS (APCI (pos), m/z): 590 (M$^{+1}$).

Example 7

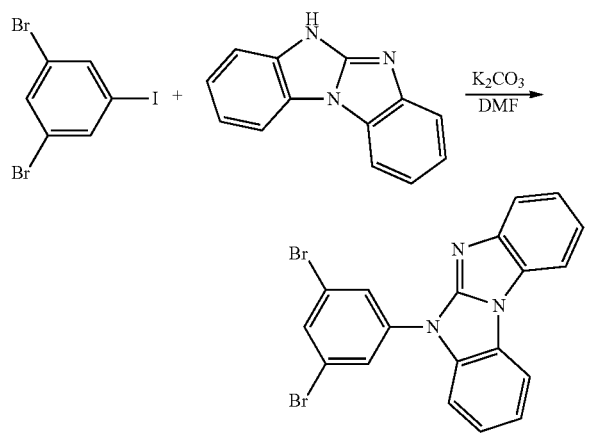

a) 20.0 g (78.8 mmol) 1,3-dibromo-5-fluoro-benzene, 16.3 g (78.8 mmol) 6H-benzimidazolo[1,2-a]benzimidazole and 43.5 g (0.315 mmol) potassium carbonate in 200 ml DMF are stirred for 17 h at 170° C. The reaction mixture is filtered hot and the precipitate from the mother liquor is filtered after cooling. The product is washed with water and ethanol and decocted with diethyl ether and ethanol (yield 21.2 g (61%)).

$^1$H NMR (400 MHz, THF-d8): δ 8.21-8.26 (m, 4H), 7.98-7.8.00 (m, 1H), 7.68-7.73 (m, 2H), 7.31-7.49 (m, 4H).

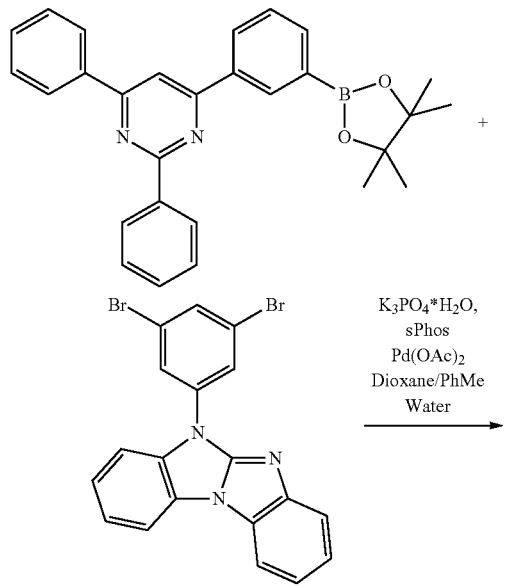

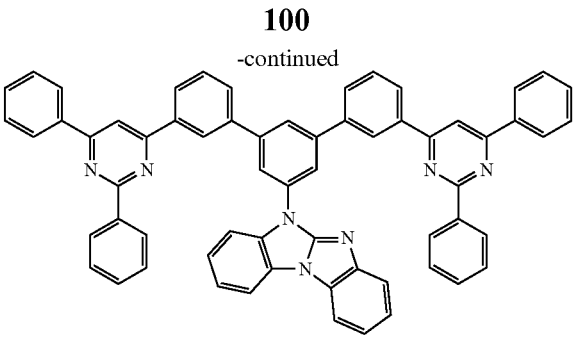

b) 1.50 g (3.40 mmol) 5-(3,5-dibromophenyl)benzimidazolo[1,2-a]benzimidazole and 4.12 g (17.0 mmol) potassium phosphate tribasic monohydrate, 15 ml dioxane, 60 ml toluene and 12 ml water are added to 3.54 g (8.16 mmol) of 2,4-diphenyl-6-[3-(4,4,5,5-tetramethyl-1,3,2-dioxaborolan-2-yl)phenyl]pyrimidine. The mixture is degassed with argon. 84 mg (0.20 mmol) 2-dicyclohexylphosphino-2',6'-dimethoxybiphenyl (SPhos) and 76 mg (0.034 mmol) palladium(II) acetate are added. The reaction mixture is degassed with argon and is stirred for 4 h at 100° C. under argon. 25 ml of a 1% sodium cyanide solution are added and the reaction mixture is refluxed for 1 h. Dichloromethane and water are added, and the organic phase is separated. The organic phase is washed with water and dried with magnesium sulfate. The product is decocted two times with acetic acid. The product (E-2) is washed with a saturated sodium hydrogen carbonate solution and dried (yield 69%).

MS (APCI(pos), m/z): 897 (M$^{+1}$). $^1$H NMR (400 MHz, TFA-dl): δ 8.74 (s, 2H), 8.63 (s, 2H), 8.44-8.49 (m, 7H), 8.22-8.36 (m, 10H), 7.99 (t, J=7.9 Hz, 2H), 7.85-7.93 (m, 6H), 7.73-7.83 (m, 12H).

Application Example 1

Hole Blocker and Electron Transport Material (ETM)

The ITO substrate used as the anode is first cleaned with an acetone/isopropanol mixture in an ultrasound bath. To eliminate any possible organic residues, the substrate is exposed to a continuous ozone flow in an ozone oven for further 25 minutes. This treatment also improves the hole injection properties of the ITO. Then Plexcore® OC AJ20-1000 (commercially available from Plextronics Inc.) is spin-coated and dried to form a hole injection layer (~40 nm).

Thereafter, the organic materials specified below are applied by vapor deposition to the clean substrate at a rate of approx. 0.5-5 nm/min at about $10^{-7}$-$10^{-9}$ mbar. As a hole transport and exciton blocker,

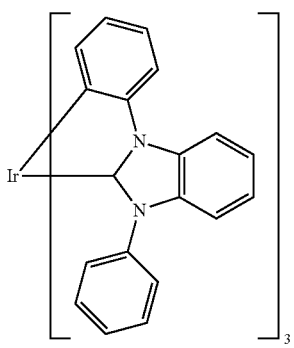

(Ir(dpbic)$_3$; for preparation, see Ir complex (7) in the application WO2005/019373), is applied to the substrate with a thickness of 20 nm, wherein the first 10 nm are doped with MoO$_x$ (~10%) to improve the conductivity.

Subsequently, a mixture of 30% by weight of emitter compound,

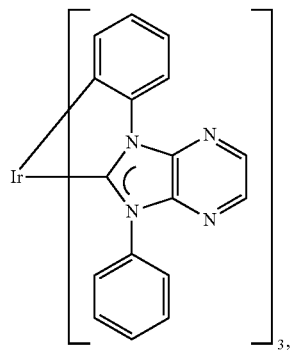

10% by weight of compound Ir(dpbic)$_3$ and 60% by weight of compound

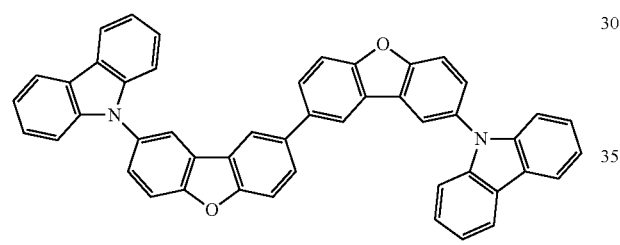

(H-1)

is applied by vapor deposition in a thickness of 30 nm.

Subsequently, the material

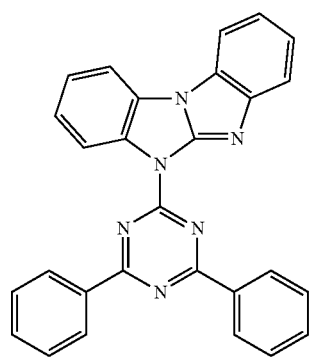

(A-9)

is applied by vapour deposition with a thickness of 5 nm as blocker. An additional layer of this material doped with Cs$_2$CO$_3$ is applied as electron transport layer by vapor deposition in a thickness of 20 nm and finally a 100 nm-thick Al electrode completes the device. All fabricated parts are sealed with a glass lid and a getter in an inert nitrogen atmosphere.

Application Example 2

Hole Blocker and Host

The sample preparation is done as in Application Example 1, but the setup is changed as follows:

As a hole transport and exciton blocker,

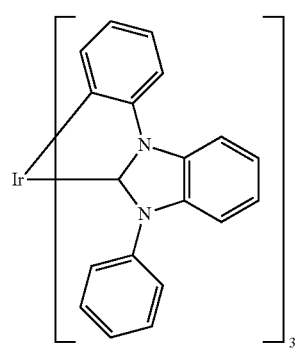

(Ir(dpbic)$_3$; for preparation, see Ir complex (7) in the application WO2005/019373), is applied to the substrate with a thickness of 20 nm, wherein the first 10 nm are doped with MoO$_x$ (~10%) to improve the conductivity.

Subsequently, a mixture of 30% by weight of emitter compound,

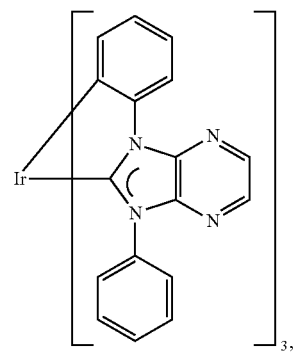

10% by weight of compound Ir(dpbic)$_3$ and 60% by weight of compound (A-10)

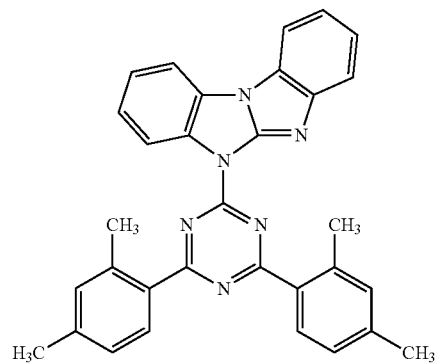

is applied by vapor deposition in a thickness of 40 nm. Subsequently, material (A-10) is applied by vapour deposition with a thickness of 5 nm as blocker. An additional layer of BCP

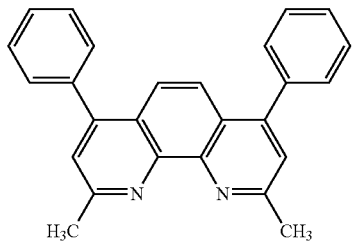 [SMILES: Cc1cc(-c2ccccc2)c2ccc3c(-c4ccccc4)cc(C)nc3c2n1]

doped with Cs₂CO₃ is applied as electron transport layer by vapor deposition in a thickness of 20 nm and finally a 100 nm-thick Al electrode completes the device.

Application Example 3

Hole Blocker and ETM

The sample preparation is done as in Application Example 1, but the setup is changed as follows: The emission layer is 40 nm instead of 30 nm thick. As hole blocking material compound (A-11)

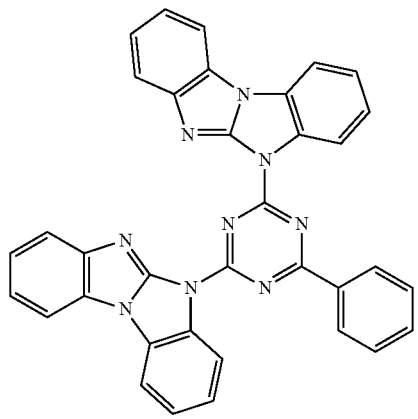

is deposited instead of compound (A-9) in 5 nm thickness. Furthermore, compound (A-11) doped with 5% Cs₂CO₃ is applied instead of compound (A-9) and Cs₂CO₃ as electron transport layer with a thickness of 20 nm.

Application Example 4

ETM

The sample preparation is done as in Application Example 1, but the setup is changed as follows: As a hole transport and exciton blocker,

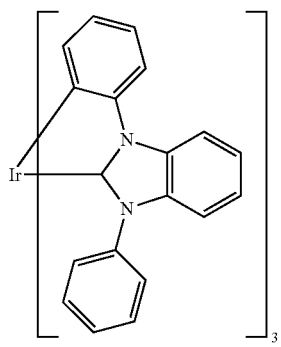

(Ir(dpbic)₃; for preparation, see Ir complex (7) in the application WO2005/019373), is applied to the substrate with a thickness of 20 nm, wherein the first 10 nm are doped with MoO$_x$ (~10%) to improve the conductivity.

Subsequently, a mixture of 10% by weight of emitter compound,

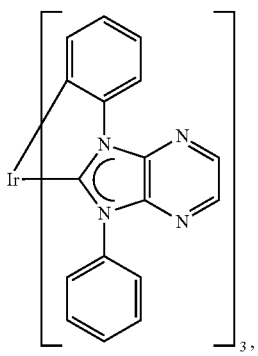

5% by weight of compound Ir(dpbic)₃ and 85% by weight of compound (H-2)

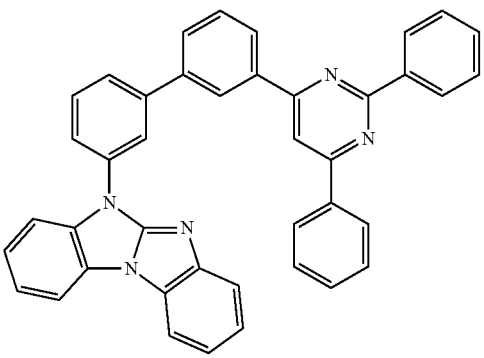

is applied by vapor deposition in a thickness of 40 nm. Subsequently, material (H-2) is applied by vapour deposition with a thickness of nm as blocker. Thereafter, a mixture of 50% by weight of material (B-5)

and of material

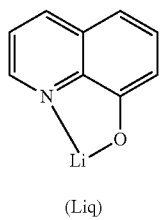

(Liq)

is applied as electron transport layer by vapor deposition with a thickness of 20 nm. A 100 nm-thick Al electrode completes the device.

Application Example 5

Hole Blocker and ETM

Production and construction of an OLED is as in Application Example 4, except that instead of the hole blocking material (H-2) the hole blocking material (B-5) is used.

To characterize the OLED, electroluminescence spectra are recorded at various currents and voltages. In addition, the current-voltage characteristic is measured in combination with the light output emitted. The light output can be converted to photometric parameters by calibration with a photometer. To determine the lifetime, the OLED is operated at a constant current density and the decrease in the light output is recorded. The lifetime is defined as that time which lapses until the luminance decreases to half of the initial luminance.

V at 300 cd/m², EQE (%) at 300 cd/m² and chromaticity coordinates according to CIE measured for the devices of Application Examples 1 to 5 are shown in the Tables below:

| | Hole blocker | ETM | Voltage @ 300 nits [V] | EQE[1] @ 300 nits [%] | CIE [x/y-value] |
|---|---|---|---|---|---|
| Appl. Ex. 1 | Cpd. A-9 | Cpd. A-9 | 4.06 | 14.9 | 0.17/0.35 |
| Appl. Ex. 3 | Cpd. A-11 | Cpd. A-11 | 4.32 | 13.8 | 0.19/0.39 |
| Appl. Ex. 4 | Cpd. H-2 | Cpd. B-5 | 6.82 | 16.3 | 0.16/0.30 |
| Appl. Ex. 5 | Cpd. B-5 | Cpd. B-5 | 5.97 | 16.2 | 0.17/0.30 |

| | Hole blocker | Host | Voltage @ 300 nits [V] | EQE[1] @ 300 nits [%] | CIE [x/y-value] |
|---|---|---|---|---|---|
| Appl. Ex. 2 | Cpd. A-10 | Cpd. A-10 | 3.05 | 11.4 | 0.18/0.37 |

[1]External quantum efficiency (EQE) is # of generated photons escaped from a substance or a device/# of electrons flowing through it.

The invention claimed is:
1. A compound of the formula

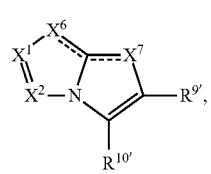

(I)

wherein:
$X^6$ is $-N=$ and $X^7$ is $-NR^6-$; or
$X^7$ is $=N-$ and $X^6$ is $-NR^6-$;
$R^6$ is a group of formula

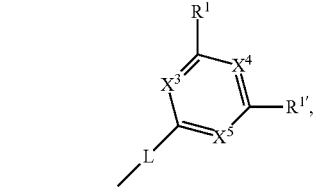

or

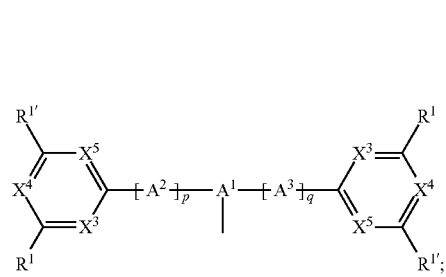

$A^1$ is a branching unit having three linkage sites;
$A^2$ and $A^3$ are each independently a $C_6$-$C_{24}$arylen group, optionally substituted by G, or a $C_2$-$C_{30}$heteroarylen group, optionally substituted by G; wherein the groups $A^1$, $A^2$ and $A^3$ may be interrupted by one or more groups $-(SiR^7R^8)-$;
$R^1$ and $R^{1'}$ are each independently H, a $C_1$-$C_{25}$alkyl group, optionally substituted by E and/or interrupted by D; a $C_6$-$C_{24}$aryl group, optionally substituted by G, or a $C_2$-$C_{30}$heteroaryl group, optionally substituted by G;
$R^7$ and $R^8$ are each independently a $C_1$-$C_{25}$alkyl group, or a $C_6$-$C_{24}$aryl group, optionally substituted by G;
L is a single bond or a linking group;
$X^1$ is N or $CR^9$;
$X^2$ is N or $CR^{10}$;
$X^3$ is N or $CR^{48}$;
$X^4$ is N or $CR^{49}$;
$X^5$ is N or $CR^{50}$, with the proviso that at least one of $X^3$, $X^4$ and $X^5$ is N;
$R^{48}$, $R^{49}$, $R^{50}$, $R^9$, $R^{10}$, $R^{9'}$ and $R^{10'}$ are each independently H, a $C_1$-$C_{25}$alkyl group, optionally substituted by E and/or interrupted by D; a $C_6$-$C_{24}$aryl group, optionally substituted by G, or a $C_2$-$C_{30}$heteroaryl group, optionally substituted by G; or
$R^9$ and $R^{10}$ and/or $R^{9'}$ and $R^{10'}$ together form an optionally substituted ring;
p is 0, 1, or 2; q is 0, 1, or 2;
D is $-CO-$, $-COO-$, $-S-$, $-SO-$, $-SO_2-$, $-O-$, $-NR^{65}-$, $-SiR^{70}R^{71}-$, $-POR^{72}-$, $CR^{63}=CR^{64}-$, or $-C\equiv C-$;
E is $-OR^{69}$, $-SR^{69}$, $-NR^{65}R^{66}$, $-COR^{68}$, $-COOR^{67}$, $-CONR^{65}R^{66}$, $-CN$, or a halogen;
G is E or a $C_1$-$C_{18}$alkyl group, a $C_6$-$C_{24}$aryl group, a $C_6$-$C_{24}$aryl group substituted by a $C_1$-$C_{18}$alkyl; a $C_2$-$C_{30}$heteroaryl group, or a $C_2$-$C_{30}$heteroaryl group substituted by a $C_1$-$C_{18}$alkyl;
$R^{63}$ and $R^{64}$ are each independently H, a $C_6$-$C_{18}$aryl; a $C_6$-$C_{18}$aryl substituted by a $C_1$-$C_{18}$alkyl, a $C_1$-$C_{18}$alkoxy; $C_1$-$C_{18}$alkyl; or a $C_1$-$C_{18}$alkyl which is interrupted by $-O-$;

$R^{65}$ and $R^{66}$ are each independently a $C_6$-$C_{18}$aryl group; a $C_6$-$C_{18}$aryl substituted by a $C_1$-$C_{18}$alkyl, or a $C_1$-$C_{18}$alkoxy; a $C_1$-$C_{18}$alkyl group; or a $C_1$-$C_{18}$alkyl group, which is interrupted by —O—; or $R^{65}$ and $R^{66}$ together form a five or six membered ring;

$R^{67}$ is a $C_6$-$C_{18}$aryl group; a $C_6$-$C_{18}$aryl group, substituted by a $C_1$-$C_{18}$alkyl, or a $C_1$-$C_{18}$alkoxy; a $C_1$-$C_{18}$alkyl group; or a $C_1$-$C_{18}$alkyl group, which is interrupted by —O—, $R^{68}$ is H; a $C_6$-$C_{18}$aryl group; a $C_6$-$C_{18}$aryl group, substituted by a $C_1$-$C_{18}$alkyl, or a $C_1$-$C_{18}$alkoxy; a $C_1$-$C_{18}$alkyl group; or a $C_1$-$C_{18}$alkyl group, which is interrupted by —O—;

$R^{69}$ is a $C_6$-$C_{18}$aryl; a $C_6$-$C_{18}$aryl, substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—;

$R^{70}$ and $R^{71}$ are each independently a $C_1$-$C_{18}$alkyl group, a $C_6$-$C_{18}$aryl group, or a $C_6$-$C_{18}$aryl group, substituted by $C_1$-$C_{18}$alkyl; and $R^{72}$ is a $C_1$-$C_{18}$alkyl group, a $C_6$-$C_{18}$aryl group, or a $C_6$-$C_{18}$aryl group, substituted by a $C_1$-$C_{18}$alkyl, with the proviso that the following compound is excluded:

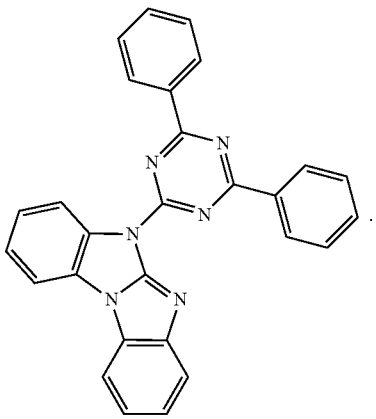 [SMILES: c1ccc(-c2nc(-c3ccccc3)nc(-n3c4ccccc4n4c5ccccc5nc34)n2)cc1]

2. The compound of claim 1, which is a compound of formula

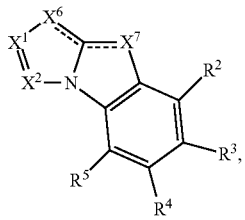

(I')

wherein:

$R^2$, $R^3$, $R^4$ and $R^5$ are each independently H, a $C_1$-$C_{25}$alkyl group, optionally substituted by E and/or interrupted by D; a $C_{6-24}$aryl group, optionally substituted by G, or a $C_2$-$C_{30}$heteroaryl group, optionally substituted by G.

3. The compound of claim 1, which is a compound of formula

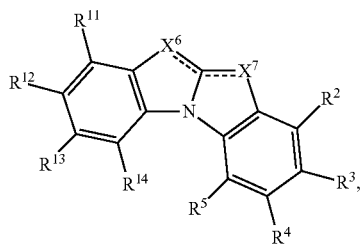

(II)

wherein $X^6$ is —N= and $X^7$ is —NR$^6$—; or
$X^7$ is =N— and $X^6$ is —NR$^6$—;
$R^6$ is a group of formula

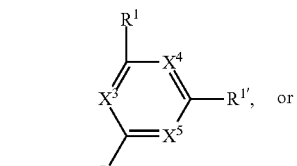

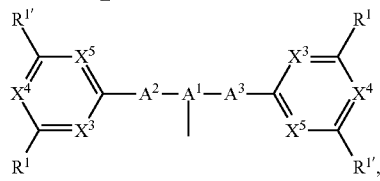

wherein $A^1$ is a group of formula

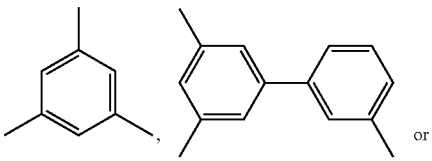

$A^2$ and $A^3$ are a group of formula

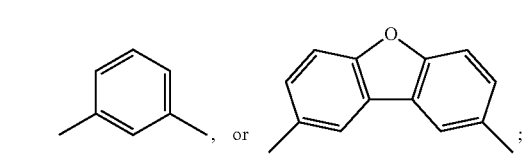

$R^{11}$, $R^{12}$, $R^{13}$ and $R^{14}$ are each independently H, a $C_1$-$C_{25}$alkyl group, optionally substituted by E and/or interrupted by D; a $C_6$-$C_{24}$aryl group, optionally substituted by G, or a $C_2$-$C_{30}$heteroaryl group, optionally substituted by G; and R², R³, R⁴ and R⁵ are each independently H, a C₁-C₂₅alkyl group, optionally substituted by E and/or interrupted by D; a C₆₋₂₄aryl group, optionally substituted by G, or a C₂-C₃₀heteroaryl group, optionally substituted by G.

4. The compound of claim 3, wherein R², R³, R⁴, R⁵, R¹¹, R¹², R¹³ and R¹⁴ are H.

5. The compound of claim 1, wherein R¹ and R¹' are each independently a group of formula

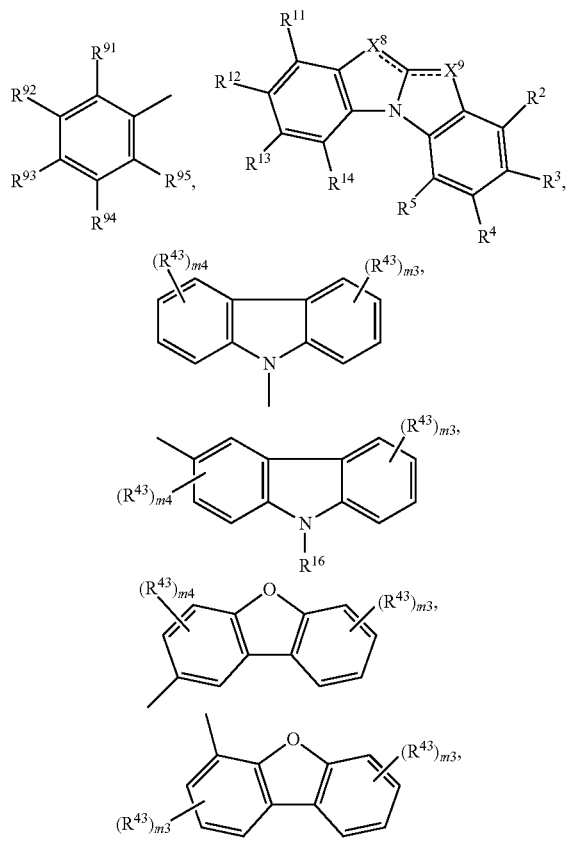

or a group —(SiR²⁰R²¹R²²), wherein
X⁸ is —N= and X⁹ is >N-L-;
X⁹ is =N— and X⁸ is >N-L-;
R², R³, R⁴, R⁵, R¹¹, R¹², R¹³ and R¹⁴ are each independently H, a C₁-C₂₅alkyl group, optionally substituted by E and/or interrupted by D; a C₆-C₂₄aryl group, optionally substituted by G, or a C₂-C₃₀heteroaryl group, optionally substituted by G;
R¹⁶ is a C₆-C₁₈aryl group; or a C₆-C₁₈aryl group, substituted by one, or more C₁-C₁₈alkyl groups;
R²⁰, R²¹ and R²² are each independently a C₆-C₁₈aryl group; or a C₆-C₁₈aryl group, substituted by one or more C₁-C₁₈alkyl groups;
R⁴³ may be the same, or different in each occurrence and is F, C₁-C₁₈alkyl, C₁-C₁₈alkyl substituted by E and/or interrupted by D, C₆-C₂₄aryl, C₆-C₂₄aryl which is substituted by G, C₂-C₂₀heteroaryl, or C₂-C₂₀heteroaryl which is substituted by G,
R⁹¹, R⁹², R⁹³, R⁹⁴ and R⁹⁵ are each independently H, a C₁-C₂₅alkyl group, optionally substituted by E and/or interrupted by D;
m3 is 0 or an integer of 1 to 4;
m4 is 0 or an integer of 1 to 3.

6. The compound of claim 5, wherein R¹ and R¹' are independently a group of formula

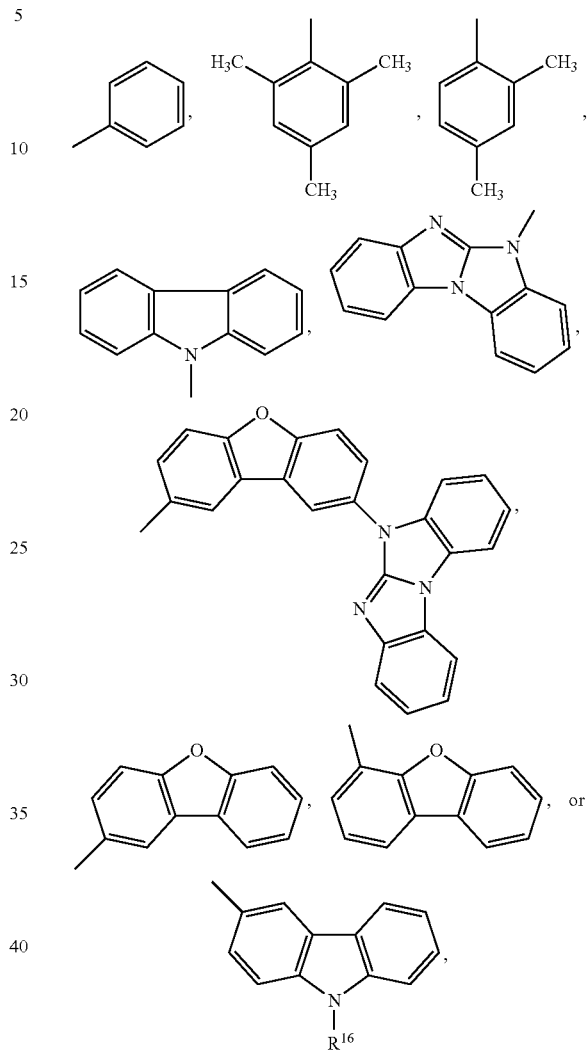

wherein R¹⁶ is a C₆-C₁₈aryl group; or a C₆-C₁₈aryl group, substituted by one or more C₁-C₁₈alkyl groups.

7. The compound of claim 1, wherein L is a single bond, a group of formula -(A⁴)ᵣ-(A⁵)ₛ-A⁶-, or

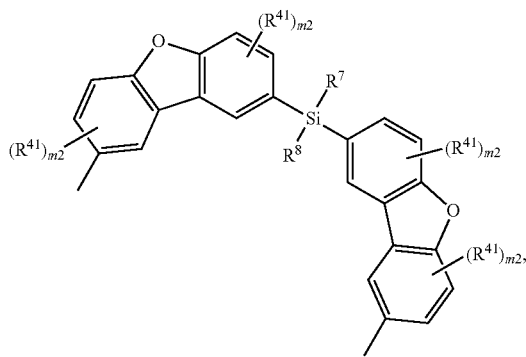

wherein

A⁴, A⁵ and A⁶ are each independently a group of formula

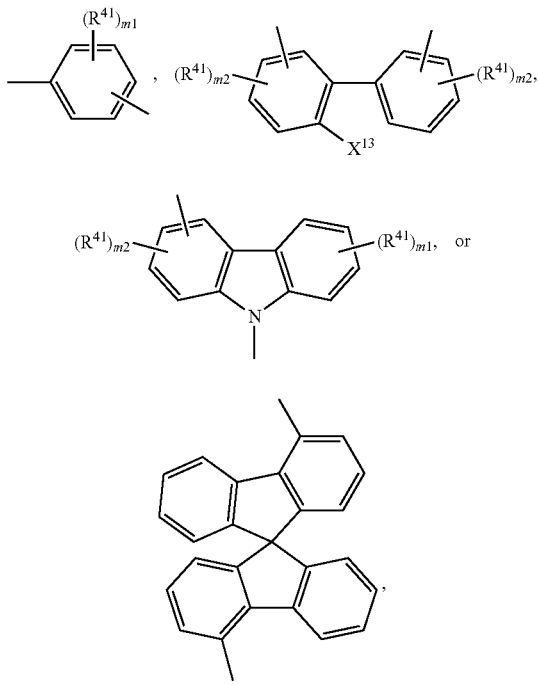

wherein
- R⁴¹ may be the same, or different in each occurrence and is F, $C_1$-$C_{18}$alkyl, $C_1$-$C_{18}$alkyl substituted by E and/or interrupted by D, $C_6$-$C_{24}$aryl, $C_6$-$C_{24}$aryl substituted by G, $C_2$-$C_{20}$heteroaryl, or $C_2$-$C_{20}$heteroaryl substituted by G,
- m1 is 0, or an integer of 1 to 4,
- m2 is 0, or an integer 1 to 3,
- r is 0, or 1; s is 0, or 1;
- $X^{13}$ is —O—, —S—, or —NR¹⁵—,
- R¹⁵ is a $C_1$-$C_{18}$alkyl group; or a $C_1$-$C_{18}$alkyl group, interrupted by —O—; a $C_6$-$C_{18}$aryl group; a $C_6$-$C_{18}$aryl group, substituted by one or more $C_1$-$C_{18}$alkyl groups, or $C_1$-$C_{18}$alkoxy groups; a $C_2$-$C_{20}$heteroaryl group, or a $C_2$-$C_{20}$heteroaryl group, substituted by one or more $C_1$-$C_{18}$alkyl groups,
- R⁷ and R⁸ are a $C_1$-$C_{18}$alkyl group.

8. The compound of claim 7, wherein A⁴, A⁵ and A⁶ are each independently a group of formula

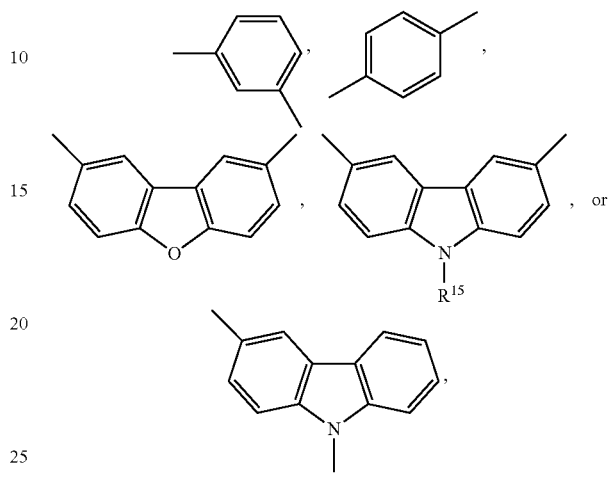

wherein
- R¹⁵ is a $C_6$-$C_{18}$aryl group; or a $C_6$-$C_{18}$aryl group, which is substituted by one, or more $C_1$-$C_{18}$alkyl groups.

9. The compound of claim 1, having a formula:

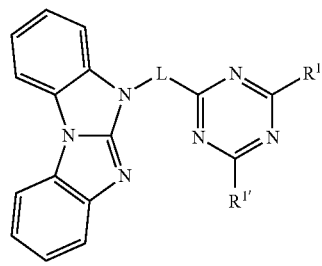

wherein L, R¹ and R¹' are defined by any one of the compounds A-1-A-18:

| Cpd. | L³⁾ | R¹ | R¹' |
|---|---|---|---|
| A-1 | ![dibenzofuran] | ![tolyl] | ![tolyl] |
| A-2 | ![dibenzofuran] | ![mesityl with CH₃] | ![mesityl with CH₃] |

-continued

| Cpd. | L³⁾ | R¹ | R¹' |
|---|---|---|---|
| A-3 | 2-(3-phenyl)dibenzofuran-8-methyl | phenyl | phenyl |
| A-4 | 2-(3-phenyl)dibenzofuran-8-methyl | 2,4,6-trimethylphenyl | 2,4,6-trimethylphenyl |
| A-5 | 3,3'-biphenyl | phenyl | phenyl |
| A-6 | bis(dibenzofuran-2,8-diyl) | phenyl | phenyl |
| A-7 | dibenzofuran-2,8-diyl | 1) | 2,4,6-trimethylphenyl |
| A-8 | dibenzofuran-2,8-diyl | 1) | phenyl |
| A-9 | single bond | phenyl | phenyl |

-continued
| Cpd. | L³⁾ | R¹ | R¹' |
|---|---|---|---|
| A-10 | single bond | 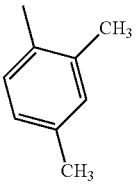 | 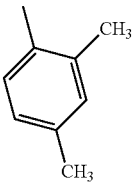 |
| A-11 | single bond | 2) | 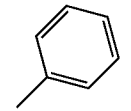 |
| A-12 | single bond | 2) | 2) |
| A-13 | 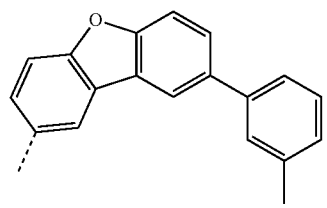 | 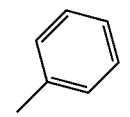 | 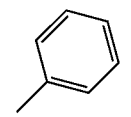 |
| A-14 | 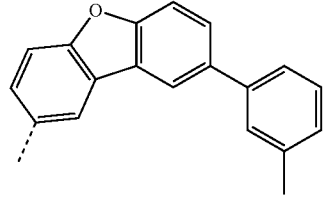 | 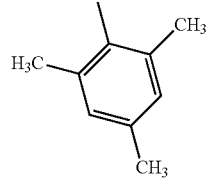 | 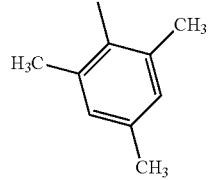 |
| A-15 | single bond | 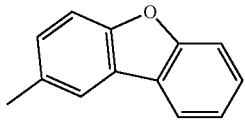 | 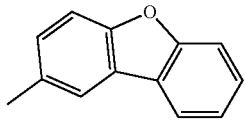 |
| A-16 | 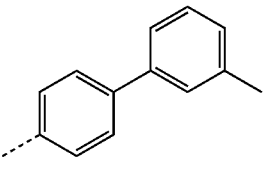 | 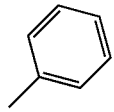 | 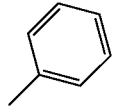 |
| A-17 | 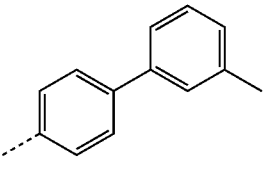 | 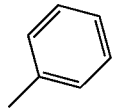 | 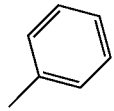 |
| A-18 | single bond | 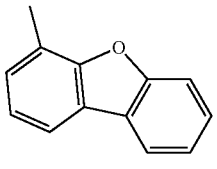 | 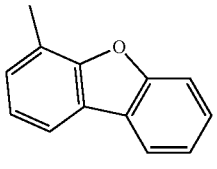 | or having a formula:
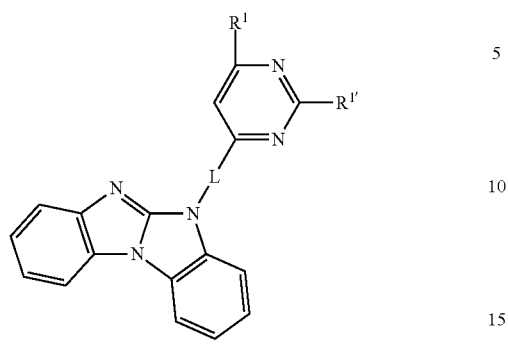
wherein L, R¹ and R¹' are defined by any one of the compounds B-1-B-18:
| Cpd. | L³⁾ | R¹ | R¹' |
|---|---|---|---|
| B-1 | 2-dibenzofuranyl | phenyl | phenyl |
| B-2 | 2-dibenzofuranyl | mesityl | mesityl |
| B-3 | 8-phenyl-2-dibenzofuranyl (with phenyl at meta position) | phenyl | phenyl |
| B-4 | 8-phenyl-2-dibenzofuranyl (with phenyl at meta position) | mesityl | mesityl |
| B-5 | 3'-biphenylyl | phenyl | phenyl |

-continued

| Cpd. | L³⁾ | R¹ | R¹' |
|---|---|---|---|
| B-6 | (dibenzofuran-dibenzofuran linked group) | phenyl | phenyl |
| B-7 | (2-dibenzofuranyl) | 1) | 2,4,6-trimethylphenyl |
| B-8 | (2-dibenzofuranyl) | 1) | phenyl |
| B-9 | single bond | phenyl | phenyl |
| B-10 | single bond | 2,4-dimethylphenyl | 2,4-dimethylphenyl |
| B-11 | single bond | 2) | phenyl |
| B-12 | single bond | 2) | 2) |
| B-13 | (2-(3-phenyl)dibenzofuranyl) | phenyl | phenyl |

-continued
| Cpd. | L[3)] | R[1] | R[1'] |
|---|---|---|---|
| B-14 | 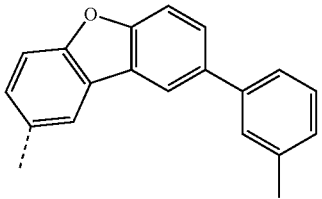 | 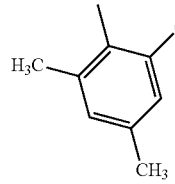 | 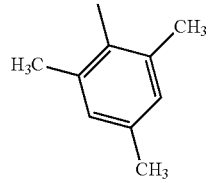 |
| B-15 | single bond | 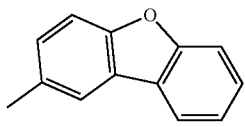 | 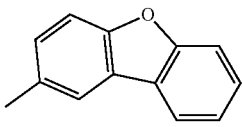 |
| B-16 | 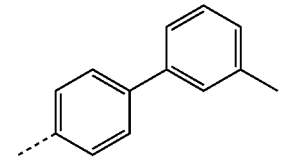 | 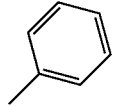 | 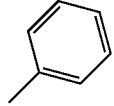 |
| B-17 | 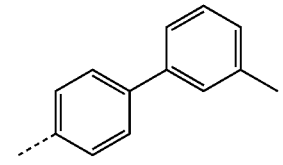 | 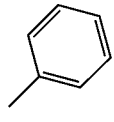 | 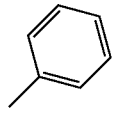 |
| B-18 | single bond | 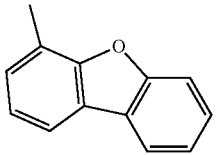 | 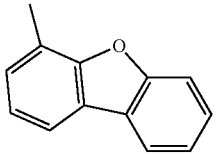 |
or having a formula:
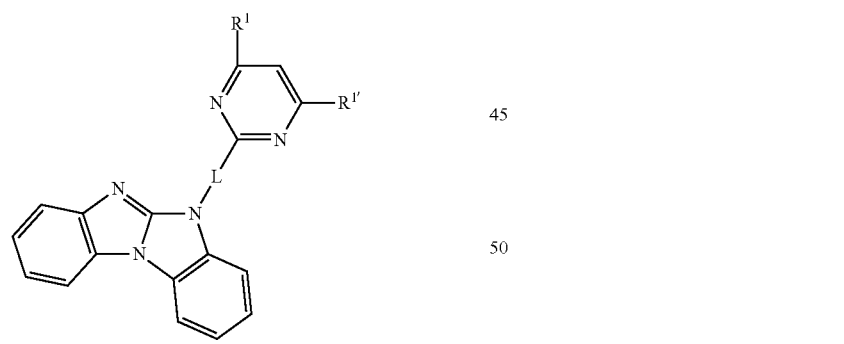
wherein L, R[1], and R[1'] are defined by any one of the compounds C-1-C-18:
| Cpd. | L[3)] | R[1] | R[1'] |
|---|---|---|---|
| C-1 | 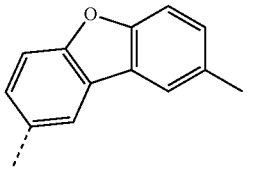 | 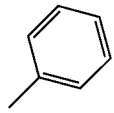 | 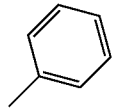 |

-continued

| Cpd. | L³⁾ | R¹ | R¹' |
|---|---|---|---|
| C-2 | dibenzofuran-2,8-diyl | mesityl | mesityl |
| C-3 | 2-(dibenzofuran-2-yl)-phenyl-3-yl | phenyl | phenyl |
| C-4 | 2-(dibenzofuran-2-yl)-phenyl-3-yl | mesityl | mesityl |
| C-5 | biphenyl-3,3'-diyl | phenyl | phenyl |
| C-6 | 2,2'-bidibenzofuran-8,8'-diyl | phenyl | phenyl |
| C-7 | dibenzofuran-2,8-diyl | 1) | mesityl |
| C-8 | dibenzofuran-2,8-diyl | 1) | phenyl |

-continued
| Cpd. | L[3)] | R[1] | R[1'] |
|---|---|---|---|
| C-9 | single bond | 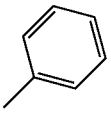 | 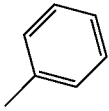 |
| C-10 | single bond | 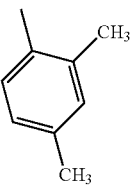 | 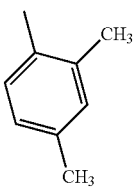 |
| C-11 | single bond | [2)] | 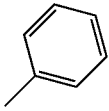 |
| C-12 | single bond | [2)] | [2)] |
| C-13 | 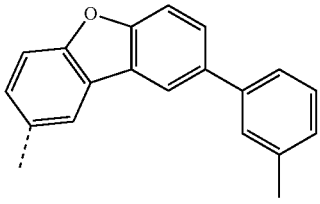 | 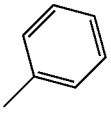 | 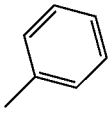 |
| C-14 | 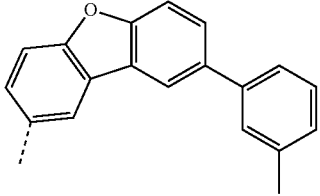 | 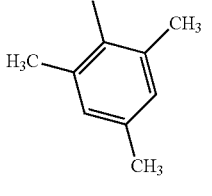 | 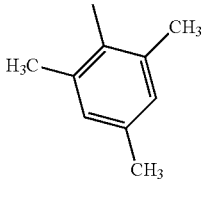 |
| C-15 | single bond | 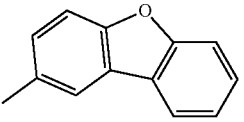 | 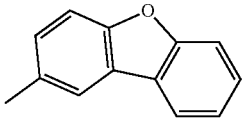 |
| C-16 | 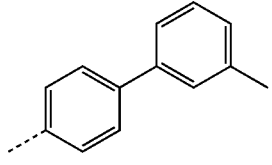 | 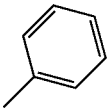 | 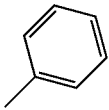 |
| C-17 | 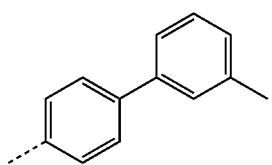 | 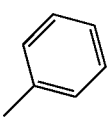 | 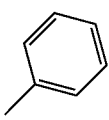 |
| C-18 | single bond | 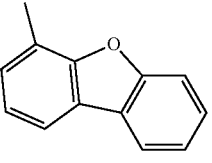 | 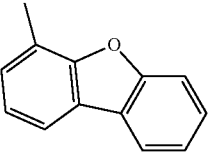 | or having a formula:
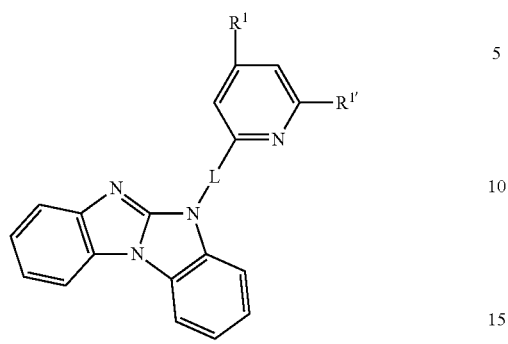
wherein L, $R^1$, and $R^{1'}$ are defined by any one of the compounds D-1-D-19:
| Cpd. | L[3)] | $R^1$ | $R^{1'}$ |
|---|---|---|---|
| D-1 | 2-methyldibenzofuran-8-yl | tolyl | tolyl |
| D-2 | 2-methyldibenzofuran-8-yl | mesityl | mesityl |
| D-3 | 8-methyl-2-(phenyl)dibenzofuran-3'-yl | tolyl | tolyl |
| D-4 | 8-methyl-2-(phenyl)dibenzofuran-3'-yl | mesityl | mesityl |
| D-5 | 3'-methylbiphenyl-3-yl | tolyl | tolyl |

-continued

| Cpd. | L³⁾ | R¹ | R¹' |
|---|---|---|---|
| D-6 | dibenzofuran-dibenzofuran linker | phenyl | phenyl |
| D-7 | dibenzofuran | 1) | 2,4,6-trimethylphenyl |
| D-8 | dibenzofuran | 1) | phenyl |
| D-9 | single bond | phenyl | phenyl |
| D-10 | single bond | 2,4-dimethylphenyl | 2,4-dimethylphenyl |
| D-11 | single bond | 2) | phenyl |
| D-12 | single bond | 2) | 2) |
| D-13 | single bond | H | 2) |
| D-14 | dibenzofuran-phenyl | phenyl | phenyl |

-continued
| Cpd. | L³⁾ | R¹ | R¹' |
|---|---|---|---|
| D-15 | 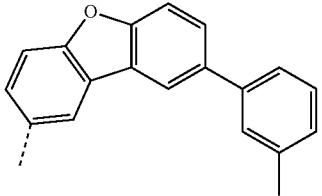 | 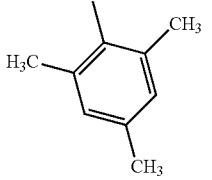 | 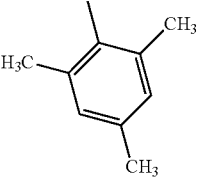 |
| D-16 | single bond | 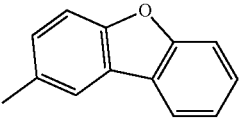 | 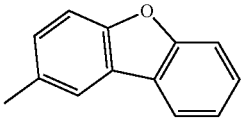 |
| D-17 | 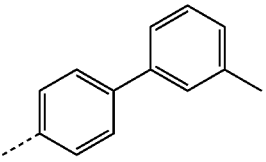 | 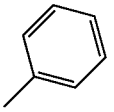 | 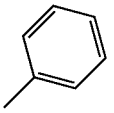 |
| D-18 | 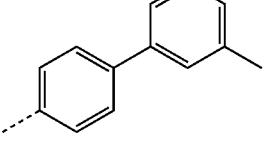 | 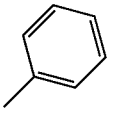 | 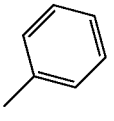 |
| D-19 | single bond | 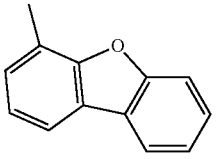 | 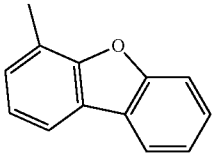 |
¹⁾R¹ is a group of formula 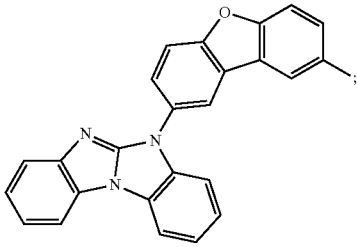;
²⁾R¹ is a group of formula 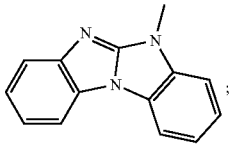;
³⁾The dotted line indicates the bond to the group of formula 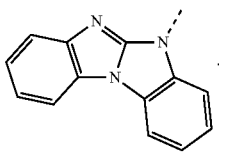.

or having a formula:
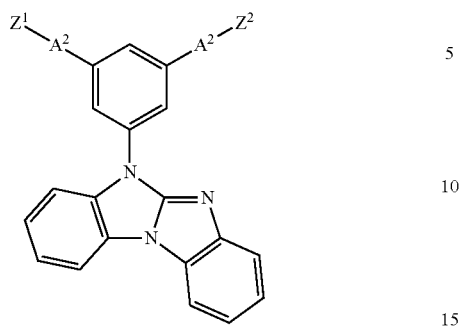
wherein $Z^1$, $Z^2$, and $A^2$ are defined by any one of the compounds E-1-E-6:
| Cpd. | $Z^1$ | $Z^2$ | $A^2$ |
|---|---|---|---|
| E-1 | 4,6-diphenyl-1,3,5-triazin-2-yl | 4,6-diphenyl-1,3,5-triazin-2-yl | 1,3-phenylene |
| E-2 | 2,6-diphenylpyrimidin-4-yl | 2,6-diphenylpyrimidin-4-yl | 1,3-phenylene |
| E-3 | 2,4-diphenylpyridin-6-yl | 2,4-diphenylpyridin-6-yl | 1,3-phenylene |

-continued

| Cpd. | Z¹ | Z² | A² |
|---|---|---|---|
| E-4 | | | |
| E-5 | | | |
| E-6 | | | |

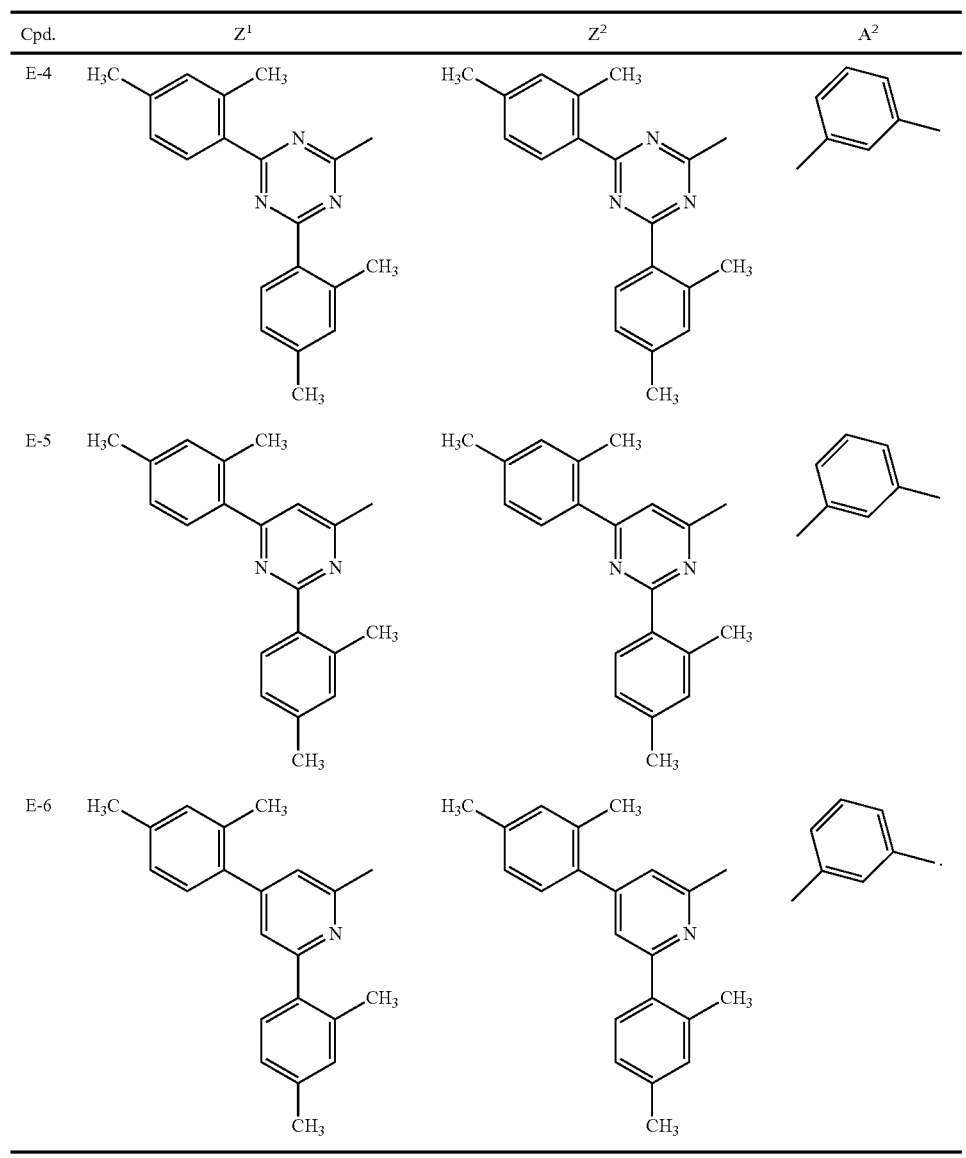

10. An electronic device, comprising the compound of claim 1.

11. The electronic device of claim 10, wherein the electronic device is an electroluminescent device.

12. An electron transport layer, a hole/exciton blocking layer, or an emitting layer comprising the compound of claim 1.

13. An emitting layer, comprising a compound of claim 1 as a host material in combination with a phosphorescent emitter.

14. An apparatus selected from the group consisting of a stationary visual display unit, a mobile visual display unit, an illumination unit, a keyboard, an item of clothing, a furniture, and a wallpaper, comprising the electronic device of claim 10.

15. An electrophotographic photoreceptor, a photoelectric converter, an organic solar cell, a switching element, an organic light emitting field effect transistor, an image sensor, a dye laser or an electroluminescent device comprising the compound of claim 1.

* * * * *